US009376430B2

(12) United States Patent
Hoffman et al.

(10) Patent No.: US 9,376,430 B2
(45) Date of Patent: *Jun. 28, 2016

(54) BROAD SPECTRUM BENZOTHIOPHENE-NITROTHIAZOLIDE AND OTHER ANTIMICROBIALS

(71) Applicants: Paul S. Hoffman, Charlottesville, VA (US); Richard L. Guerrant, Charlottesville, VA (US); Timothy L. Macdonald, Charlottesville, VA (US); Thomas Eric Ballard, Jr., Middletown, CT (US)

(72) Inventors: Paul S. Hoffman, Charlottesville, VA (US); Richard L. Guerrant, Charlottesville, VA (US); Timothy L. Macdonald, Charlottesville, VA (US); Thomas Eric Ballard, Jr., Middletown, CT (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/446,793

(22) Filed: Jul. 30, 2014

(65) Prior Publication Data

US 2015/0018330 A1 Jan. 15, 2015

Related U.S. Application Data

(63) Continuation of application No. 13/257,707, filed as application No. PCT/US2010/027397 on Mar. 16, 2010, now Pat. No. 8,835,644.

(60) Provisional application No. 61/161,796, filed on Mar. 20, 2009.

(51) Int. Cl.
| | |
|---|---|
| *A61K 31/427* | (2006.01) |
| *A61K 31/426* | (2006.01) |
| *A61K 31/381* | (2006.01) |
| *A61K 31/4439* | (2006.01) |
| *C07D 417/14* | (2006.01) |
| *C07D 277/54* | (2006.01) |
| *C07D 277/58* | (2006.01) |
| *C07D 333/42* | (2006.01) |
| *C07D 409/12* | (2006.01) |
| *C07D 417/12* | (2006.01) |
| *C07D 333/44* | (2006.01) |

(52) U.S. Cl.
CPC ............ *C07D 417/14* (2013.01); *A61K 31/381* (2013.01); *A61K 31/426* (2013.01); *A61K 31/427* (2013.01); *A61K 31/4439* (2013.01); *C07D 277/54* (2013.01); *C07D 277/58* (2013.01); *C07D 333/42* (2013.01); *C07D 333/44* (2013.01); *C07D 409/12* (2013.01); *C07D 417/12* (2013.01)

(58) Field of Classification Search
None
See application file for complete search history.

(56) References Cited

U.S. PATENT DOCUMENTS

| 2,735,798 | A | | 2/1956 | Kupferberg et al. | |
|---|---|---|---|---|---|
| 3,957,812 | A | * | 5/1976 | Rossignol et al. | 548/192 |
| 5,071,865 | A | * | 12/1991 | Beck et al. | 514/370 |
| 5,578,621 | A | * | 11/1996 | Rossignol | 514/371 |
| 5,856,347 | A | * | 1/1999 | Hashiguchi et al. | 514/370 |
| 2004/0235914 | A1 | | 11/2004 | Ammendola et al. | |
| 2005/0113420 | A1 | | 5/2005 | Nan et al. | |
| 2009/0036467 | A1 | | 2/2009 | Rossignol et al. | |
| 2009/0069248 | A1 | | 3/2009 | Motin et al. | |
| 2013/0317070 | A1 | * | 11/2013 | Hoffman et al. | 514/342 |
| 2015/0133366 | A1 | * | 5/2015 | Guerrant et al. | 514/2.9 |

FOREIGN PATENT DOCUMENTS

| EP | 0566138 A1 | | 10/1993 |
|---|---|---|---|
| FR | 1306603 A | | 9/1962 |
| GB | 723948 | | 2/1955 |
| JP | 39-018145 B | * | 8/1964 |
| WO | WO0026202 A1 | | 5/2000 |
| WO | WO03089419 A1 | | 10/2003 |
| WO | WO2004031179 A1 | | 4/2004 |
| WO | WO2004056177 A2 | | 7/2004 |
| WO | WO2006093518 A2 | | 9/2006 |
| WO | WO2007075414 A2 | | 7/2007 |
| WO | WO2007081974 A2 | | 7/2007 |
| WO | WO2007125109 | | 11/2007 |

OTHER PUBLICATIONS

Micich, Journal of the American Oil Chemists Society, vol. 59, No. 10, Oct. 1982, pp. 448-452.*
Dubreuil et al., Antimicrobial Agents and Chemotherapy, Oct. 1996, pp. 2266-2270.*

(Continued)

*Primary Examiner* — Laura L. Stockton
(74) *Attorney, Agent, or Firm* — Rodney L. Sparks

(57) ABSTRACT

The invention provides novel antimicrobial chemical entities based on a nitrothiazolide backbone that exhibit antibacterial and antiparasitic action against a wide range of human pathogens. The new classes of compounds show extended action against Gram positive bacteria including MRSA drug resistant pathogens. In the Gram-positive organisms, they specifically target and functionally inhibit microbial attachment to surfaces and biofilm formation. In Gram-negative bacteria, including enteroaggregative *E. coli* strains, these compounds function as pilicides by inhibiting the assembly of pilin subunits into adhesive filaments. Several of these compounds show potent antimicrobial action against Gram positive bacteria, perhaps involving novel targets. Many of the benzothiophene derivatives exhibit antimicrobial activity in the low micrograms per ml range and in blocking biofilm formation in the nanomolar range; ranges considered are well within the range of utility as therapeutics.

17 Claims, 34 Drawing Sheets

(56) References Cited

OTHER PUBLICATIONS

Cavier et al., European Journal of Medicinal Chemistry, 1978, 13(6), pp. 539-543.*
An English translation of Cavier et al., European Journal of Medicinal Chemistry, 1978, 13(6), pp. 539-543.*
Buu-Hoï et al., Journal of the Chemical Society, 1958, pp. 2815-2821.*
Bellenghi et al., Gazzetta Chimica Italiana, 1952, 82, pp. 773-807.*
Bellenghi et al., CA 48:11036, 1954.*
An English translation of Bellenghi et al., Gazzetta Chimica Italiana, 1952, 82, pp. 773-807.*
Hof et al., Journal of Antimicrobial Chemotherapy, 1985, 16(2), pp. 205-210.*
Dymicky et al., Antimicrobial Agents and Chemotherapy, 1977, 12(3), pp. 353-356.*
Hosokawa, Ann. Rept. Research Inst. Tuberc., Kanazawa Univ., 1953, 11(No. 2), pp. 43-57.*
An English translation of Hosokawa, Ann. Rept. Research Inst. Tuberc., Kanazawa Univ., 1953, 11(No. 2), pp. 43-57.*
Bushby et al., Journal of Pharmacy and Pharmacology, vol. 7, Issue 1, Aug.-Sep. 1955, pp. 112-117.*
An English translation of Sugihara et al., JP 39-018145B, 1964.*
Luo, Qun-Li, et al., "Inhibitors of type I MetAps containing pyridine-2-carboxylic acid thiazole-2-ylamide. Part I: SAR studies on the determination of the key scaffold", Bioorganic & Medicinal Chemistry Letters, 2005, vol. 15, pp. 635-638.
Helal, Christopher J., et al., "Discovery and SAR of 2-aminothiazone inhibitors of cyclin-dependent kinase 5/p25 as a potential treatment for Alzheimer's disease", Bioorganic & Medicinal Chemistry Letters, 2004, vol. 14, pp. 552-1-5525.
McVay, Catherine S., et al., "In Vitro and In Vivo Activities of Nitazoxanide against Clostridium difficile", Antimicrob. Agents Chemother., vol. 44, No. 9, 2000, pp. 2254-2258, XP55032067.
Sokolova, T.N., et al., "Synthesis and Antimicrobial Activity of Derivatives", Pharmaceutical Chemistry, vol. 27, No. 3, 1993, pp. 209-211, XP002679654.
Werbel, L.M., "Derivatives of 2-Amino-5-nitrothiazole as Potential Schistosomicides", Journal of Medicinal Chemistry, vol. 14, No. 1, 1971, pp. 10-16, XP002679655.
Bushby, S.R.M., "The Antitrichomal Activity of Amido-Nitrothiazols", J. Pharmacol., vol. 7, 1955, pp. 112-114, XP009161073.
Hoffman, Paul S., et al., "Antiparasitic Drug Nitazoxanide Inhibits the Pyruvate Oxidoreductases of Helicobacter pylori, Selected Anaerobic Bacteria and Parasites, and Campylobacter jejuni", Antimicrobial Agents and Chemo., Mar. 2007, vol. 51, No. 3., p. 868-876.
de Carvalho, Luiz Pedro S., et al., "Nitazoxanide Kills Replicating and Nonreplicating Mycobacterium tuberculosis and Evades Resistance", J. Med. Chem., 2009, 52, p. 5789-5792.
Dubreuil, L., et al., "In vitro evaluation of activities of nitazoxanide and tizoxanide against anaerobes and aerobic organisms", Antimicrob. Agents Chemother., 40:2266-2270, 1996.
Hemphill, A. et al., "Nitazoxanide, a broad-spectrum thiazolide anti-effective agent for the treatment of gastrointestinal infections", Expert Opin. Pharmacother. 7:953-964, 2006.
Pankuch, G. A., et al., "Activities of Tizoxanide and Nitazoxanide Compared to Those of Five Other Thiazolides and Three Other Agents against Anaerobic Species", Antimicrob. Agents Chemother. 50: 1112-1117, 2006.
Sisson, G., et al., "Enzymes Associated with Reductive Activation and Action of Nitazoxanide, Nitrofurans, and Metronidazole in Helicobacter pylori", Antimicrob. Agents Chemother. 46:2116-23, 2002.
Zulu, I., et al., "Nitazoxanide for persistent diarrhoea in Zambian acquired immune deficiency syndrome patients: a randomized-controlled trial", Aliment Pharmacol. Ther., 21:757-763, 2005.
Madulo-LeBlond, G., et al., EU Jrnl. of Med. Chemistry, 1981, V 16, pp. 267-270.
Ganapathi, K., et al., "Chemistry of the Thiazoles", Part I., Synthesis of 5-Aminothiazole Derivatives, Proc. of Indian Academy of Sciences, Section A, 1945, v. 22, pp. 343-358.
Sugihara, et al., "Nitrothiazole derivatives having nitrofuryl groups", Chem Abs DN 62-29716, Aug. 28, 1964, pp. 1.
Chemical Abstracts Registry No. 710310-02-04, Jul. 15, 2004, pp. 1.
Husain, Md. I., et al., "Search for Potent Anthelmintics—Part XIII 2-(3,5-Substituted Salicylamido/Cinnamido)-4,5-Substituted Thiazoles", J. Indian Chem. Soc., V. LVI, Sep. 1979, pp. 917-918.
Morley, J., et al., "Structure-activity elationships in nitrothiophenes", Biorganic & Med. Chem., 14 (2006), pp. 8099-8108.

* cited by examiner

Aliphatic Derivatives of 2-amino-5-nitrothiazole

Aliphatic Amine Analogues of 2-amino-5-nitrothiazole

Amino Acid Analogues of 2-amino-5-nitrothiazole

Anthranilic Analogues of 2-amino-5-nitrothiazole

Pyridine Analogues of 2-amino-5-nitrothiazole

Indole Analogues of 2-amino-5-nitrothiazole

Carboxylic Acid Analogues of 2-amino-5-nitrothiazole

Dimer-like Analogues of 2-amino-5-nitrothiazole

Halide Analogues of 2-amino-5-nitrothiazole

Monosubstituted Analogues of 2-amino-5-nitrothiazole

Disubstituted Analogues of 2-amino-5-nitrothiazole

Furan Analogues of 2-amino-5-nitrothiazole

Thiophene Analogues of 2-amino-5-nitrothiazole

Amide Isosteres of 2-amino-5-nitrothiazole

Analogues of 2-amino-4-chloro-5-nitrothiazole

Analogues of 2-amino-3,5-dinitrothiophene

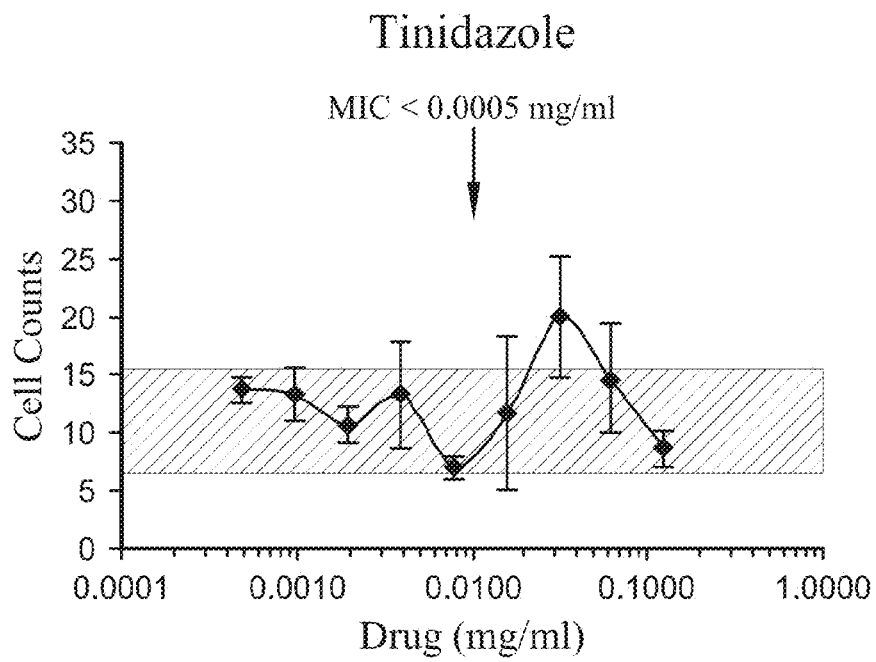
FIG. 32A1
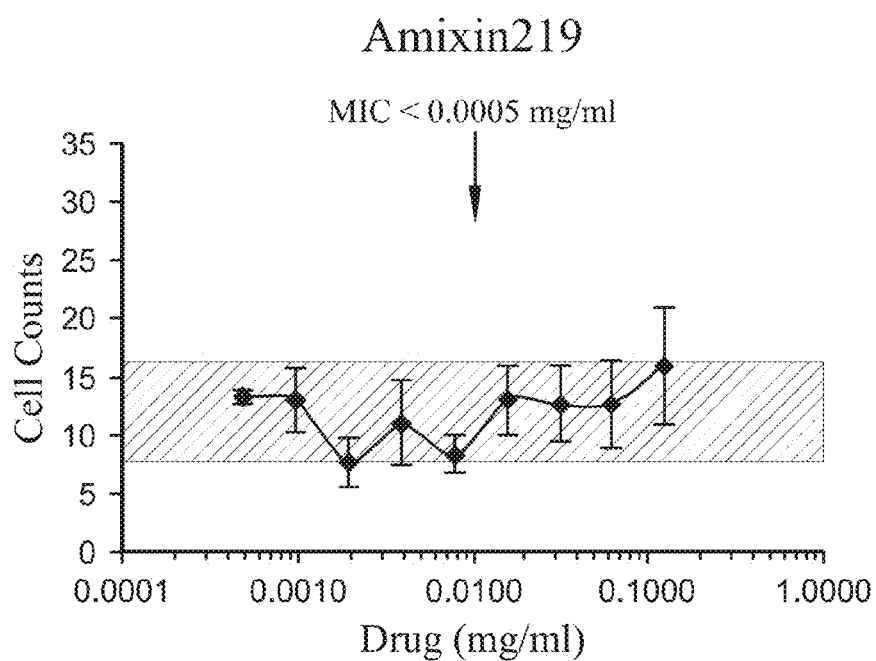
FIG. 32A2

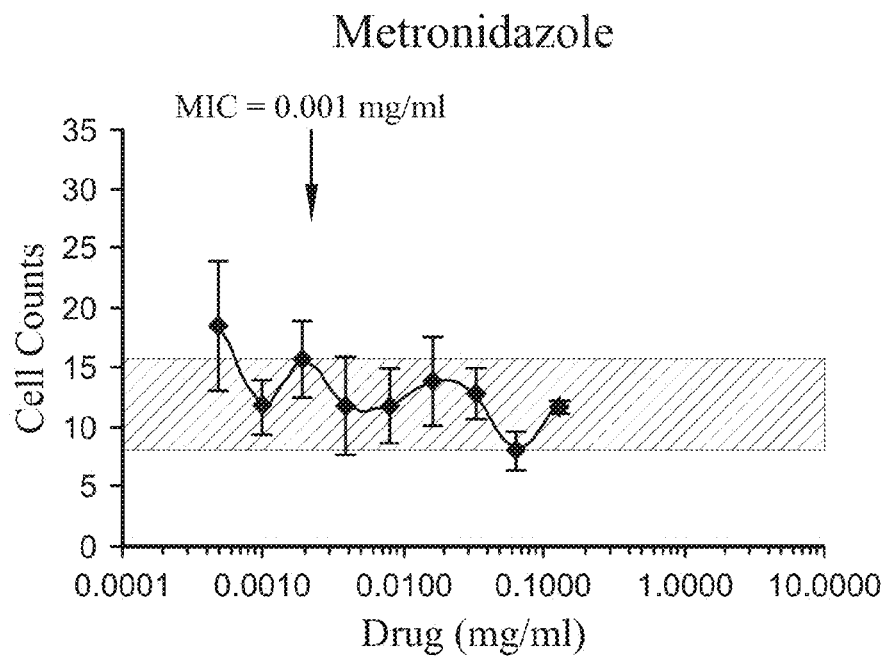
FIG. 32A3
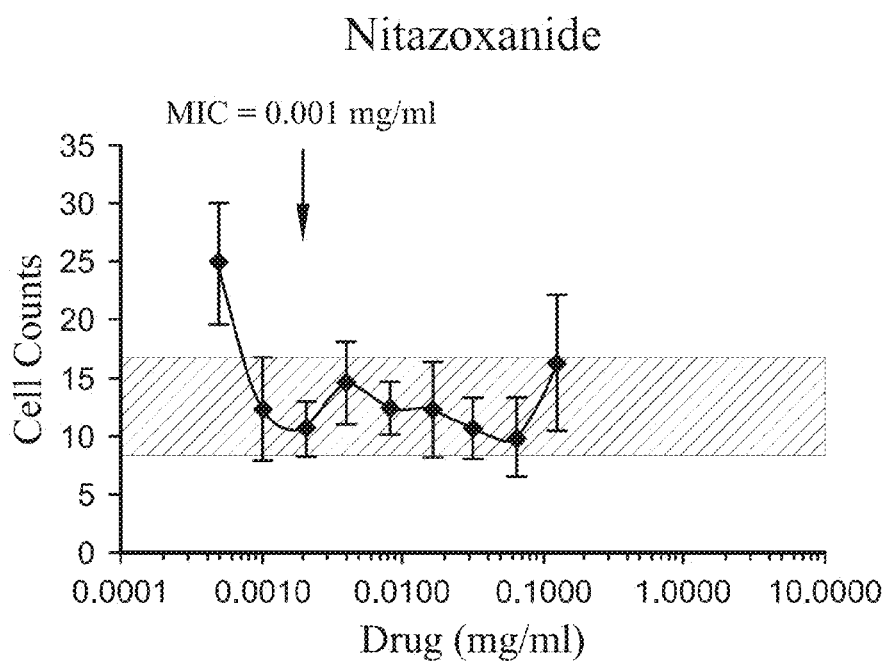
FIG. 32A4

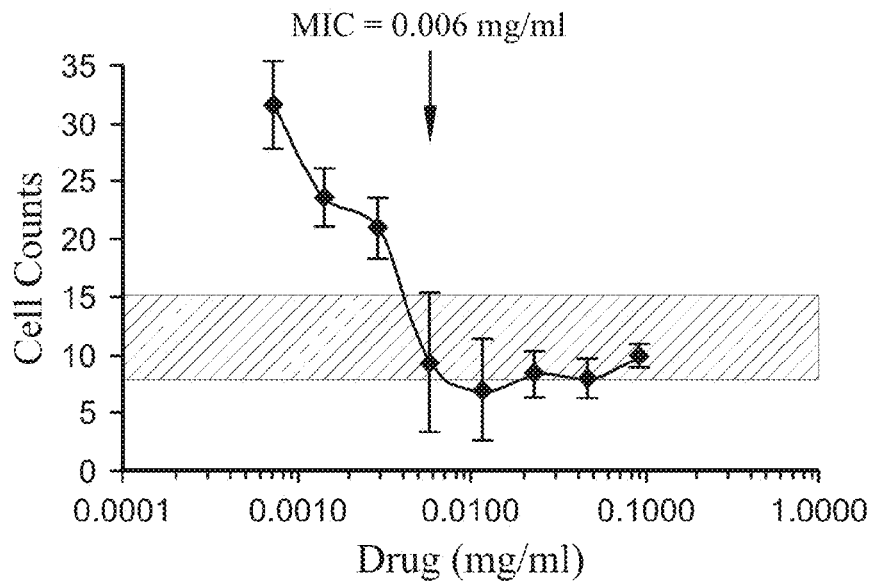
FIG. 32A5
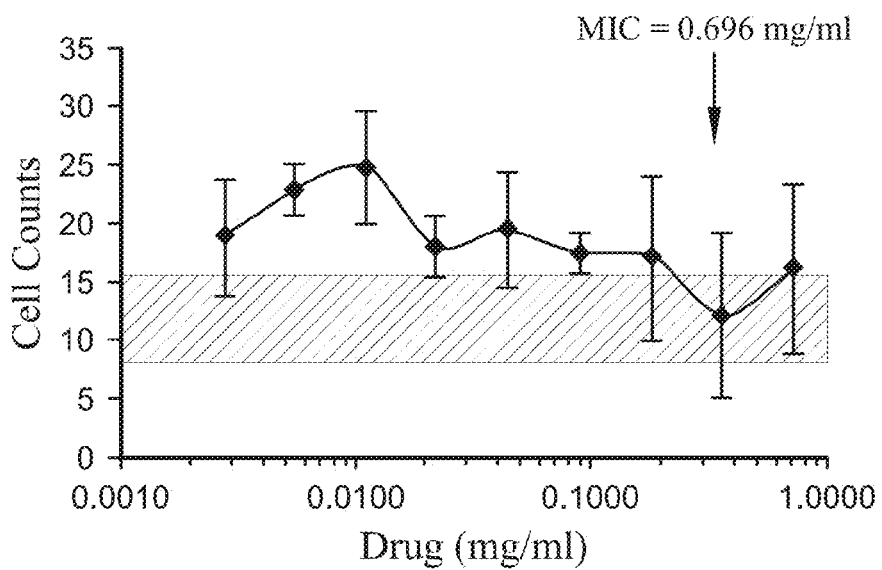
FIG. 32A6

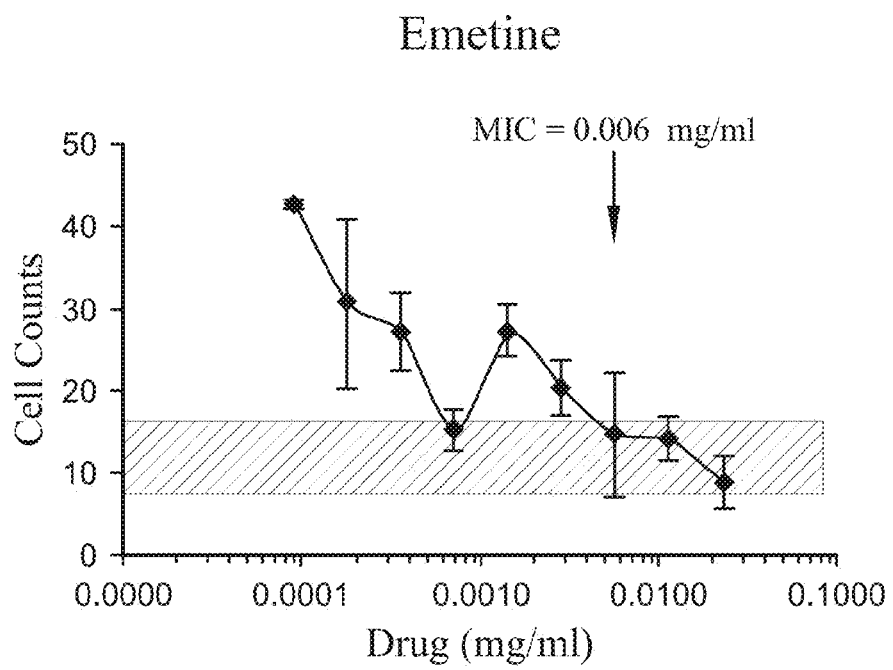
FIG. 32A7
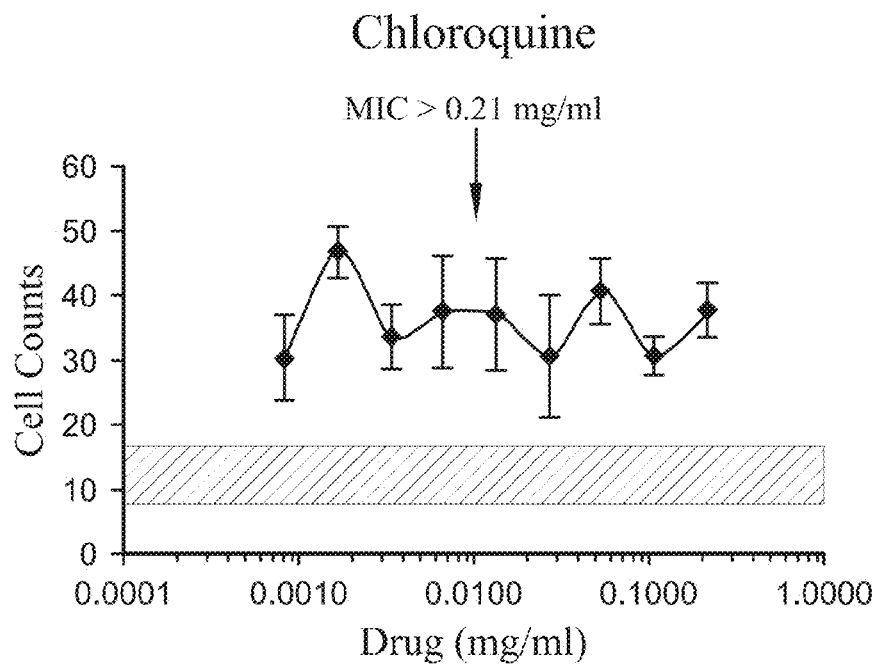
FIG. 32A8

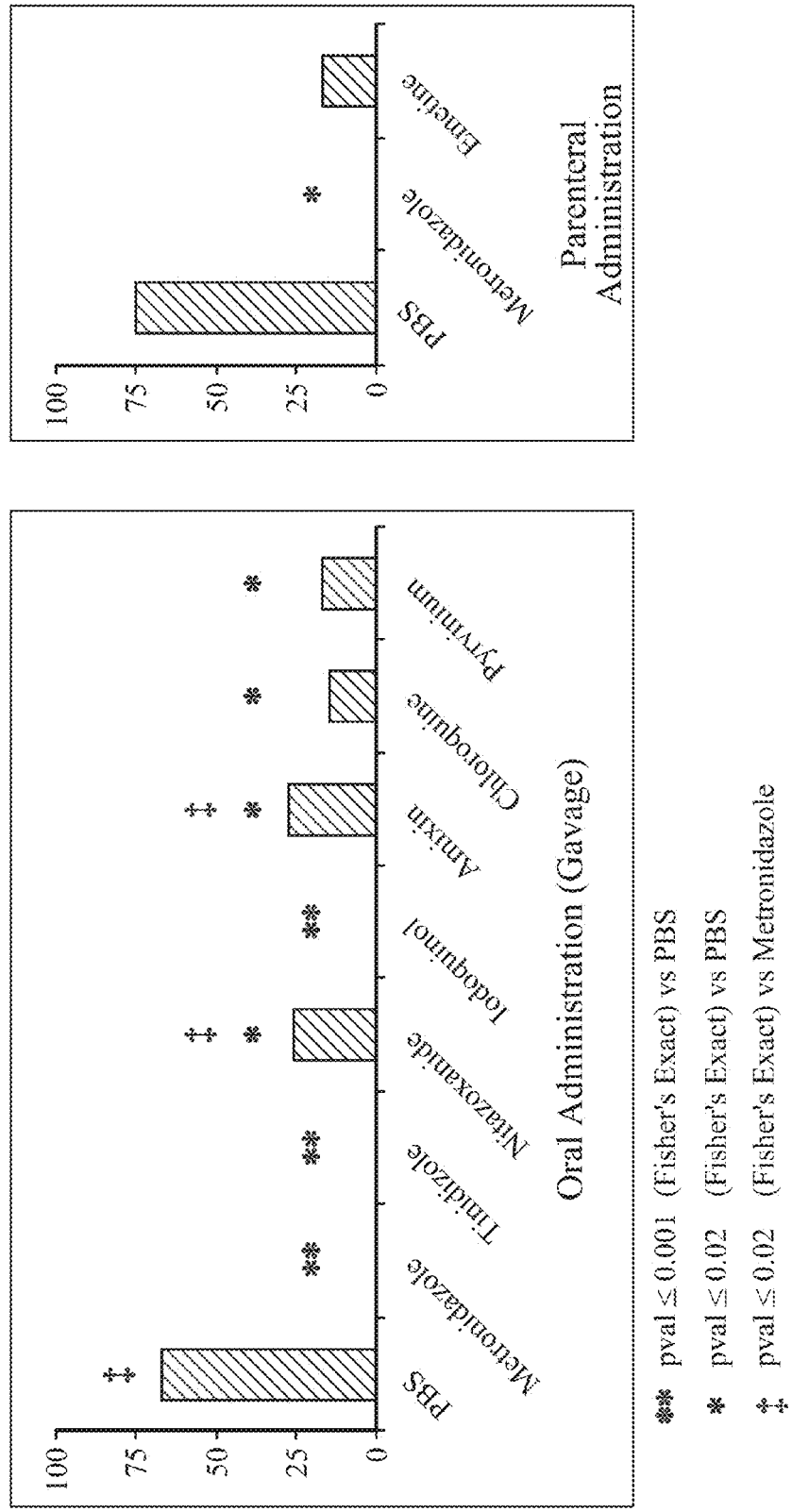
FIG. 32 B2
FIG. 32 B1

BROAD SPECTRUM BENZOTHIOPHENE-NITROTHIAZOLIDE AND OTHER ANTIMICROBIALS

CROSS REFERENCE TO RELATED APPLICATIONS

This application is entitled to priority pursuant to 35 U.S.C. §119(e) to U.S. provisional patent application No. 61/161,796, filed on Mar. 20, 2009. The entire disclosure of the afore-mentioned patent application is incorporated herein by reference.

STATEMENT REGARDING FEDERALLY SPONSORED RESEARCH OR DEVELOPMENT

This invention was made in part with United States Government support under Grant No. U01 A1075520 awarded by the National Institutes of Health. The United States Government has certain rights in the invention.

BACKGROUND

Nitazoxanide (NTZ; 2-(acetyloxy)-N-(5-nitro-2-thiazolyl)benzamide) is an FDA approved antiparasitic drug useful for the treatment of *Giardia* and *Cryptosporidium* infections in adults and children. It is a broad spectrum antiparasitic and anti-diarrheal. NTZ efficacy is limited by its poor solubility and strong binding and inactivation by serum proteins.

Coagulase-negative staphylococci (CoNS) have emerged as important opportunistic hospital acquired pathogens that are the leading cause of catheter and indwelling device-associated infections. The ability of CoNS, including the archetypal species *Staphylococcus epidermidis*, to cause disease depends on their ability to adhere to polymer surfaces where they form thick, multilayered, cellular agglomerations known as biofilm. The principal components of *S. epidermidis* biofilm include poly-β-1,6-N-acetyl-D-glucosamine (PNAG, also known as PIA for polysaccharide intercellular adhesion), synthesized by the products of the ica genes, and surface proteins such as the accumulation associated protein Aap. Biofilm contributes to persistence by limiting efficacy of antibiotics and host immune responses. Bloodstream and urinary tract infections ranked as 2nd and 3rd causes respectively of healthcare-associated deaths in the US in 2002. More than 5 million central venous catheters are inserted annually in the U.S. and of the more than 200,000 healthcare-acquired bloodstream infections that occur annually, most are due to central venous catheter. These infections lead to increased morbidity, mortality, lengths of hospitalization, and total healthcare costs.

Many drugs and compounds have been tested as biofilm inhibitors and some are used to coat catheters (e.g. silver, minocycline, rifampin, platinum, nitrofurantoin, chlorhexidine, and sulfadiazine). Several randomized trials have shown benefits of using antibiotic(s)-impregnated catheters in hospitalized patients to reduce colonization and catheter-related bloodstream infections (CRBSI) and include: chlorhexidine-silver sulfadiazine impregnated catheters compared with non impregnated catheters; rifampin-minocycline coated catheters compared with non-coated catheters; and rifampin-minocycline impregnated catheters compared with chlorhexidine-silver sulfadiazine catheters.

Nitazoxanide (NTZ) is a 5-nitrothiazole therapeutic that is used to treat a wide variety of parasitic and anaerobic bacterial infections and is FDA approved for treatment of *Cryptosporidium parvum* and *Giardia intestinalis* infections in adults and children. The drug also shows efficacy against *Clostridium difficile* infections. Mechanistic studies have shown that NTZ is a potent inhibitor of pyruvate: ferredoxin oxidoreductase and therefore is active against all organisms (anaerobic bacteria and parasites) expressing this enzyme. Mechanistic studies revealed that the anionic form of the drug is biologically active and a proton abstraction mechanism has been proposed. Such a generic mechanism might account for the wide range of biological targets reported for this drug.

Mechanistic studies have shown that NTZ is a potent inhibitor of PFOR by interfering with the function of the thiamine pyrophosphate cofactor. The anion form of the drug abstracts a proton from the activated TPP complex and thereby blocks catalysis of pyruvate to acetyl CoA and $CO_2$. The protonated form of NTZ is biologically inactive. Staphylococcal species utilize pyruvate dehydrogenase and not PFOR to catalyze the oxidative decarboxylation of pyruvate. However, the chemical reactivity of NTZ might not be limited to the PFOR target as the drug has been shown to inhibit nitroreductases, protein disulfide bond isomerases and other targets.

Enteroaggregative *Escherichia coli* (EAEC) strains have emerged as a common cause of persistent diarrhea and malnutrition among children and HIV-infected persons. During infection, EAEC typically adheres to the intestinal mucosa via fimbrial adhesins that results in a characteristic aggregative pattern.

Infectious diarrheal diseases are the second highest global cause of morbidity and mortality, and repeated or prolonged episodes of diarrhea can stunt the growth of infected children and impair cognition. The World Health Organization has estimated that stunting affects approximately 147 million children in the developing world, where every child less than five years old suffers an average of three diarrheal episodes per year. Due to the morbidity burden of diarrheal disease, especially during early childhood, more effective therapies are expected to save many disability-adjusted life years.

EAEC, first identified and described as a diarrheagenic *E. coli* in 1987, has emerged as a leading cause of acute and persistent (≥14 days) diarrhea among children, AIDS patients, and international travelers in developing and industrialized countries. Around the world, EAEC accounts for 8-32% of acute diarrhea cases among infants and children and 20-30% of persistent diarrhea cases. Individuals most often contract infection via the fecal-oral route by consuming contaminated food and water or by practicing poor hygiene.

The clinical presentation of EAEC infection often consists of watery diarrhea, at times with passage of blood and mucus, but some infections are asymptomatic. This phenomenon is likely due to differences in both host susceptibility and strain heterogeneity. Patients often experience intestinal inflammation marked by elevated levels of fecal lactoferrin, and EAEC infection may perpetuate childhood malnutrition.

EAEC pathogenesis is complex and not fully understood, in large part due to the heterogeneity of strains. Generally, EAEC pathogenesis involves three stages: 1) adherence to the intestinal mucosa, mediated by aggregative adherence fimbriae (AAF); 2) biofilm formation on the surface of host enterocytes; and 3) release of EAEC toxins, elicitation of an inflammatory response, intestinal secretion, and mucosal toxicity, which results in microvillus vesiculation and epithelial cell extrusion.

Several virulence factors have been implicated in mucosal adherence and biofilm formation. Most important and best-studied is the master transcriptional regulator AggR, whose gene is located on a 60-65 MDa pAA plasmid present in many, but not all, strains of EAEC. AggR is activated in response to environmental cues such as low sodium, oxygen, pH and nutrients and controls the expression of several plasmid-encoded genes involved in fimbrial biogenesis, notably aafA (GenBank accession no. AF012835), which encodes for a major structural subunit of the AAF/II variant, expressed by the pathogenic strain 042. AAF/II fimbriae have been described as 5 nm in diameter, arranged in semirigid, filamentous bundles (7), and are thought to mediate adherence to the colonic mucosa and to polystyrene and glass surfaces. AggR also controls expression of other fimbrial genes (e.g., AAF/I, AAF/III) that are antigenically different, some of which can agglutinate erythrocytes or have other non-biofilm producing phenotypes.

Following adherence, EAEC produces a mucosal biofilm that promotes colonization and resists penetration of antimicrobials. The biofilm of strain 042 consists of thick aggregates of bacteria interspersed with void spaces, similar to other bacterial biofilms and characteristic of the heavy biofilm that forms over the epithelium during infection. Biofilm formation is mediated by AAF fimbriae whose expression involves two chromosomal genes, fis and yafK, which are activated by AggR. However, the genetic markers that characterize biofilm-producing strains and the clinical relevance of biofilm formation during infection remain unclear.

There is a long felt need in the art for new and improved antimicrobial agents. The present invention satisfies these needs.

SUMMARY OF THE INVENTION

The present invention discloses that the anion form of NTZ is the biologically active form and most of the drug is inactive below pH 6. Experiments were performed, to explore the possibility that modifications to the current drug might overcome these deficiencies. The present invention provides unexpected uses of NTZ and related compounds and also provides novel compounds, methods of preparing the compounds, and uses of the compounds. Various aspects and embodiments of the invention are described in further detail below.

The molecular formula of NTZ is $C_{12}H_9N_3O_5S$ and the molecular weight is 307.3. NTZ has the following structure:

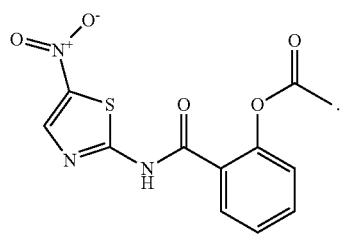

2-(acetyloxy)-N-(5-nitro-2-thiazolyl) benzamide

The present invention provides novel derivatives and analogues of NTZ and uses for these compounds.

In one embodiment, the present invention provides a compound of Formula (I):

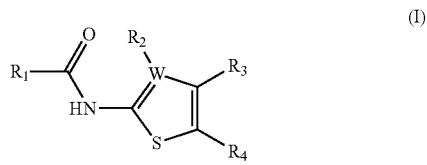

wherein:

$R_1$ and $R_3$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted);

$R_2$ and $R_4$ are selected from the group consisting of: H, acyl, alkyl, alkenyl, alkynyl, aryl, heteroaryl, nitro, amino acid sidechain, amino acid, carbonyl, carboxy (each group can be optionally substituted); and W is selected from $CH_2$, N;

or a pharmaceutically acceptable salt or prodrug thereof.

In one aspect, optional substitution of groups includes the groups as listed for the R groups of that formula. In another aspect, the optional substitution can include optional substitution with 1, 2, 3, or 4 groups where the substituent groups are independently H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

In one aspect, the compound of Formula I has the structure of a compound of Formula (I)(a):

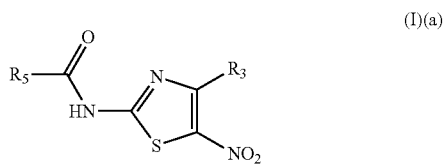

wherein:

$R_3$ and $R_5$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted);

or a pharmaceutically acceptable salt or prodrug thereof.

In one aspect, the compound of Formula I has the structure of a compound of Formula (I)(b):

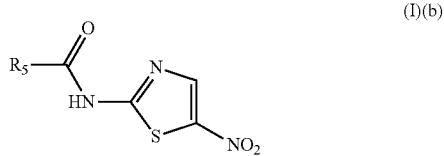

wherein:

$R_5$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid;

or a pharmaceutically acceptable salt or prodrug thereof.

In one aspect, a compound of the invention has Formula (I)(c):

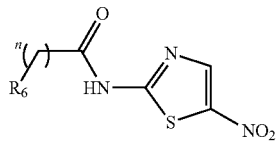

wherein:

R$_6$ is selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted); and n is selected from 0 to 8;

or a pharmaceutically acceptable salt or prodrug thereof.

In another aspect, a compound of the invention has Formula (I)(d):

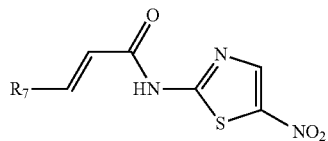

wherein:

R$_7$ is selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted); and or a pharmaceutically acceptable salt or prodrug thereof.

In yet another aspect, a compound of the invention has Formula (I)(e):

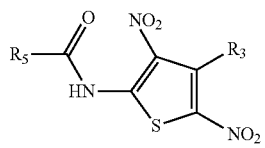

wherein:

R$_3$ and R$_5$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted);

or a pharmaceutically acceptable salt or prodrug thereof.

In a further aspect, a compound of the invention has Formula (I)(f):

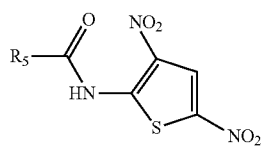

wherein:

R$_5$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid;

or a pharmaceutically acceptable salt or prodrug thereof.

In another aspect, a compound of the invention has Formula (I)(g):

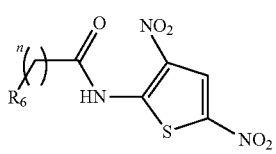

wherein:

R$_6$ is selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted); and n is selected from 0 to 8;

or a pharmaceutically acceptable salt or prodrug thereof.

In yet another aspect, a compound of the invention has Formula (I)(h):

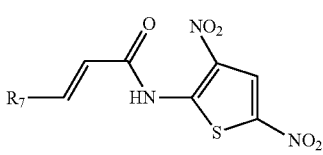

wherein:

R$_7$ is selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted);

or a pharmaceutically acceptable salt or prodrug thereof.

In one embodiment, the present invention provides a compound of Formula (II):

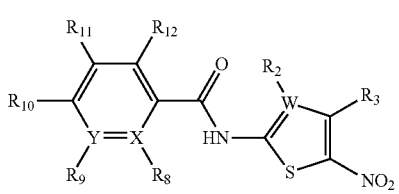

(II)

wherein:

$R_3$ and $R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted) and $R_2$ is selected from the group consisting of: H, acyl, alkyl, alkenyl, alkynyl, aryl, heteroaryl, nitro, amino acid sidechain, amino acid, carbonyl, carboxy (each group can be optionally substituted); and W is selected from CH$_2$, N; and X and Y are each selected from CH and N; and Z is selected from CH$_2$, O, S, N; and n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and each group can be optionally substituted;

or a pharmaceutically acceptable salt or prodrug thereof.

In one aspect, a compound of Formula II has a structure of a compound of Formula (II)(a):

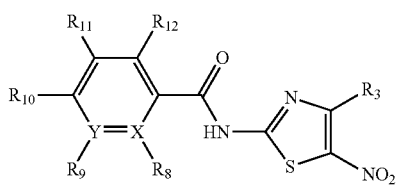

(II)(a)

wherein:

$R_3$ and $R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted);

X and Y are each selected from CH and N;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and each group can be optionally substituted;

or a pharmaceutically acceptable salt or prodrug thereof.

In one aspect, a compound of the invention comprises a structure of Formula (II)(b):

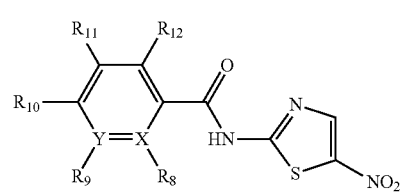

(II)(b)

wherein:

$R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted);

X and Y are each selected from CH and N;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and each group can be optionally substituted;

or a pharmaceutically acceptable salt or prodrug thereof.

In another aspect, the invention provides a compound of Formula (II)(c):

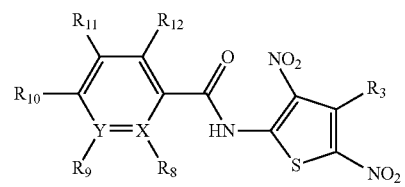

(II)(c)

wherein:

$R_3$ and $R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted);

X and Y are each selected from CH and N;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and each group can be optionally substituted;

or a pharmaceutically acceptable salt or prodrug thereof.

In yet another aspect, the invention provides a compound of Formula (II)(d):

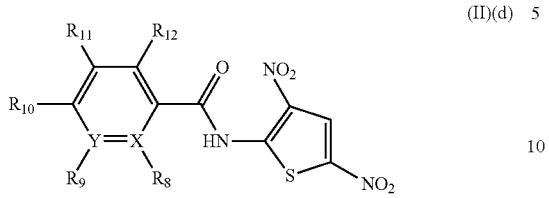

(II)(d)

wherein:

$R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted);

X and Y are each selected from CH and N;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and wherein each group can be optionally substituted;

or a pharmaceutically acceptable salt or prodrug thereof.

In one embodiment, the invention provides a compound of Formula (III):

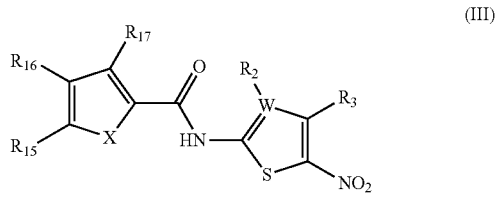

(III)

wherein:

$R_3$ and $R_{15}$-$R_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid "—Z(CH$_2$)$_n$NR$_{13}$R$_{14}$" (each group can be optionally substituted);

$R_2$ is selected from the group consisting of: H, acyl, alkyl, alkenyl, alkynyl, aryl, heteroaryl, nitro, amino acid sidechain, amino acid, carbonyl, and carboxy, wherein each group can be optionally substituted; W is selected from CH$_2$, N;

X is selected from O, S, NH and NCH$_3$;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted;

or a pharmaceutically acceptable salt or prodrug thereof.

In one aspect, a compound of Formula (III) has a structure of a compound of Formula (III)(a):

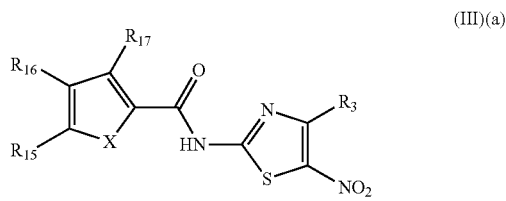

(III)(a)

wherein:

$R_3$ and $R_{15}$-$R_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid "—Z(CH$_2$)$_n$NR$_{13}$R$_{14}$", wherein each group can be optionally substituted;

X is selected from O, S, NH and NCH$_3$;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted;

or a pharmaceutically acceptable salt or prodrug thereof.

In another aspect, the invention provides a compound of Formula (III)(b):

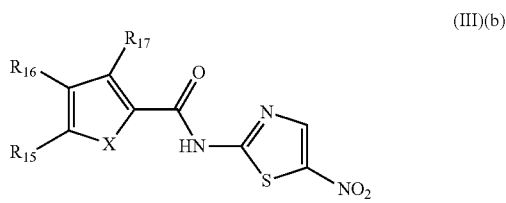

(III)(b)

wherein:

$R_{15}$-$R_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid "—Z(CH$_2$)$_n$NR$_{13}$R$_{14}$", wherein each group can be optionally substituted;

X is selected from O, S, NH and NCH$_3$;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted;

or a pharmaceutically acceptable salt or prodrug thereof.

In yet another aspect, the invention provides a compound of Formula (III)(c):

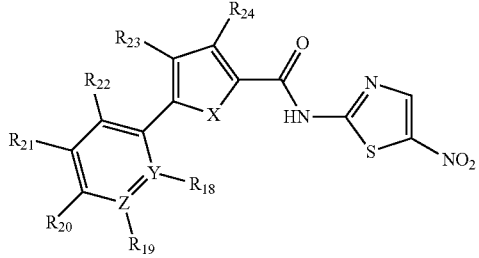

(III)(c)

wherein:

R$_{18}$-R$_{24}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted;

X is selected from O, S, NH and NCH$_3$; and

Y and Z are each independently selected from CH and N;

or a pharmaceutically acceptable salt or prodrug thereof.

In yet another aspect, the invention provides a compound of Formula (III)(d):

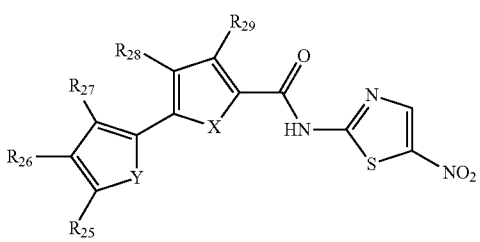

(III)(d)

wherein:

R$_{25}$-R$_{29}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X and Y are each independently selected from O, S, NH and NCH$_3$;

or a pharmaceutically acceptable salt or prodrug thereof.

In a further aspect, the invention provides a compound of Formula (III)(e):

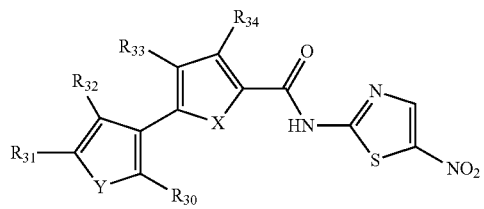

(III)(e)

wherein:

R$_{30}$-R$_{34}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X and Y are each independently selected from O, S, NH and NCH$_3$;

or a pharmaceutically acceptable salt or prodrug thereof.

In yet another aspect, the invention provides a compound of Formula (III)(f):

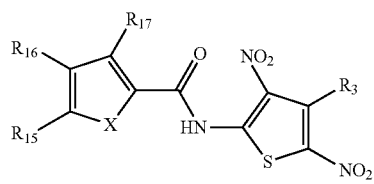

(III)(f)

wherein:

R$_3$ and R$_{15}$-R$_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid "—Z(CH$_2$)$_n$NR$_{13}$R$_{14}$", wherein each group can be optionally substituted;

X is selected from O, S, NH and NCH$_3$;

Z is selected from CH$_2$, O, S, N;

n is selected from 1 to 6; and

R$_{13}$ and R$_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted;

or a pharmaceutically acceptable salt or prodrug thereof.

In another aspect, the invention provides a compound of Formula (III)(g):

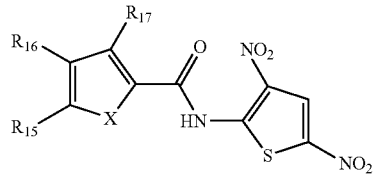

(III)(g)

wherein:

R$_{15}$-R$_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid "—Z(CH$_2$)$_n$NR$_{13}$R$_{14}$", wherein each group can be optionally substituted;

X is selected from O, S, NH and NCH$_3$;

Z is selected from CH$_2$, O, S, N;

n is selected from 1 to 6; and

R$_{13}$ and R$_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted; or a pharmaceutically acceptable salt or prodrug thereof.

In another aspect, the invention provides a compound of Formula (III)(h):

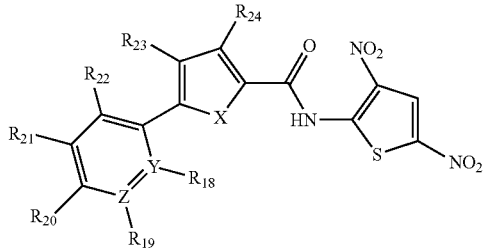

(III)(h)

wherein:

$R_{18}$-$R_{24}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted;

X is selected from O, S, NH and $NCH_3$; and

Y and Z are each selected from CH and N;

or a pharmaceutically acceptable salt or prodrug thereof.

In yet another aspect, the invention provides a compound of Formula (III)(i):

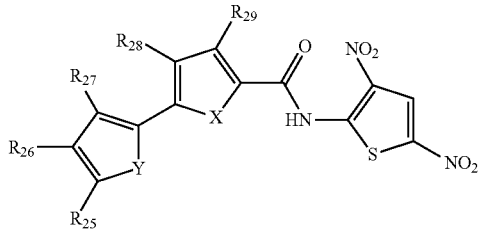

(III)(i)

wherein:

$R_{25}$-$R_{29}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X and Y are each independently selected from O, S, NH and $NCH_3$;

or a pharmaceutically acceptable salt or prodrug thereof.

In a further aspect, the invention provides a compound of Formula (III)(j):

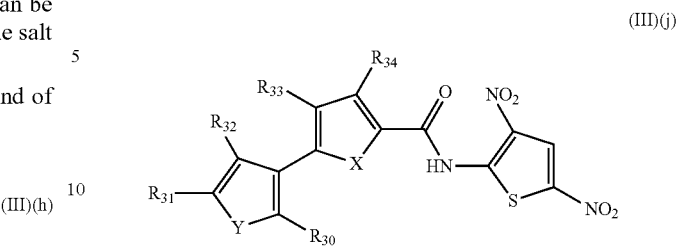

(III)(j)

wherein:

$R_{30}$-$R_{34}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X and Y are each independently selected from O, S, NH and $NCH_3$;

or a pharmaceutically acceptable salt or prodrug thereof.

In one embodiment, the invention provides a compound of Formula (IV):

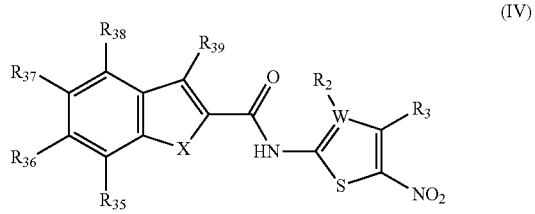

(IV)

wherein:

$R_3$ and $R_{35}$-$R_{39}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted, and $R_2$ is selected from the group consisting of: H, acyl, alkyl, alkenyl, alkynyl, aryl, heteroaryl, nitro, amino acid sidechain, amino acid, carbonyl, and carboxy, wherein each group can be optionally substituted;

W is selected from $CH_2$, and N; and

X is selected from O, S, NH and $NCH_3$;

or a pharmaceutically acceptable salt or prodrug thereof.

In one aspect, a compound of Formula IV comprises a compound of Formula (IV)(a):

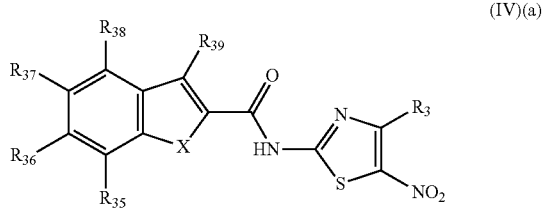

(IV)(a)

wherein:

$R_3$ and $R_{35}$-$R_{39}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$.

or a pharmaceutically acceptable salt or prodrug thereof.

In another aspect, the invention provides a compound of Formula (IV)(b):

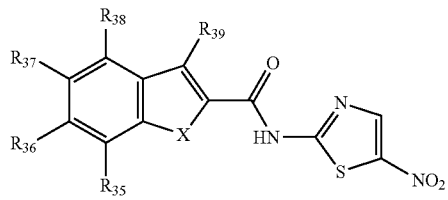

(IV)(b)

wherein:

R$_{35}$-R$_{39}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In a further aspect, the invention provides a compound of Formula (IV)(c):

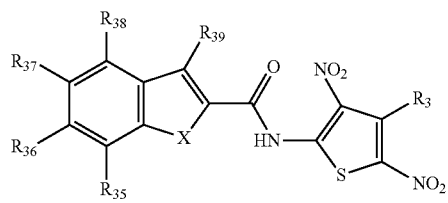

(IV)(c)

wherein:

R$_3$ and R$_{35}$-R$_{39}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In yet a further aspect, the invention provides a compound of Formula (IV)(d):

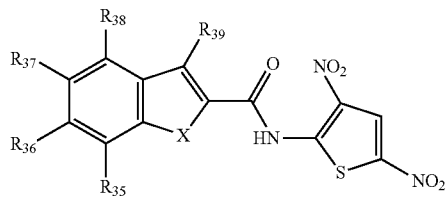

(IV)(d)

wherein:

R$_{35}$-R$_{39}$ are each independently selected from the group consisting of: H, halogen, hydroxy, acyl, alkyl, alkenyl, alky-nyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In one embodiment, the present invention provides a compound of Formula (V):

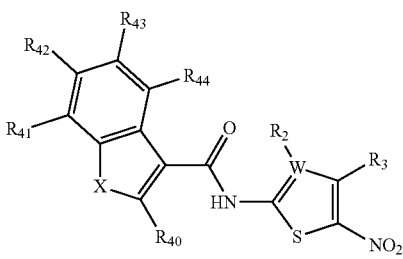

(V)

wherein:

R$_3$ and R$_{40}$-R$_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted, and R$_2$ is selected from the group consisting of: H, acyl, alkyl, alkenyl, alkynyl, aryl, heteroaryl, nitro, amino acid sidechain, amino acid, carbonyl, and carboxy, wherein each group can be optionally substituted;

W is selected from CH$_2$, and N; and

X is selected from O, S, NH and NCH$_3$;

or a pharmaceutically acceptable salt or prodrug thereof.

In one aspect, a compound of Formula V comprises a compound of Formula (V)(a):

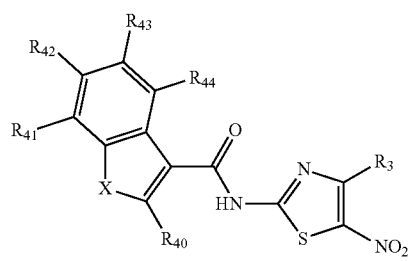

(V)(a)

wherein:

R$_3$ and R$_{40}$-R$_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In a further aspect, the invention provides a compound of Formula (V)(b):

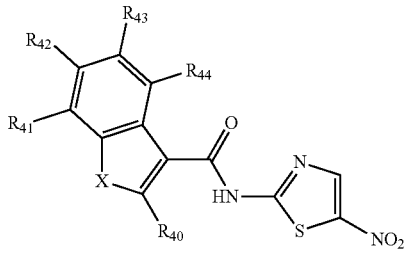

(V)(b)

wherein:

$R_{40}$-$R_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In a further aspect, the invention provides a compound of Formula (V)(c):

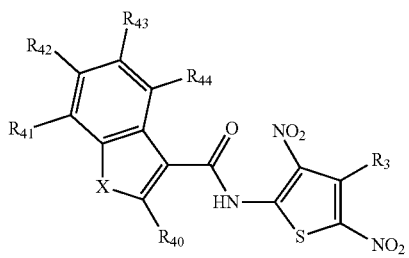

(V)(c)

wherein:

$R_3$ and $R_{40}$-$R_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In another aspect, the invention provides a compound of Formula (V)(d):

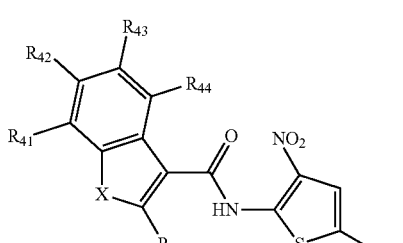

(V)(d)

wherein:

$R_{40}$-$R_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In one embodiment, the invention provides a compound of Formula (VI):

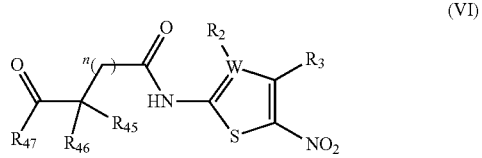

(VI)

wherein:

$R_3$ and $R_{45}$-$R_{47}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted) and $R_2$ is selected from the group consisting of: H, acyl, alkyl, alkenyl, alkynyl, aryl, heteroaryl, nitro, amino acid sidechain, amino acid, carbonyl, and carboxy, wherein each group can be optionally substituted;

W is selected from CH$_2$, and N;

n is selected from 0 to 2;

or a pharmaceutically acceptable salt or prodrug thereof.

In one aspect, a compound of Formula VI comprise a compound of Formula (VI)(a):

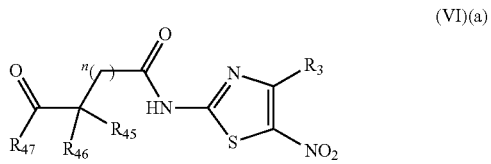

(VI)(a)

wherein:

$R_3$ and $R_{45}$-$R_{47}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and n is selected from 0 to 2;

or a pharmaceutically acceptable salt or prodrug thereof.

In yet another aspect, the invention provides a compound of Formula (VI)(b):

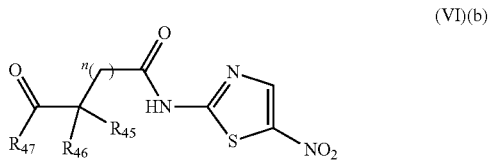

(VI)(b)

wherein:

R_{45}-R_{47} are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and n is selected from 0 to 2;

or a pharmaceutically acceptable salt or prodrug thereof.

In a further aspect, the invention provides a compound of Formula (VI)(c):

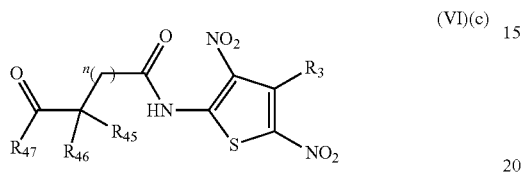

(VI)(c)

wherein:

$R_3$ and $R_{45}$-$R_{47}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and n is selected from 0 to 2;

or a pharmaceutically acceptable salt or prodrug thereof.

In yet another aspect, the invention provides a compound of Formula (VI)(d):

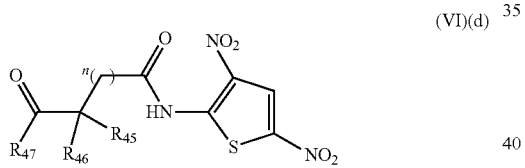

(VI)(d)

wherein:

$R_{45}$-$R_{47}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted); and n is selected from 0 to 2;

or a pharmaceutically acceptable salt or prodrug thereof.

For all compounds of the invention, in one aspect, optional substitution of groups includes the groups as listed for the R groups of that formula. In another aspect, the optional substitution can include optional substitution with 1, 2, 3, or 4 groups where the substituent groups are independently H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

In one aspect, the present invention provides compositions which include, but are not limited to, aliphatic derivatives of 2-amino-5-nitrothiazole, aliphatic amine analogues of 2-amino-5-nitrothiazole, amino acid analogues of 2-amino-5-nitrothiazole, anthranilic analogues of 2-amino-5-nitrothiazole, pyridine analogues of 2-amino-5-nitrothiazole, indole analogues of 2-amino-5-nitrothiazole, carboxylic acid analogues of 2-amino-5-nitrothiazole, dimer-like analogues of 2-amino-5-nitrothiazole, halide analogues of 2-amino-5-nitrothiazole, monosubstituted analogues of 2-amino-5-nitrothiazole, disubstituted analogues of 2-amino-5-nitrothiazole, furan analogues of 2-amino-5-nitrothiazole, thiophene analogues of 2-amino-5-nitrothiazole, amide isosteres of 2-amino-5-nitrothiazole, analogues of 2-amino-4-chloro-5-nitrothiazole, and analogues of 2-amino-3,5-dinitrothiophene, and derivatives and analogues thereof.

In one aspect, compounds of the invention include, but are not limited to, the following exemplary compounds, as further described in the examples:

VPC16a1007

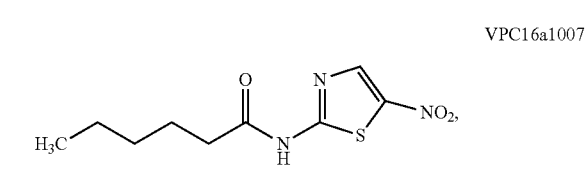

VPC161219

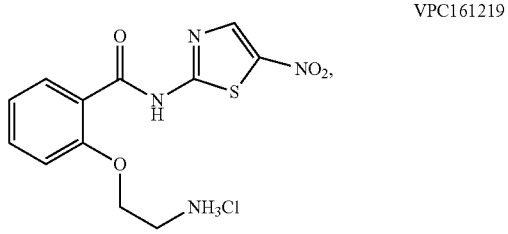

VPC162134

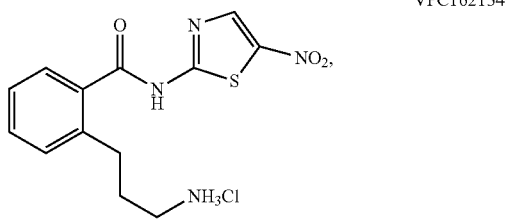

VPC162125

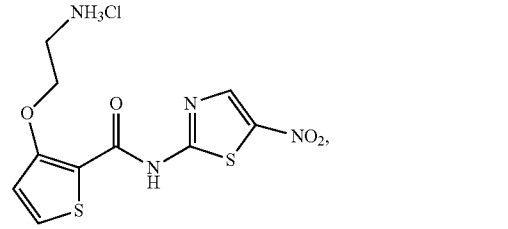

VPC16a1028

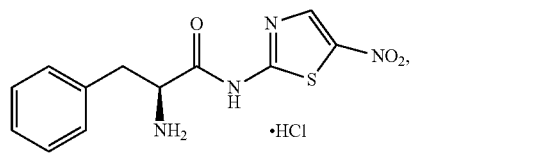

VPC162047

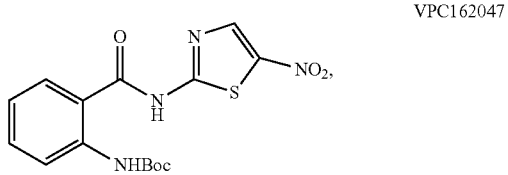

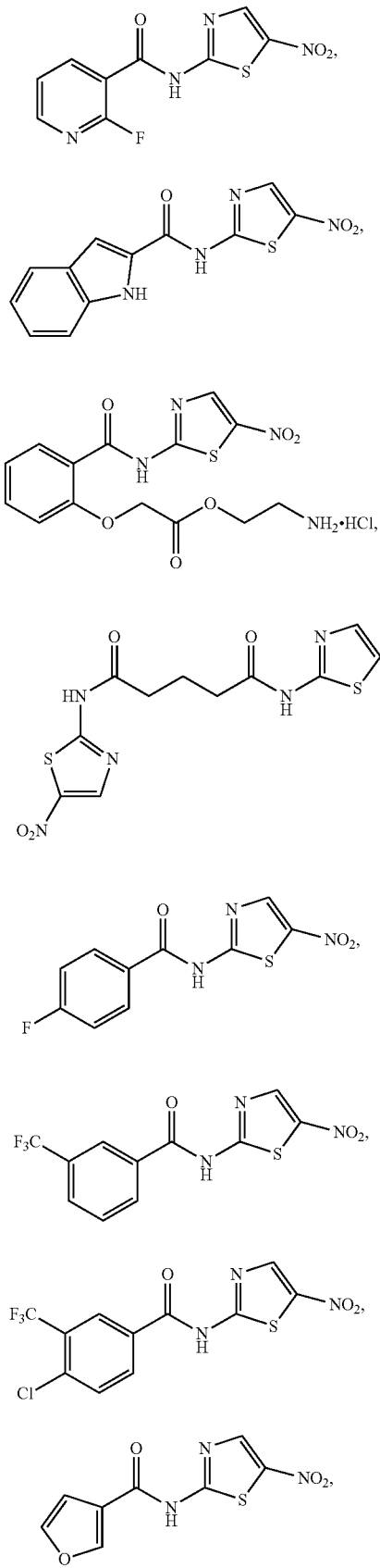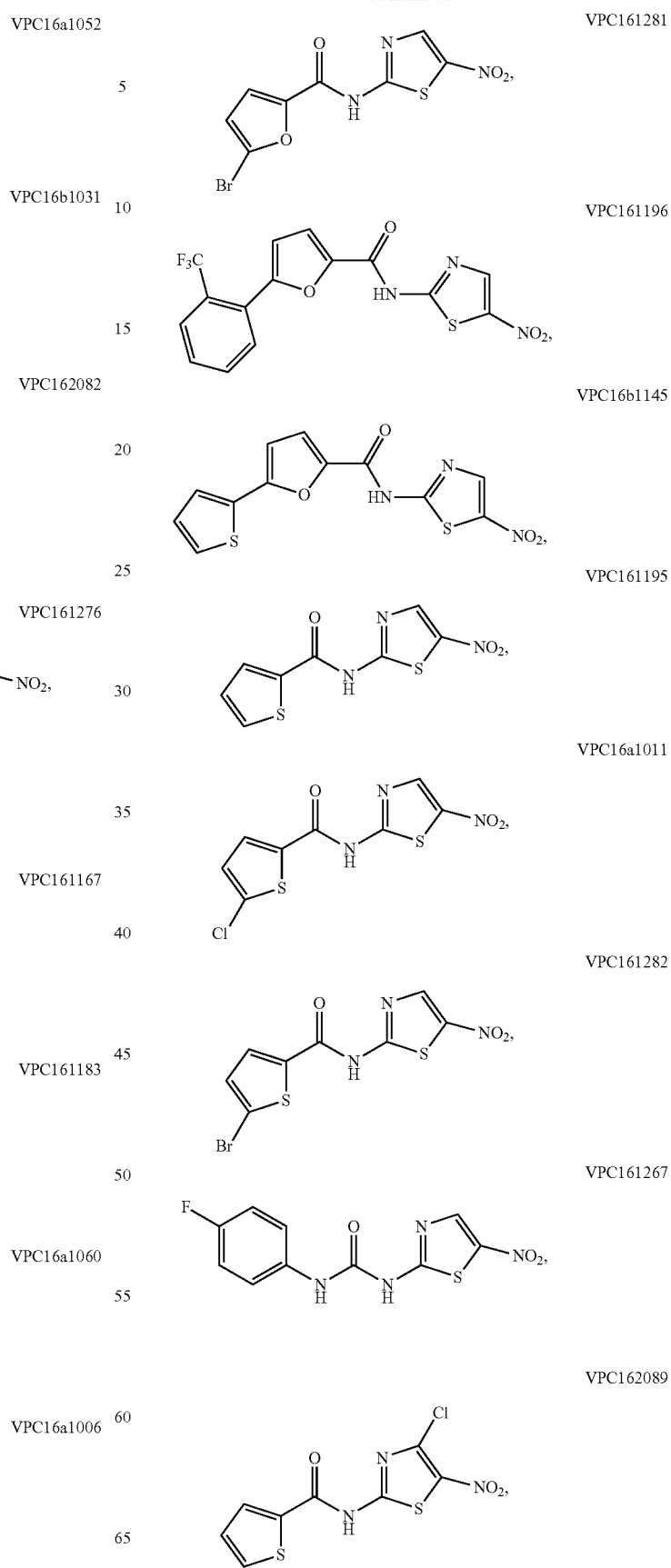

-continued

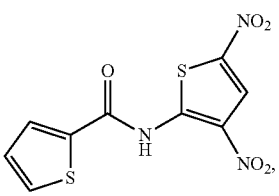
VPC16b1093

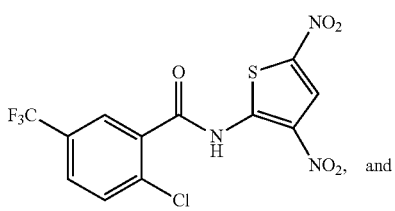
VPC16b2026

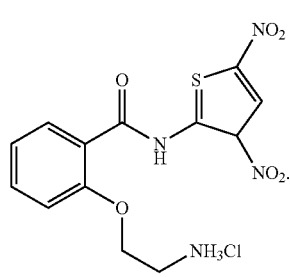
VPC162031

The present invention further provides pharmaceutical compositions comprising at least one compound of the invention. The pharmaceutical compositions are useful, for example, for preventing or treating infections as described herein by administering a pharmaceutical composition comprising an effective amount of at least one compound of the invention.

The compounds of the present invention are useful for targeting microorganisms other than just the ones described in the Examples. The present invention encompasses all organisms for which the nitrothiazolide compounds of the invention are effective. In one aspect, the present invention encompasses all microorganisms that contain PFOR (pyruvate ferredoxin oxidoreductase) and KFOR (2 ketoglutarate oxidoreductase) and related enzymes. In another aspect, the compounds of the invention are useful against all of the anaerobic species of bacteria including, but not limited to, Bacteroides and Clostridium, exemplified by B. fragilis, and C. difficile and C. perfringens.

The compounds and methods of the present invention are also useful against the Epsilon Proteobacteria, including all genera and species. Examples include, but are not limited to, Helicobacter pylori and Campylobacter jejuni.

The compounds and methods of the present invention are also useful against anaerobic parasites expressing PFOR including, but not limited to, Entamoeba histolytica, Giardia intestinalis, and Trichomonas vaginalis.

The compounds and methods of the present invention further have pilicide indications. The compounds of the present invention can inhibit the assembly of fimbriae (pili) that utilize the chaperone usher pathway of assembly that includes AafA pili of EAEC E. coli strains and urogenic UPEC strains that produce Type I fimbriae.

In another aspect of the invention, the present compounds are useful against Salmonella, Shigella, Klebsiella, and other members of the Enterobacteriaceae.

In yet another aspect of the invention, the present compounds are useful against Gram positive bacteria, such as by inhibition of biofilm production and inhibition of attachment to a surface. In one aspect, the bacteria are Staphylococcus epidermidis and S. aureus.

In a further aspect, compounds of the invention are bactericidal against Gram positive bacteria and Mycobacteria, including M. tuberculosis.

It is disclosed herein that Amixin, a bioavailable derivative of nitazoxanide, has demonstrated antiviral activity against hepatitis C, with predicted efficacy for hepatitis B and Influenza A and B.

In one aspect, antimicrobial agents of the invention that inhibit assembly or function of fimbrial filaments are useful for preventing and treating infection.

In one aspect, a compound of the invention inhibits biofilm formation. In one aspect, compounds of the invention are useful for inhibiting biofilm formation on surfaces. In one aspect, the surface is in or on an entity such as an animal. In another aspect, the surface is, for example, a catheter surface. In one aspect, a compound of the invention inhibits attachment to a surface. In one aspect, the surface is that of a catheter and a compound of the invention inhibits bacterial attachment to the catheter. In one aspect, the microbes are staphylococcal. In another aspect, the microbes are EAEC. In one aspect, the compounds of the invention are useful for inhibiting biofilm formation by bacteria that have already attached to a surface.

In one aspect, NTZ, TIZ, AMIX, and other compounds of the invention inhibit microbial growth in aerobic conditions. In one aspect, NTZ, TIZ, AMIX, and other compounds of the invention inhibit microbial growth and may affect expression or function of Aap in promoting aggregation. In one aspect, the microbe is a staphylococcus bacteria. In one aspect, the staphylococcus is S. epidermidis.

In one aspect, NTZ inhibits microbial hemagglutination of erythrocytes by AafA pili of EAEC. In one aspect, NTZ inhibits hemagglutination by blocking assembly of AafA fimbriae. Therefore, the present invention encompasses methods of inhibiting EAEC biofilm formation by inhibiting filament assembly. Furthermore, the present invention also provides compositions and methods for use as an anti-diarrheal.

In one aspect, bacteria susceptible to compounds of the invention include, but are not limited to, S. epidermidis, C. difficile, H. pylori, C. jejuni, MRSA, E. coli, and Mycobacterium species.

The present invention is also useful for preventing and treating infections comprising administering a pharmaceutical composition comprising an effective amount of a useful compound of the invention and a pharmaceutically-acceptable carrier.

The compounds of the invention can be administered or used with other drugs and antimicrobial agents.

The present invention further provides kits. Kits of the invention comprise at least one compound of the invention and an instructional material for the use thereof, and optionally an applicator.

BRIEF DESCRIPTION OF THE DRAWINGS

FIG. 32 (A and B). Comparison of Amixin with other anti-parasitic drugs for efficacy in treating amoebic dysentery in a mouse infection model. A (comprising eight panels; FIGS. 32-A1 to 32-A8). Comparison of various drugs on *E. histolytica* cell counts showing that Amixin is superior to nitazoxanide based on MIC. The eight panels provide results for Tinidazole, Amixin219, Metronidazole, Nitazoxanide, Pyrvinium Pamoate, Iodoquinol, Emetine, and Chloroquine (FIGS. 32-A1 to 32-A8). B (comprising 2 panels—32B1 and 32B2). A comparison of prevention rates for the various drugs administered orally (FIG. 32B1) or parenterally (FIG. 32B2)

Figure 1:
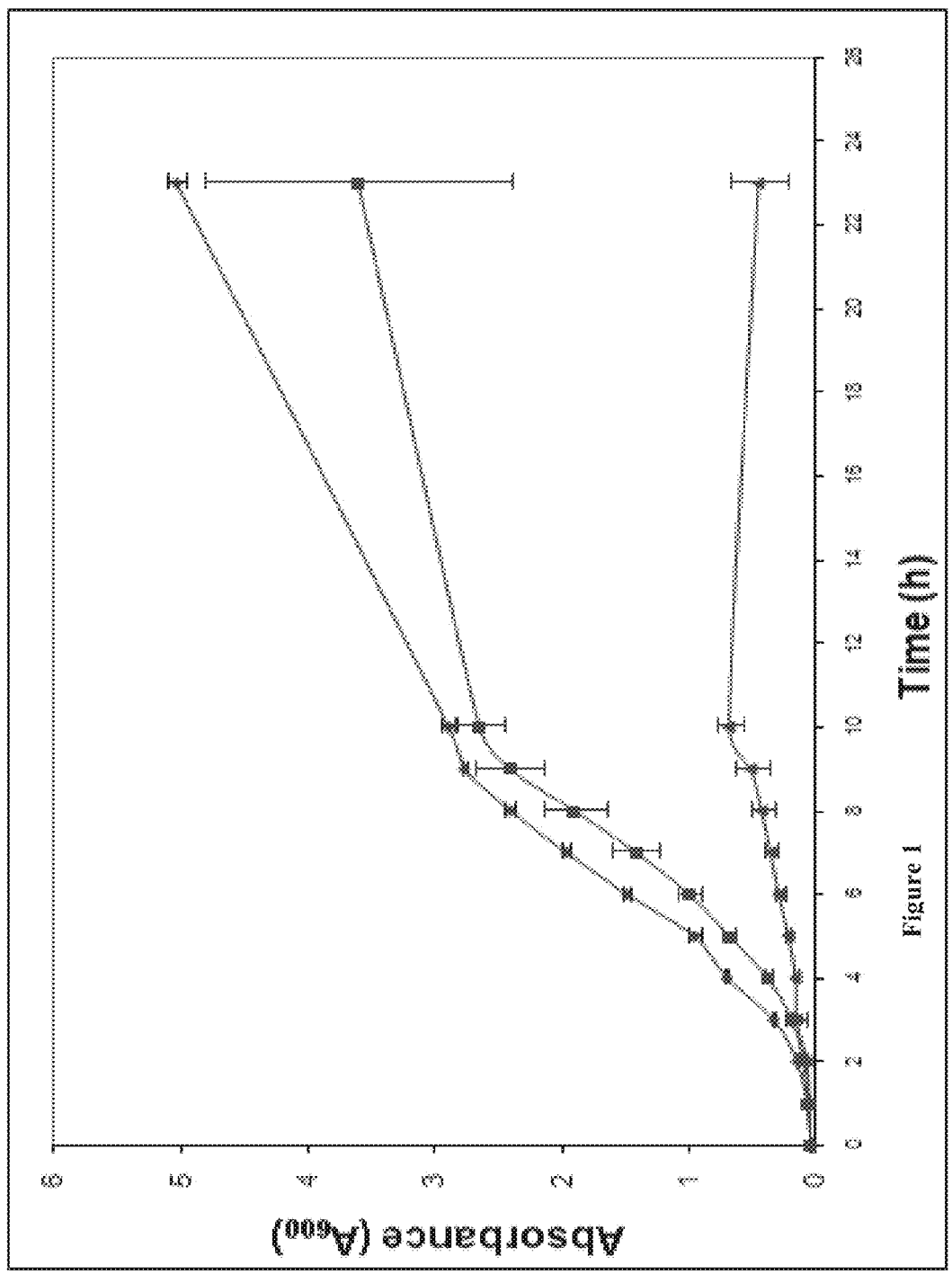
FIG. 1. NTZ inhibition of aerobic growth of S. epidermidis. Bacteria were grown in TSB medium with shaking at 37° C. in the presence of no NTZ ♦, 10 mg/ml (■) and 25 mg/ml (▲)

in advance and indicating equivalence between Amixin and NTZ in this assay. ** pval=0.001 (Fisher's Exact) vs PBS; * pval=0.02 (Fisher's Exact) vs PBS; ‡pval=0.02 (Fisher's Exact) vs Metronidazole.

DETAILED DESCRIPTION

Abbreviations and Acronyms

AAF—aggregative adherence fimbriae
Aap—accumulation associated protein
AMIX—amixin (TIZ-ethylamine; compound VPC161219)
CRBSI—catheter-related bloodstream infections
CoNS—Coagulase-negative staphylococci
EAEC—Enteroaggregative *Escherichia coli*
HA—Hemagglutination
ICS—Infection-causing strains
KFOR—2 ketoglutarate oxidoreductase
MIC—minimal inhibiting concentration
MRSA—Methicillin-resistant *Staphylococcus aureus*
NTZ—nitazoxanide
PFOR—pyruvate ferredoxin oxidoreductase
RFLP—restriction fragment length polymorphism
TIZ—tizoxanide
TSB or TSA—Trypticase soy broth or agar

DEFINITIONS

In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

The term "amebiasis", as used herein, refers to the disease caused by *E. histolytica*. The term "amebiasis" is used interchangeably with the term "amoebiasis". The symptoms often are quite mild and can include loose stools, stomach pain, and stomach cramping. Amebic dysentery is a severe form of amebiasis associated with stomach pain, bloody stools, and fever. Rarely, *E. histolytica* invades the liver and forms an abscess. Even less commonly, it spreads to other parts of the body, such as the lungs or brain.

As used herein, an "analog", or "analogue" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

A "compound," as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

As used herein, "homology" is used synonymously with "identity."

The term "inhibit," as used herein, refers to the ability of a compound of the invention to reduce or impede a described function, such as having inhibitory sodium channel activity. Preferably, inhibition is by at least 10%, more preferably by at least 25%, even more preferably by at least 50%, and most preferably, the function is inhibited by at least 75%. The terms "inhibit", "reduce", and "block" are used interchangeably herein.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "modulate", as used herein, refers to changing the level of an activity, function, or process. The term "modulate" encompasses both inhibiting and stimulating an activity, function, or process.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pilicide", as used herein, refers to small molecule inhibitors of filament biogenesis.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "subject" of diagnosis or treatment is a mammal, including a human, as well as other organisms of interest.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

As used herein, the term "wound" relates to a physical tear, break, or rupture to a tissue or cell layer. A wound may occur by any physical insult, including a surgical procedure or as a result of a disease, disorder condition.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" typically refers to from zero to four substituents, wherein the substituents are each independently selected. Each of the independently selected substituents may be the same or different than other substituents. For example, the substituents of an R group of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one or more substituents. The term ($C_5$-$C_8$ alkyl)aryl refers to any aryl group which is attached to the parent moiety via the alkyl group.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable."

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

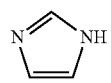

is understood to represent a mixture of the structures:

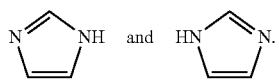

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

Embodiments

As described herein, the compositions of the present invention comprise, as an active agent, compounds having the structure of any of the formulas disclosed herein in a pharmaceutically acceptable form. If desired, the compositions may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

The values provided herein for radicals, substituents, and ranges, are for illustration only; they do not exclude other defined values or other values within defined ranges for the radicals and substituents. The disclosed compounds include compounds of the specific Formulas recited herein having any combination of the exemplary values, preferred values, and more preferred values described herein.

Processes for preparing compounds of any of the formulas of the invention or for preparing intermediates useful for preparing compounds of any of the formulas of the invention are provided as further embodiments of the invention. Intermediates useful for preparing compounds of formula I are also provided as further embodiments of the invention.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Processes for preparing compounds of any of the formulas of the invention are provided as further embodiments of the invention and are illustrated by the following procedures in which the meanings of the generic radicals are as given above unless otherwise qualified.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of any of the formulas of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

It will be appreciated that compounds of the invention can be administered using various kinds of delivery systems and media. Furthermore, compounds of the invention can be administered in combination with other therapeutic agents and compounds and can be used with other kinds of treatments.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, when the active ingredient needs to enter circulation and be delivered via blood, the active ingredient, in one embodiment, should be administered to achieve peak plasma concentrations of the active compound of from about 0.5 to about 75 μM, preferably, about 1 to 50 μm, most preferably, about 2 to about 30 μm. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In another embodiment, a formulation of the invention can be impregnated into a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

Non-synthetic matrix proteins like collagen, glycosaminoglycans, and hyaluronic acid, which are enzymatically digested in the body, are useful for delivery (see U.S. Pat. Nos. 4,394,320; 4,472,840; 5,366,509; 5,606,019; 5,645,591; and 5,683,459) and are suitable for use with the present invention. Other implantable media and devices can be used for delivery of the compounds of the invention in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The compounds of the present invention can be further combined with growth factors, nutrient factors, pharmaceuticals, calcium-containing compounds, anti-inflammatory agents, antimicrobial agents, or any other substance capable of expediting or facilitating bone or tissue growth, stability, and remodeling.

The compositions of the present invention can also be combined with inorganic fillers or particles. For example for use in implantable grafts the inorganic fillers or particles can be selected from hydroxyapatite, tri-calcium phosphate, ceramic glass, amorphous calcium phosphate, porous ceramic particles or powders, mesh titanium or titanium alloy, or particulate titanium or titanium alloy.

Examples of other antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

In one embodiment, the compounds of the invention can first be encapsulated into microcapsules, microspheres, microparticles, microfibers, reinforcing fibers and the like to facilitate mixing and achieving controlled, extended, delayed and/or sustained release and combined other agents or drugs. Encapsulating the biologically active agent can also protect the agent against degradation during formation of the composite of the invention.

In another embodiment of the invention, the compound is controllably released into a subject when the composition of the invention is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising a compound identified in the invention and an instructional material which describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

Other useful techniques that can be practiced with the present invention can be found in the art, such as in Rossignol et al. (WO2007081974).

EXAMPLES

The results described below demonstrate that nitazoxanide was made to be water soluble and at the same time it had greatly improved its pKa. In direct enzyme assays the new compound is more inhibitory than is NTZ.

Also demonstrated are new lead compounds that have been synthesized. Some of these new lead compounds are of the benzothiaphene-nitrothiazolide class with demonstrated antimicrobial action against members of this pathogen group.

Example 1

Biofilms

Nitazoxanide Inhibits Biofilm Formation by *Staphylococcus epidermidis*

One of the original communications on the spectrum of action of NTZ indicated that the drug was active against *Staphylococcus aureus* only under anaerobic conditions (6). In the present study we explored the inhibitory nature of NTZ against strains of *S. aureus* and *S. epidermidis*. Our studies show that NTZ is inhibitory to aerobic growth of staphylococcal species including MRSA strains of *S. aureus* (MIC 8-16 µg/m), but at sub-MIC levels blocks biofilm formation by *S. epidermidis*. The inhibition of biofilm production by NTZ can be reversed by addition of 10 µM zinc chloride to the medium. Because accumulation of S. epidermidis to surfaces and aggregation in liquid is mediated by $Zn^{2+}$-dependent accumulation associated proteins (Aap) through G5 (zinc-zipper) dimerization domain repeats (4); it is likely that NTZ affects expression or function of this protein.

Materials and Methods

Bacterial Strains and Growth Conditions.

Bacterial strains used in this study are listed in Table 1. Unless otherwise specified, strains were grown in Trypticase soy broth or agar (TSB or TSA, respectively) at 37° C. with shaking for liquid cultures. All strains were stored at −80° C. in 15% glycerol.

Identification of S. epidermidis Isolates from Catheter Related Bloodstream Infections.

Infection-causing strains (ICS) of S. epidermidis were obtained from individuals with a long-term intravenous catheter and a CRBSI, defined by more than one blood culture and a concomitant catheter tip culture with CoNS. Medical records for these patients were reviewed to confirm that the patient exhibited clinical manifestations of a systemic inflammatory response syndrome, the absence of another focus of infection, and resolution of SIRS within 48 h of catheter removal.

Species identification was performed by one of two methods: either by using the API Staph system (BioMerieux, Durham, N.C.), according to the manufacturer's instructions, or by genetic testing. The latter was performed by a combination of two methods: PCR identification of the S. epidermidis specific gene serp0107 (16) and PCR restriction fragment length polymorphism (RFLP) analysis of the Staphylococcus tuf gene (15). Genomic DNA was prepared by suspending an individual bacterial colony in 20 µl of lysis buffer containing 0.25% SDS and 0.05 N NaOH, incubating at 95° C. for 5 min, and then adding 180 µl of sterile $dH_2O$. After centrifugation for 1 min at 16,100×g to sediment the debris, the supernatant was used as template DNA for PCR. Samples were kept at −20° C. for long-term storage. PCRs were carried out with a Mastercycler Gradient thermal cycler (Eppendorf, Westbury, N.Y.). PCR amplification of serp0107 was performed as previously described (16) using the primers listed in Table 1. The presence of a single 581-bp product on 1% agarose gel electrophoresis was consistent with a species identification of S. epidermidis. To confirm the identification, RFLP analysis of the Staphylococcus tuf gene PCR product was performed, using the method described by Kontos and colleagues (15). Briefly, PCR amplification of the tuf gene yielded a 370-bp amplicon that was confirmed by gel electrophoresis on a 2% agarose gel (15). The product was extracted using a QIAquick gel extraction kit (QIAGEN, Valencia, Calif.), according to the manufacturer's instructions, and subjected to the BstZ17I, BseNI, and MseI restriction enzyme digestion. The resulting fragment(s) were resolved by electrophoresis through a 3% agarose gel containing ethidium bromide at 50V for 45 min and visualized under UV light.

Digestion of the tuf gene amplicon of S. epidermidis produces two fragment using BstZ17I (243- and 127-bp), three fragment using BseNI (246-, 86-, and 38-bp), and no restriction using MseI (single 370-bp product). The presence of these fragments positively identified the strain as S. epidermidis. For both the serp0107 amplification and tuf RFLP analysis, S. epidermidis strains ATCC 12228 and 9142 served as positive controls while Staphylococcus haemolyticus F16942, S. aureus 8325, and water alone served as negative controls. ICS S. epidermidis strains were identified when (a) the case met the clinical definition of a CRBSI, (b) concomitant blood and catheter culture isolates were both positively identified as S. epidermidis, and (c) the blood and catheter isolates had congruent antibiotic susceptibility patterns. The study protocol was approved by the institutional review board of the University of Virginia Health System.

Determination of MIC—

Minimal inhibitory concentration testing of NTZ was done in sterile round bottom 96 well microtiter polystyrene plates (Corning Inc., Corning, N.Y.) by microdilution. Tizoxanide TIZ (deacetylated form of NTZ), denitro-NTZ (TIZ without 5-nitro group) and amoxanide AMIX (TIZ-ethylamine) were also tested. Bacteria were grown overnight and suspended in fresh TSB to an $OD_{600}$ of 0.01 and 100 µl were dispensed into wells with the first well containing 200 µl. NTZ and other antibiotics (DMSO control) were added to well one and serially diluted from 32 µg/ml. All compounds were tested in triplicate and plates were read visually or with a plate reader (Molecular Devices) at 8, 12 and at 24 h. MIC was determined as the first well in which no visible bacterial growth was noted relative to controls. Drug effects on aerobic growth were determined in 125 ml flasks containing 25 ml of TSB medium and following inoculation (detailed above), flasks were on a gyrorotary shaker (200 rpm) at 37° C. Final concentrations of NTZ were 0, 10 and 25 µg/m and samples were removed at hourly intervals and absorbance determined at 600 nm.

Biofilm Determinations.

Staphylococcal strains were cultured overnight in TSB at 37° C. with shaking, diluted in fresh medium to an $OD_{600}$ of 0.01 and 200 µl was dispensed into sterile flat bottom polystyrene 96 well microtiter plates (Costar 3596, Corning Inc.). NTZ, TIZ and denitro-NTZ were tested at different concentration (0, 5, 10, 15, 20 and 25 µg/m) with DMSO as a control as described for MIC testing. Each compound and dilution was tested in triplicate. The plates were incubated overnight at 37° C. in a humidified incubator, without shaking and both growth and biofilm accumulation were determined at 16 h.

Following recording of turbidities, the culture medium was aspirated and the wells were washed three times with distilled water, blotted on paper towels, and fixed with 75% ethanol for 10 minutes.

To visualize biofilm material, 0.5% crystal violet was added to each well and after 5 minutes was removed and the wells washed three times with distilled water. Plates were read using a microplate reader at a wavelength of 570 nm. The dye was then extracted by adding 200 µl of 95% ethanol, and the absorbance was read again at 570 nm. All assays were performed in triplicate and the mean and standard deviation determined. Generally, the ethanol-solubilized crystal violet was more reliable and these determinations are reported throughout.

Catheter Adherence Model.

An overnight culture of S. epidermidis 9142 was used to inoculate fresh TSB medium to a final $OD_{600}$ of 0.01 in a volume of 3 ml in 15 ml screw capped tubes. Sterile sheets of polyurethane were divided into 1 cm square pieces and placed into tubes containing different concentrations of NTZ or controls containing DMSO. The tubes were incubated for 24 h with shaking Each catheter portion was washed 3 times with sterile PBS, suspended in 4 ml sterile PBS and sonicated for 10 min in a sonic water bath. 10 µl of the sonicated fluid was diluted in fresh PBS and plated onto TSA plates and incubated at 37° C. overnight. Bacteria were enumerated (triplicate plates) and the mean and standard deviation were determined and reported as CFU/ml. Viability effects were corrected for by plating the supernatants from the 3 ml experiment for total bacterial counts.

NTZ Effect on Biofilm Dispersal.

The effect of NTZ on biofilm accumulation or dispersal of existing biofilms was determined in microtiter dishes in which *S. epidermidis* 9142 was allowed to grow for 8 h prior to drug treatment. In this experiment duplicate flat bottom plates were inoculated with 200 µl of a bacterial suspension diluted in fresh TSB to an $OD_{600}$ of 0.01 and incubated statically at 37° C. Three rows of each plate contained no drug, while subsequent rows contained NTZ (2.5, 5, 10, and 15 µg/m). At 8 h, one plate was developed for biofilm determination as described above, while the medium in the replicate plate was aspirated and replaced with fresh TSB, with the first three rows now containing NTZ at 5, 10 and 15 µg/m and for the remaining wells, the same concentration of NTZ. These plates were developed at 24 h and the relative amount of biofilm for each set compared.

Direct Attachment Assay.

To determine if NTZ directly inhibited attachment of bacteria to plastic, an $OD_{600}$ of 0.01 suspension of *S. epidermidis* strain 9142 in TSB medium supplemented with 0.5% glucose was added to 6-well polystyrene microtiter plates (Nulcon, Nunc AIS. Denmark). After one hour incubation at 37° C., plates were washed 5× with 5 ml PBS to remove non-adherent bacteria and the adherent bacteria were visualized microscopically with a Zeiss Axiovert 200. The number of adherent bacteria per field was determined using Image Pro Plus software (Media Cybernetics, Bethesda, Md.) and the mean and standard deviation for 3 wells and multiple fields were compared between NTZ treated and untreated suspensions, and the experiment was repeated three times.

Effect of Zinc on the Action of NTZ.

To assess whether $ZnCl_2$ could overcome the inhibitory action of NTZ on biofilm production, standard biofilm assays were established at an NTZ concentration of 12.5 µg/ml, which is sufficient to abolish biofilm formation by *S. epidermidis* strain 9142 (~2×$IC_{50}$). A 10 µM $ZnCl_2$ solution was serially diluted in wells containing NTZ (in triplicate) and biofilm production was assessed at 24 h with crystal violet. As a control, $ZnCl_2$ was added to untreated bacteria. Additional controls included testing of 10 µm $CaCl_2$ and $MgCl_2$ in the same format. The inhibitory effect of EDTA on biofilm production and its reversibility by $Zn^{2+}$ was also assessed as described for NTZ. The effect of $Zn^{2+}$ on MIC of NTZ and AMIX was evaluated by microdilution in TSB at a fixed concentration of $Zn^{2+}$ at 20 µM (in triplicate).

Spectrophotometric Chelation Assay.

To test direct binding of $Zn^{2+}$ by NTZ in solution, we tested a range of concentrations of both NTZ and TIZ and scanned the solutions spectrophotometrically using an OLIS Cary-14 (OLIS Instruments Co., Bogart Ga.). Absolute spectra were recorded over a UV/Vis range from 220 nm to 700 nm. Spectral shifts in the 418 nm range would be attributable to changes in resonance within the thiazole ring that would result if $Zn^{2+}$ were coordinated by NTZ (9).

$^1$H NMR.

Chelation experiments were also performed utilizing NTZ and TIZ in DMSO-$d_6$ (0.5 mL) with $ZnCl_2$ using a 300 MHz Varian MercuryPlus spectrometer. Specifically, three ratios of NTZ to $Zn^{2+}$ were investigated (1:1, 1:2, 2:1) where NTZ was held constant (4 mg, 13 µmoles) while varying $ZnCl_2$ (1.8 mg, 13 µmoles or 3.5 mg, 26 µmoles) or NTZ (8 mg, 26 µmoles) with $ZnCl_2$ (1.8 mg, 13 µmoles). Three ratios of TIZ to $Zn^{2+}$ were also investigated (1:1, 1:2, 2:1) where TIZ was held constant (4 mg, 15 µmoles) while varying $ZnCl_2$ (2.1 mg, 15 µmoles or 4.1 mg, 30 µmoles) or TIZ (8 mg, 30 µmoles) with $ZnCl_2$ (2.1 mg, 15 µmoles). $^1$H NMR spectra were then obtained after mixing for 5 min, 24 h, 48 h, and 72 h at room temperature. Any chelation event would be evidenced by shifting or broadening of the thiazole and benzene protons as well as loss of the amide proton.

TABLE 1

Strains and primers used in this study.

| Strain or primer | Genotype/phenotype[a] | Reference or source |
|---|---|---|
| Strains | | |
| *Staphylococcus epidermidis* | | |
| 9142 | Wild-type PIA producing strain | (19) |
| CAV1005 | Native valve endocarditis clinical isolate | (35) |
| 5179 | CSF shunt infection isolate; biofilm- and PNAG negative strain; icaA::IS257 | (30) |
| 5179-R1 | 5179 revertant that produces a proteinaceous biofilm dependent on a truncated 140-kDa isoform of Aap; PNAG negative; icaA::IS257 | (30) |
| ICS1 | CRBSI | This study |
| ICS2 | CRBSI | This study |
| ICS3 | CRBSI | This study |
| ICS4 | CRBSI | This study |
| ICSS1 | CRBSI | This study |
| *Staphylococcus aureus* | | |
| NCTC 8325 | Reference strain | (12) |
| *Staphylococcus hominis* subsp. *novobiosepticus* | | |
| F13532 | Blood culture isolate | (2) |
| *Staphylococcus haemolyticus* | | |
| S33208 | Blood culture isolate | This study |
| Primer (5' → 3') | | |
| serp0107 | | |
| Serp0107F | | (16) |
| Serp0107R | | (16) |
| tuf | | |
| TStaG422 | | (21) |
| TStag765 | | (21) |

[a]CRBSI, catheter related bloodstream infection; I, inosine

Results

MIC Testing of *S. aureus* and *S. epidermidis* Strains.

The inhibitory effect of NTZ on staphylococcal strains was investigated first by determining MIC. The present studies show unexpectedly that most strains tested were susceptible to NTZ and TIZ with an MIC range of 8-16 µg/ml, indicating these strains are generally more susceptible to this drug than previously reported (6). In contrast to previous studies where the drug was only active under anaerobic conditions (6) NTZ inhibited the growth of *S. epidermidis* in liquid culture under vigorous aeration in a dose dependent manner with significant inhibition at 25 µg/m (see FIG. 1). At lower drug concentrations (10 µg/m), there was little effect on exponential growth rates. Under static (microaerobic) growth conditions, biofilm accumulation on the bottom of flasks was completely ablated by 15 µg/m of NTZ, while final bacterial turbidities were unchanged over drug-free controls (data not presented).

NTZ Inhibits Biofilm Production at Sub-MIC Levels.

Figure 2:
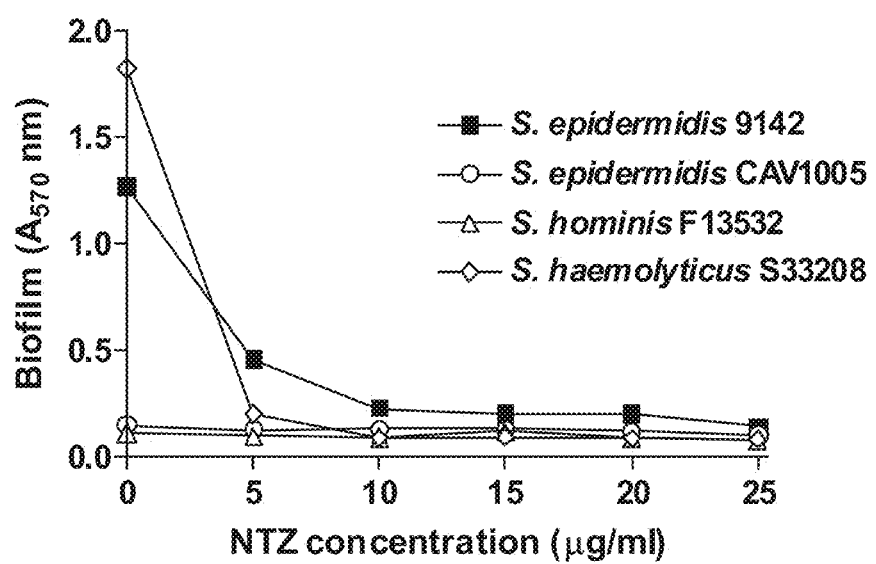
FIG. 2. Biofilm inhibition by NTZ. Staphylococcus strains were grown in the presence of different concentrations of NTZ in 96 well polystyrene plates and subjected to crystal violet staining after 24 h as described in the text. The biofilm positive strains used are *S. epidermidis* 9142 (●), *S. haemolyticus* 33208 (■) and the biofilm negative strains are *S. hominis* 13532 (▲) and *S. epidermidis* CAV 1005 (♦). The $IC_{50}$ for biofilm producing strains was 2.5 µg/ml.

To explore the sub-MIC drug effects on biofilm accumulation, we screened several CoNS species for biofilm production. As seen in FIG. 2, NTZ inhibited biofilm production by S. epidermidis strain 9142 in a dose dependent manner as determined by crystal violet staining Bacterial growth was not appreciably affected at concentrations of NTZ below 16 µg/ml. The $IC_{50}$ for strain 9142 and S. haemolyticus strain 33208 was determined to be 2.5 µg/ml (~8 µM). While not depicted, the deacetylated form of NTZ (TIZ) gave equivalent results while the denitro form of the drug did not inhibit biofilm production and exhibited MIC>32 µg/m (data not presented).

Screening NTZ Activity Against S. epidermidis Strains.

To determine if the sub-MIC antibiofilm activity of NTZ was more generalized, we screened a series of clinical S. epidermidis isolates obtained from patients with CRBSI. NTZ inhibited biofilm formation by all clinical isolates that produced biofilm in the absence of the drug in a dose dependent manner (FIG. 2A). Furthermore, NTZ inhibited biofilm formation by the S. epidermidis strain 5179-R1 (see FIG. 2B), which generates a PNAG-independent, protein-rich biofilm that is dependent on the production of a proteolytically processed derivative of the Aap protein (30). For all strains tested, the $IC_{50}$ ranged between 2.5 and 5 µg/ml. While these findings suggest that Ica proteins may not be the target of NTZ action, we cannot unequivocally rule this out as the original icaA mutant strain 5179 was biofilm negative and produced the Aap protein (30).

NTZ Inhibits Bacterial Binding to Catheters.

Figure 3A:
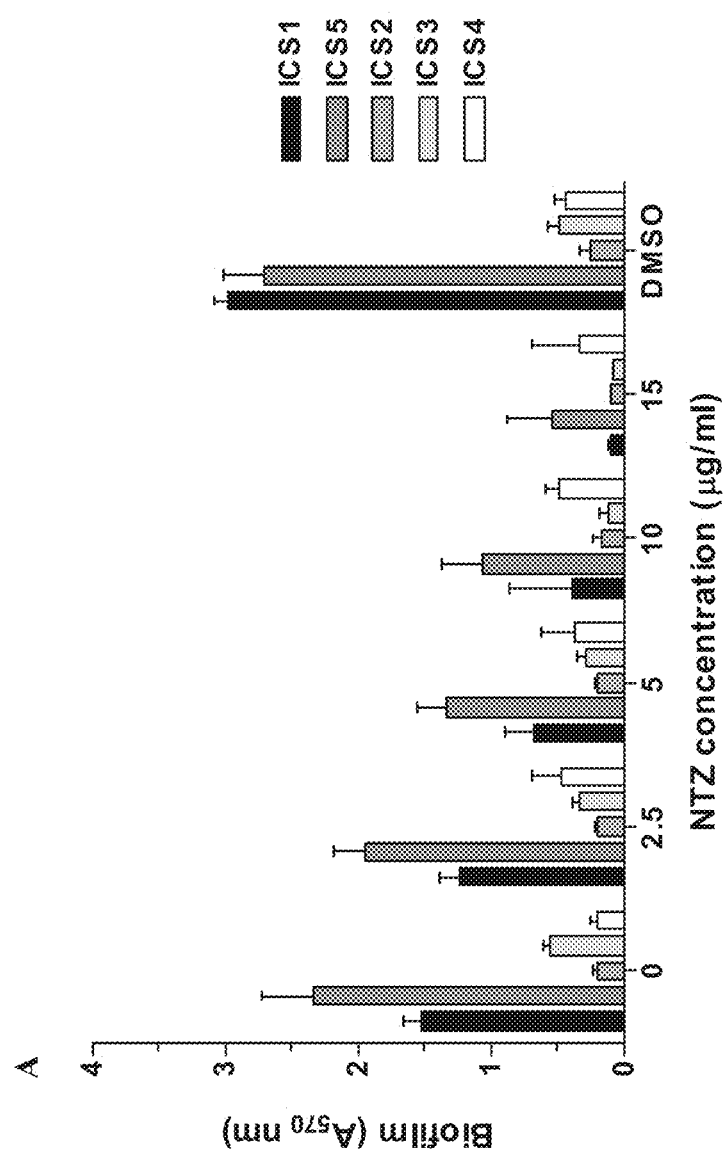
FIG. 3 (A and B). Screening for antibiofilm activity. A. Clinical isolates confirmed as *S. epidermidis* were tested for biofilm production and for concentration depending biofilm inhibition by NTZ at the indicated concentrations with DMSO serving as an additional control. ICS1 and ICS5 strains were biofilm positive. B. Concentration dependent inhibition of biofilm production of *S. epidermidis* strains 9142, icaA mutant strain 5179 and revertant strain 5179-R1 that produces a truncated Aap protein. The data presented represent the mean and standard deviation of three replicates.
Figure 3B:
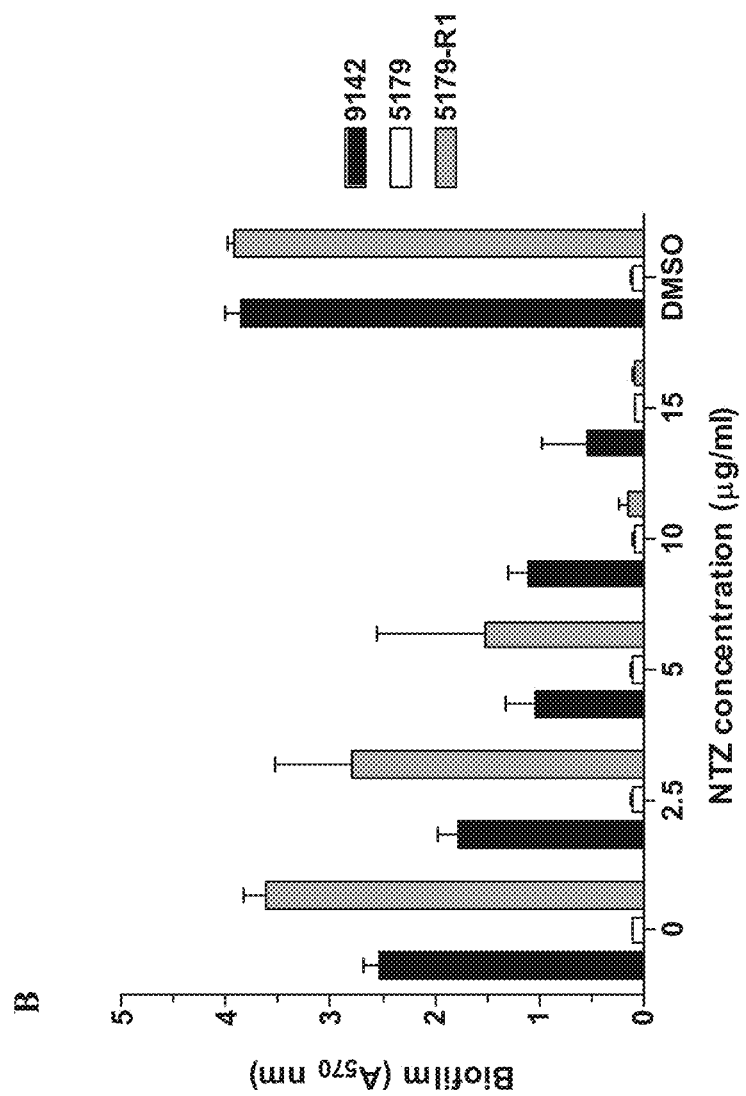

Several studies have indicated that bacterial attachment and biofilm accumulation are distinct but interrelated activities (7). To test whether NTZ interfered with attachment, biofilm producing strains of S. epidermidis were scored for attachment to plastic squares derived from catheter material in the presence or absence of NTZ. As seen in FIG. 3A, NTZ inhibited attachment of S. epidermidis strain 9142 in a dose dependent manner and within the $IC_{50}$ concentration range. Since the attachment to catheter pieces was conducted over a 24 h period, we next examined primary attachment after 1 h incubation with direct microscopic enumeration of adherent bacteria. As seen in FIG. 3B, NTZ inhibited primary attachment to plastic by 80% at 12.5 µg/ml. The apparent fast action of NTZ might suggest a mechanism by which the drug interferes with the function of existing surface structures that mediate primary attachment rather than inhibiting production of newly synthesized molecules.

To test this possibility we determined primary attachment efficiencies for S. epidermidis strain 9142 grown in TSB broth over night in the presence or absence of 15 µg/m of NTZ under aerobic or static growth conditions. Final turbidities were equivalent for all cultures, but static cultures+NTZ and aerobic cultures contained no visible evidence of biofilm accumulation. PBS suspensions of these bacteria were then tested for primary attachment at 4 and 37° C. Aerobically grown bacteria were much less efficient at attachment to plastic than statically grown bacteria and in each condition; growth in the presence of NTZ showed no inhibitory effect. These studies suggest that under biofilm permissive conditions, NTZ does not interfere with synthesis or function of surface adhesins. However, sub-MIC levels of NTZ appear to affect the ability of aerobically grown bacteria to transition to a more adherent and biofilm proficient phenotype.

Does NTZ Affect Biofilm Production by Colonized Bacteria?

Figure 4A:
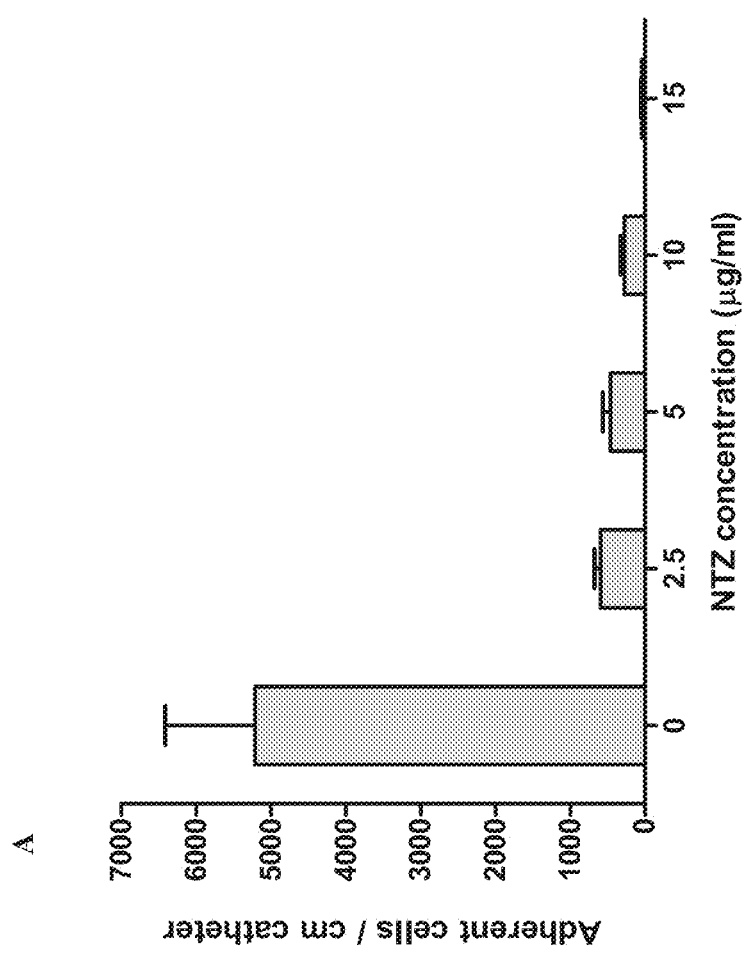
FIG. 4 (A and B). Effect of NTZ on attachment to catheter. A. One centimeter square polyurethane pieces were incubated with indicated concentrations of NTZ and *S. epidermidis* strain 9142 and adherent bacteria were enumerated at 24 h. B. NTZ-concentration dependent inhibition of primary attachment of strain 9142 to plastic surfaces was enumerated microscopically using ImagePro software. Mean and standard deviation of multiple replicates are presented.
Figure 4B:
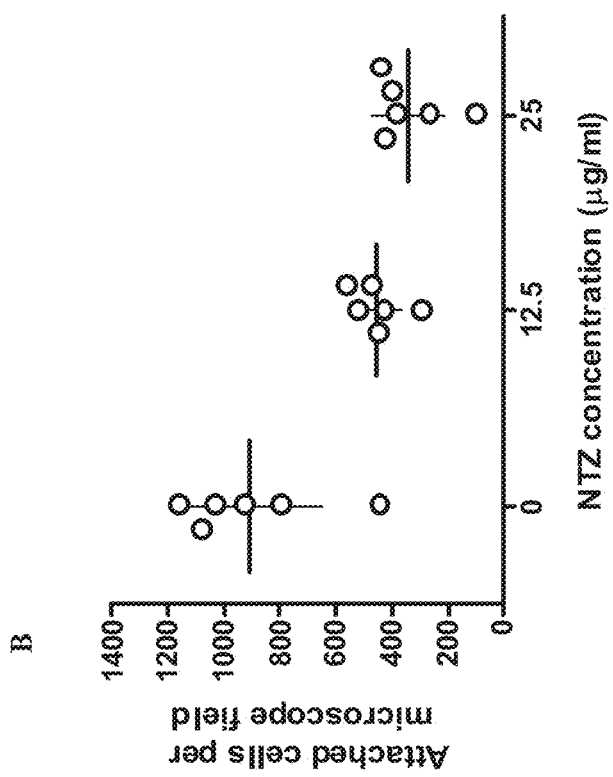
Figure 5:
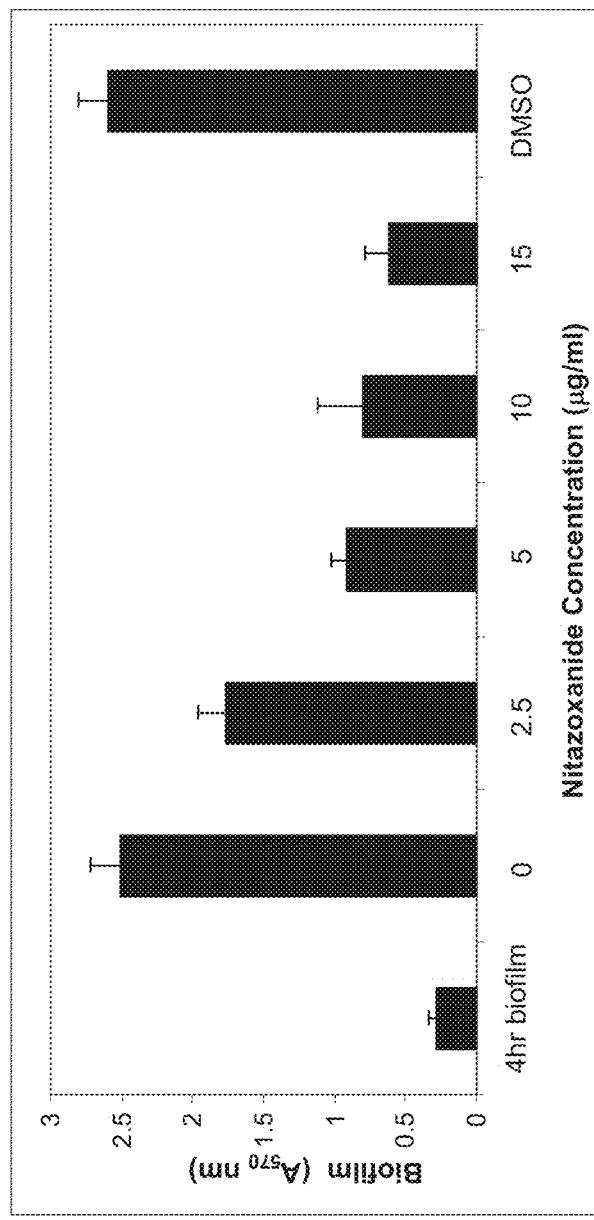
FIG. 5. Biofilm dispersal by NTZ. *S. epidermidis* strain 9142 bacteria were grown under biofilm producing conditions for 4 h and following washing, fresh medium and the indicated concentrations of NTZ added for an additional 16 h and the biofilm accumulation was determined with crystal violet. NTZ inhibited further biofilm formation in a concentration dependent manner, but did not disperse existing biofilm.

We next investigated whether NTZ was inhibitory to biofilm production by established S. epidermidis communities. Assuming that NTZ is a specific inhibitor of adherence, the drug should not affect further deposition of biofilm by established communities. To test this hypothesis, we allowed S. epidermidis bacteria to establish biofilm in the absence of drug for 4 h, and following washings to remove non-adherent bacteria, NTZ (range of concentrations) was added in fresh TSB medium for an additional 12 h. As seen in FIG. 4, the biofilm produced at 4 hr was ca 0.5 absorbance units by the crystal violet assay and by the end of the assay; the accumulated biofilm had increased to 3 absorbance units in the non-drug treated well. While biofilm also increased in the NTZ treated wells, there was a drug dependent effect on the accumulation of additional biofilm material. However, drug treatment did not eliminate the preformed biofilm indicating that NTZ was not dispersive.

Reversal of NTZ Inhibition by Zinc.

Figure 6:
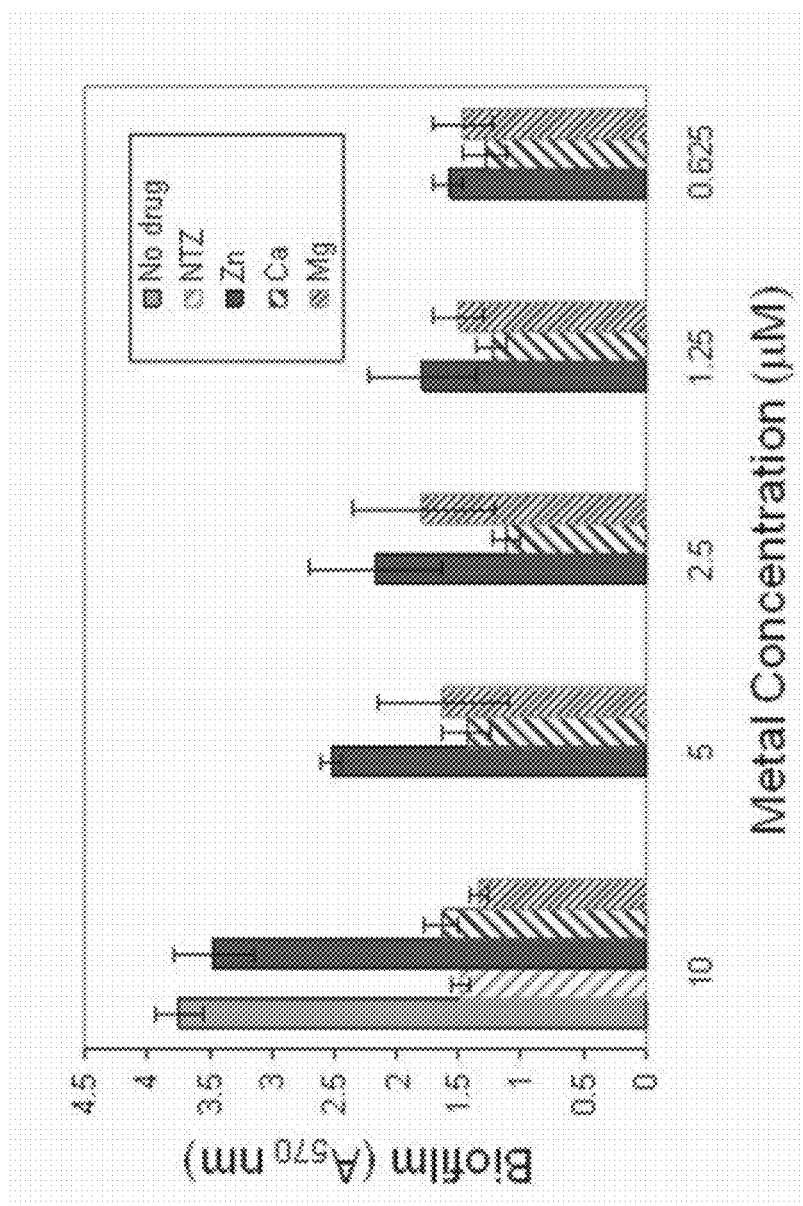
FIG. 6. Effect of zinc on NTZ antibiofilm action. Zinc chloride, calcium chloride and magnesium chloride (see legend) were added to TSB containing a fixed concentration of NTZ (12.5 ng/ml) at the indicated concentrations up to 10 µM. Zinc chloride, but not the other metals reversed the biofilm inhibitory effect of NTZ with 50% reversal at ~5 µM. Data presented are in triplicate with mean and standard deviation indicated.

The surface proteins Aap of S. epidermidis and SasG of S. aureus mediate attachment to surfaces and that metal chelators like EDTA can inhibit attachment (13, 4). Studies by Conrady et al (4) have shown that these staphylococcal surface proteins contain G5 domain repeats that mediate associative accumulation of bacteria onto surfaces in a $Zn^{2+}$-dependent manner. These domains bind $Zn^{2+}$, which is hypothesized to enable $Zn^{2+}$ zipper protein interactions to entwine protein ribbons in adherent bacterial aggregates on surfaces. To test whether NTZ affects metal chelation by the G5 domains of Aap proteins of S. epidermidis, we added increasing concentrations of $Zn^{2+}$ to the biofilm assays to see if the NTZ inhibition could be reversed. As seen in FIG. 6, addition of $Zn^{2+}$ led to equivalent increases in biofilm accumulation; results that were similar if EDTA was used in place of NTZ (data not shown). The effects of $Zn^{2+}$ were specific, as addition of other metals (calcium and magnesium) did not reverse the inhibition. While NTZ seems to achieve the same phenotype as treatment with EDTA, we could not distinguish between NTZ acting directly as a $Zn^{2+}$ chelator or if NTZ bound to G5 domains.

To test whether NTZ displaced $Zn^{2+}$, bacteria from overnight cultures grown in the presence of 15 µg/ml NTZ were washed and treated with a range of $Zn^{2+}$ concentrations in an add-back attachment assay. The addition of $Zn^{2+}$ up to 20 µM, did not improve the efficiency of bacterial attachment to plastic, which was already efficient as indicated earlier. We should note here that the primary attachment of bacteria to plastic may also involve adhesins that do not require $Zn^{2+}$, so a negative result does not necessarily exclude the possibility that NTZ affects Aap function.

$Zn^{2+}$ Chelation by NTZ.

To address whether $Zn^{2+}$ is directly chelated by NTZ, we scanned putative NTZ-$Zn^{2+}$ coordination complexes for any spectral changes that might result from changes in ring resonance due to bound ligand. Based on NMR studies, the anionic form of NTZ exists in several resonance states that exist simultaneously for the amino thiazole moiety which contribute to the absorption maxima at 418 nm (9). Metal coordination would be predicted to alter resonance and this should manifest in a spectral shift. Spectral scans performed at different concentrations of NTZ and TIZ with $Zn^{2+}$ did not reveal any changes in absorption spectrum (data not presented). To further explore NTZ metal interactions, putative NTZ and TIZ complexes with $Zn^{2+}$ were analyzed by $^1$H NMR spectroscopy in DMSO-$d_6$. No chelation with $ZnCl_2$ was evident from any ratios tested even after the 72 hour time point. All spectra remained identical and unchanged throughout the course of the experiment. Tizoxanide also displayed no chelation with $ZnCl_2$ under the experimental conditions. Taken together, these studies indicated that these drugs did not chelate zinc under these assay conditions.

Hydrophobicity Effects.

NTZ is hydrophobic and sparingly soluble in water and its deacylated form (TIZ) is 97.5% bound to plasma proteins (33). It is possible therefore, that the action of the drug is nonspecific and results from binding onto surface proteins and ablating their action. To test this possibility we synthesized a more soluble derivative of NTZ (AMIX) by adding an ethylamine R group to the benzene ring of TIZ. The drug retained bioactivity with an MIC of 16-32 µg/ml. This derivative was soluble at 0.4 mg/ml in water (NTZ<32 µg/m) and as seen in FIG. 6 exhibited a slightly higher $IC_{50}$ than NTZ (8 versus 4 µg/ml, respectively). The 2-fold difference in biofilm inhibition was less than the 15-fold difference in solubility and in both cases, zinc reversed the inhibition. Taken together, these studies suggest that the action of NTZ in blocking primary attachment is most likely specific.

$Zn^{2+}$ does not Reverse MIC of NTZ or AMIX.

Figure 7:
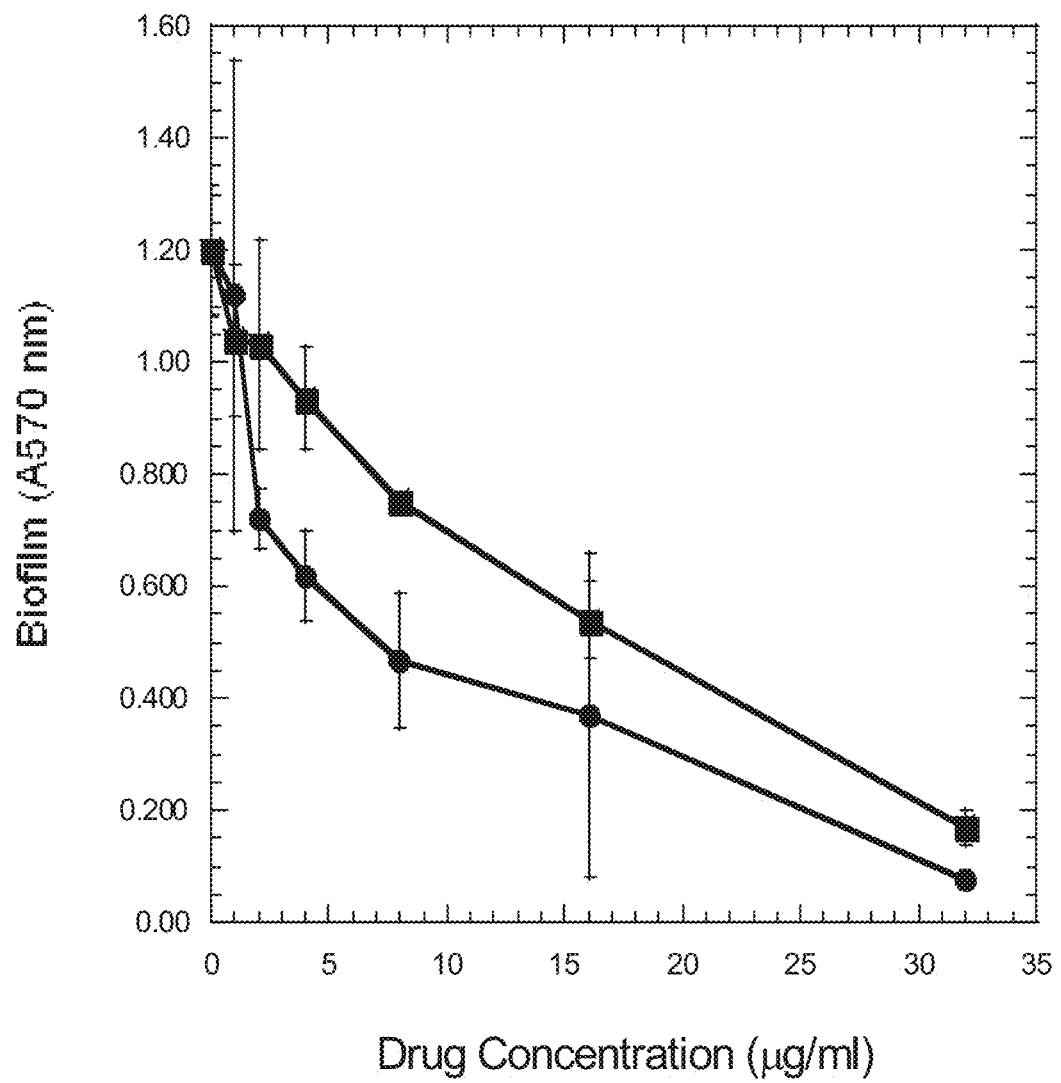
FIG. 7. Comparative antibiofilm activity of NTZ and AMIX. Concentration dependent inhibition of biofilm production by *S. epidermidis* strain 9142 by NTZ (●) and water soluble AMIX (■). All assays were performed in triplicate with mean and standard deviation presented.
Figure 8:
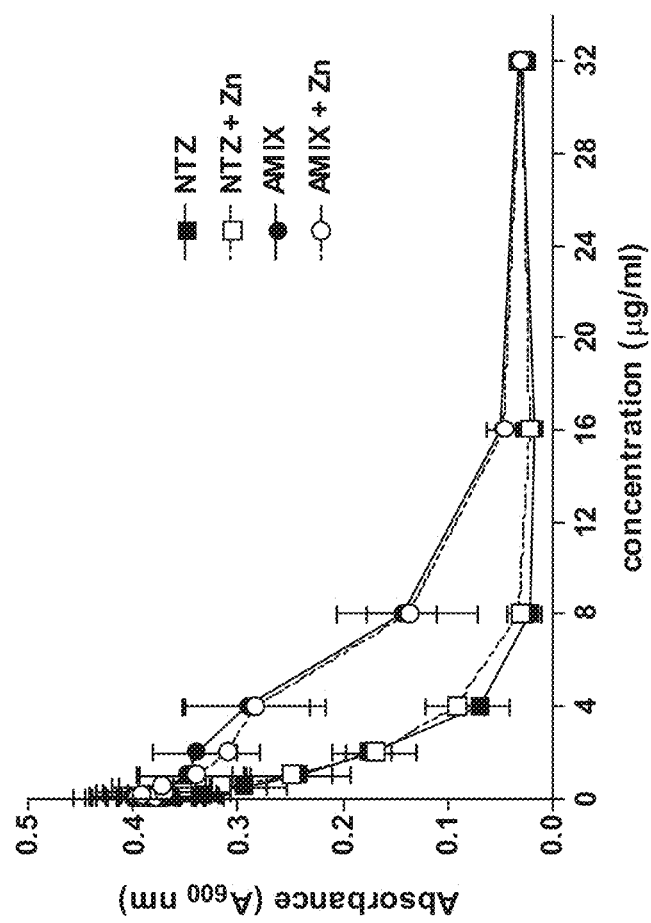
FIG. 8. Effect of zinc (20 µM) on reversal of growth inhibition (MIC) by NTZ and AMIX. The standard microdilution assay with *S. epidermidis* strain 9142 was set up with serial dilutions of NTZ or AMIX and the same dilutions at fixed concentration of $ZnCl_2$ at 20 µM: NTZ+$Zn^{2+}$ and AMIX+$Zn^{2+}$ (see enclosed legend). All assays were performed in triplicate and mean and standard deviation presented.

To test whether the action of $Zn^{2+}$ on ablation of biofilm by NTZ might result from reversal of the growth inhibitory effect, MIC tests were repeated in the presence of a fixed concentration of zinc (20 µM). Two independent experiments were conducted and read at both 8 and 24 h post inoculation. As seen in FIG. 7, $Zn^{2+}$ had no effect on the inhibitory action of NTZ or AMIX at 8 h. Some breakthrough growth was noted by 24 h in the NTZ plus $Zn^{2+}$ wells suggesting slight beneficial effects perhaps due to deposition of biofilm in these assay conditions. Growth of S. epidermidis in the presence of NTZ prevents biofilm production in broth. These bacteria do not aggregate or accumulate on surfaces and one might predict that if NTZ removed zinc from the Aap proteins, then adding zinc back should restore accumulation on surfaces and aggregation in liquid. Adding zinc back to these bacteria did not restore the biofilm phenotype suggesting that Aap protein may be absent from the surface of S. epidermidis. It is therefore likely that NTZ either inhibits expression of the aap gene or alters assembly of the protein on the bacterial surface. Similarly, NTZ must also ablate expression of ica genes that encode PIA polysaccharide.

Discussion

It is disclosed herein that the antiparasitic drug nitazoxanide and its active metabolite tizoxanide are inhibitory to in vitro growth of various staphylococcal species, including MRSA strains of S. aureus (MIC=8-16 µg/m). This contrasts with an earlier finding by Dubreuil et al. (6), who reported that tizoxanide was not active while NTZ was only inhibitory to growth of S. aureus strains under anaerobic growth conditions. It is disclosed herein the unexpected result that NTZ inhibited growth of S. epidermidis strain 9142 in highly aerated broth cultures at 25 µg/ml. We also found no difference in inhibitory action between NTZ and the active metabolite TIZ by microdilution in shaken or static cultures. The present studies further demonstrate that at sub-MIC concentrations (2-8 µg/m), NTZ and TIZ inhibited production of biofilm in a static microtiter plate assay. While growth inhibition does contribute to biofilm inhibition, generally the effects manifest at drug concentrations greater than 16 µg/ml. The anti-biofilm activity of NTZ could be reversed by 10 to 20 µM zinc, but not by similar concentrations of $Ca^{2+}$ or $Mg^{2+}$. The data disclosed herein suggest that NTZ likely affects a single essential target that at high concentrations of drug inhibits growth and at low concentration ablates biofilm production.

We further determined that NTZ inhibits primary attachment of aerobically grown S. epidermidis strain 9142 to surfaces within 1 h in a concentration dependent manner. However, NTZ had no effect on primary attachment by statically grown bacteria, even though biofilm production was ablated. In the former case, we speculate that aerobically growing planktonic bacteria may not appreciably produce adhesins as indicated by the much lower efficiency for primary attachment. Under these conditions, NTZ affects the ability of these bacteria to either adhere or produce biofilm under biofilm promoting microaerobic conditions. This latter mechanism can be reversed by $Zn^{2+}$. In the case of pre-formed biofilm as noted in the dispersal experiment, addition of NTZ ablates further accumulation in a dose dependent manner. Taken together, our studies suggest that NTZ likely affects the accumulation process which includes elaboration of PNAG (PIA).

Without wishing to be bound by any particular theory, a likely candidate for the action of NTZ is the zinc-dependent associative adhesion protein (Aap) that has been extensively studied and recently demonstrated to mediate primary attachment of S. epidermidis to surfaces (4). Importantly, purified Aap protein monomers associated into aggregates in the presence of $Zn^{2+}$ and this association was mediated by G5 domains (4). The action of NTZ did not appear to result from direct chelation of zinc, as is the case for the anti-biofilm action of EDTA and other metal chelators or by low pH (13, 4). Both the $IC_{50}$ for anti-biofilm activity of NTZ (~8 µM) and the $IC_{50}$ for $Zn^{2+}$ reversal of this inhibition (5 µM) support a competition model for binding to G5 zinc-zipper domains of Aap proteins (4). Alternatively, a similar phenotype might be obtained if NTZ non-specifically bound to surface proteins, polysaccharides, or teichoic acids through hydrophobic or ionic interactions or even by affecting a global regulator (37). To address hydrophobic interactions, we synthesized a hydrophilic variant of NTZ (AMIX) that was ~15-fold more soluble in water than NTZ, but was decreased in anti-biofilm potency by 2-fold. Despite the circumstantial evidence supporting Aap as the drug target, we should note from earlier studies that sub-MIC levels of NTZ also apparently inhibits secretion of VacA cytotoxin by H. pylori by a mechanism that does not involve the inhibition of protein synthesis (36). Unfortunately, most chemical entities described as anti-biofilm agents are non-specific and often affect both Gram positive and negative bacteria (10). Further mechanistic studies will be required in order to validate Aap as the target of NTZ.

The anion of NTZ is most likely the active form that inhibits growth and biofilm production by S. epidermidis, but it apparently does not promote chelation of $Zn^{2+}$. Since the pKa for NTZ is 6.2 (9), it may be difficult to prove the point as acidic conditions also inhibit biofilm formation, presumably by removal of $Zn^{+2}$ from G5 domains of Aap (4). The 5-nitro group is required to produce resonance within the thiazole ring and thus, the denitro derivative exhibits no anti-biofilm activity. The notion that NTZ might affect assembly of surface proteins is supported by recent findings that NTZ ablates assembly of fimbrial adhesins (AafA and Type I) in E. coli (manuscript submitted to AAC).

Coating catheters with antimicrobial agents has been show to delay or prevent microbial colonization and to extend their useful lifespan (1, 3, 13, 20). In simulated catheter experiments, we showed that NTZ blocked the attachment of bacteria to catheter surfaces, but displayed no dispersal activity against existing biofilm material. However, addition of drug to established biofilms prevented further accumulation, which might have potential for systemic applications. While NTZ has poor pharmacophoric properties, it is likely that less hydrophobic derivatives, such as AMIX, might prove more efficacious in treating systemic infections. AMIX is less toxic (than NTZ) to staphylococci by MIC testing and retains anti-biofilm activity. Studies are in progress to assess the anti-colonization potential of this class of therapeutics against S. epidermidis and S. aureus strains and to continue developing more potent derivatives.

Primary attachment of microorganisms to surfaces is an essential first step in the infection process. Targeting the function of these virulence determinants might provide an additional strategy for limiting or reducing the severity of infections. Our findings extend early observations of Dubreuil et al by demonstrating that NTZ and TIZ are more potent against staphylococcal species including MRSA strains under aerobic as well as microaerobic conditions than previously considered (6). Moreover, sub-MIC levels of these drugs are active inhibitors of staphylococcal biofilm production and accumulation on surfaces. While the ability to ablate the inhibitory action of NTZ by addition of stochiometric concentrations of $Zn^{2+}$ salts implicates Aap proteins as putative targets, further mechanistic studies will be required to validate this target. Since G5 domains are found in other surface proteins, including SasG in *S. aureus* (5), perhaps these compounds will display a broader effect against other pathogens.

BIBLIOGRAPHY

Example 1

1. Aslam S., B. W. Trautner, V. Ramanathan, and R. O. Darouiche. 2007. Combination of tigecycline and N-acetylcysteine reduces biofilm-embedded bacteria on vascular catheters. Antimicrob Agents Chemother. 51:1556-1558.
2. Begun, J., J. M. Gaiani, H. Rohde, D. Mack, S. B. Calderwood, F. M. Ausubel, and C. D. Sifri. 2007. Staphylococcal biofilm exopolysaccharide protects against *Caenorhabditis elegans* immune defenses. PLoS Pathog. 3:e57
3. Cerca, N., S. Martins, S. Sillankorva, K. K. Jefferson, G. B. Pier, R. Oliverira and J. Azeredo. 2005. Effects of growth in the presence of subinhibitory concentrations of dicloxacillin on *Staphylococcus epidermidis* and *Staphylococcus haemolyticus* biofilms.
4. Conrady D G, Brescia C C, Horii K, Weiss A A, Hassett D J, Herr A B 2008. A zinc-dependent adhesion module is responsible for intercellular adhesion in staphylococcal biofilms. Proc Natl Acad Sci USA. 105:19456-1961.
5. Corrigan, R. M., D. Rigby, P. Handley, and T. J. Foster. 2007. The role of *Staphylococcus aureus* surface protein SasG in adherence and biofilm formation. Microbiol. 153: 2435-2446.
6. Dubreuil, L., I. Houcke, Y. Mouton, J. F. Rossignol. 1996. In vitro evaluation of activities of nitazoxanide and tizoxanide against anaerobes and aerobic organisms. Antimicrob Agents Chemother. 40:2266-2270.
7. Heilmann C., O. Schweitzer, C. Gerke, N. Vanittanakom, D. Mack, and F. Gotz. 1996. Molecular basis of intercellular adhesion in the biofilm-forming *Staphylococcus epidermidis*. Mol Microbiol 20: 1083-1091.
8. Hemphill, A., J. Mueller, and M. Esposito. 2006. Nitazoxanide, a broad-spectrum thiazolide anti-infective agent for the treatment of gastrointestinal infections. Expert Opin Pharmacother. 7:953-964.
9. Hoffman, P. S., G. Sisson, M. A. Croxen, K. Welch, W. D. Harman, N. Cremades, and M. G. Morash. 2007. Antiparasitic drug nitazoxanide inhibits the pyruvate oxidoreductases of *Helicobacter pylori*, selected anaerobic bacteria and parasites, and *Campylobacter jejuni*. Antimicrob Agents Chemother. 51:868-876.
10. Huigens, R. W. III, S. A. Rogers, A. T. Steinhauer and C. Melander. 2009. Inhibition of *Acinetobacter baumannii*, *Staphylococcus aureus* and *Pseudomonas aeruginosa* biofilm formation with a class of TAGE-triazole conjugates. Org. Biomol. Chem. 7:794-802.
11. Hussain, M., M. Herrmann, C. von Eiff, F. Perdreau-Remington, G. Peters. 1997. A 140-kilodalton extracellular protein is essential for the accumulation of *Staphylococcus epidermidis* strains on surfaces. Infect Immun 65:519-524.
12. Iandolo, J. J. 2000. Genetic and physical map of the chromosome of *Staphylococcus aureus* 8325, p. 317-325. In V. A. Fischetti, R. P. Novick, J. J. Ferretti, D. A. Portnoy, and J. A. Rood (ed.), Gram-positive pathogens. ASM Press, Washington, D.C. Appl. Environ. Microbiol. 71:8677-8682.
13. Juda, M., K. Paprota, D. Jaloza, A. Malm, P. Rybojad, K. Goździuk. 2008. EDTA as a potential agent preventing formation of *Staphylococcus epidermidis* biofilm on polychloride vinyl biomaterials. Ann Agric Environ Med 15:237-241.
14. Klevens, R. M., J. R. Edwards, C. L. Richards Jr, T. C. Horan, R. P. Gaynes, D. A. Pollock, and D. M. Cardo. 2007. Estimating health care-associated infections and deaths in U.S. hospitals, 2002. Public Health Reports (NNIS), 122: 160-166.
15. Kontos, F., E. Petinaki, I. Spiliopoulou, M. Maniati, and A. N. Maniatis. 2003. Evaluation of a novel method based on PCR restriction fragment length polymorphism analysis of the tuf gene for the identification of *Staphylococcus* species. J Microbial Methods 55:465-469.
16. Liu, D., E. Swiatlo, F. W. Austin, and M. L. Lawrence. 2006. Use of a putative transcriptional regulator gene as target for specific identification of *Staphylococcus epidermidis*. Lett Appl Micro 43:325-330.
17. Mack, D., W. Fischer, A. Krokotsch, K. Leopold, R. Hartmann, H. Egge, and R. Laufs. 1996. The intercellular adhesin involved in biofilm accumulation of *Staphylococcus epidermidis* is a linear β-1,6-linked glucosaminoglycan: purification and structural analysis. J. Bacteriol. 178: 175-183.
18. Mack D., M. Nedelmann, A. Krokotsch, A. Schwarzkopf, J. Heesemann, and R. Laufs 1994 Characterization of transposon mutants of biofilm-producing *Staphylococcus epidermidis* impaired in the accumulative phase of biofilm production: genetic identification of a hexosamine-containing polysaccharide intercellular adhesin. Infect Immun 62: 3244-3253.
19. Mack, D., N. Siemssen, and R. Laufs 1992 Parallel induction by glucose of adherence and a polysaccharide antigen specific for plastic-adherent *Staphylococcus epidermidis*: Evidence for functional relation to intercellular adhesion. Infect Immun 60: 2048-2057.
20. Maki, D. G., S. M. Stolz, S. Wheeler, and L. A. Mermel. 1997. Prevention of central venous catheter-related bloodstream infection by use of an antiseptic-impregnated catheter. A randomized, controlled trial. Ann Intern Med. 127: 257-266.
21. Martineau, F, F. J. Picard, D. Ke, S. Paradis, P. H. Roy, M. Ouellette, and M. G. Bergeron. 2001. Development of a PCR assay for identification of staphylococci at genus and species levels. J Clin Microbiol. 39:2541-2547.
22. McVay, C. S., and R. D. Rolfe. 2000. In vitro and in vivo activities of nitazoxanide against *Clostridium difficile*. Antimicrob Agents Chemother. 44:2254-2258.
23. Mermel, L. A. 2000. Prevention of intravascular catheter-related infections. Ann Intern Med 132:391-402.
24. Müller, J., D. Sidler, U. Nachbur, J. Wastling, T. Brunner, and A. Hemphill. 2008. Thiazolides inhibit growth and induce glutathione-S-transferase Pi (GSTP1)-dependent cell death in human colon cancer cells. Int J Cancer. 123: 1797-1806.

25. Müller, J., J. Wastling, S. Sanderson, N. Müller, A. Hemphill. 2007. A novel *Giardia lamblia* nitroreductase, GlNR1, interacts with nitazoxanide and other thiazolides. Antimicrob Agents Chemother. 51:1979-1986.
26. Musher, D. M., N. Logan, A. M. Bressler, D. P. Johnson, J. F. Rossignol. 2009. Nitazoxanide versus vancomycin in *Clostridium difficile* infection: A randomized, double-blind study. Clin Infect Dis. 48:41-46.
27. National Nosocomial Infections Surveillance. 2004. National Nosocomial Infections Surveillance (NNIS) System Report, data summary from January 1992 through June 2004, issued October 2004. Am. J. Infect. Control 32:470-485.
28. Pankuch, G. A., and P. C. Appelbaum. 2006. Activities of tizoxanide and nitazoxanide compared to those of five other thiazolides and three other agents against anaerobic species. Antimicrob Agents Chemother. 50:1112-1117.
29. Parsek M R and P K Singh. 2003. Bacterial biofilms: an emerging link to disease pathogenesis. Ann Rev Microbiol (2003) 57:677-701.
30. Rohde, H., C. Burdelski, K. Bartscht, M. Hussain, F. Buck, M. A. Horstkotte, J. K. Knobloch, C. Heilmann, M. Herrmann, and D. Mack. 2005. Induction of *Staphylococcus epidermidis* biofilm formation via proteolytic processing of the accumulation-associated protein by staphylococcal and host proteases. Mol. Microbiol. 55:1883-1895.
31. Rupp, M. E., J. S. Ulphani, P. D. Fey, and D. Mack. 1999. Characterization of *Staphylococcus epidermidis* polysaccharide intercellular adhesin/hemagglutinin in the pathogenesis of intravascular catheter-associated infection in a rat model. Infect. Immun. 67:2656-2659.
32. Sisson, G., A. Goodwin, A. Raudonikiene, N. J. Hughes, A. K. Mukhopadhyay, D. E. Berg, and P. S. Hoffman. 2002. Enzymes associated with reductive activation and action of nitazoxanide, nitrofurans, and metronidazole in *Helicobacter pylori*. Antimicrob Agents Chemother. 46:2116-23.
33. Stockis, A., X. Deroubaix, R. Lins, B. Jeanbaptiste, P. Calderon, and J. F. Rossignol. 1996. Pharmacokinetics of nitazoxanide after single oral dose administration in 6 healthy volunteers. Int J Clin Pharmacol Ther. 34:349-351.
34. von Eiff, C., G. Peters, and C. Heilmann. 2002. Pathogenesis of infections due to coagulase-negative staphylococci. Lancet Infect. Dis. 2:677-685.
35. Winchester, D. E., M. J. Lipinski, M. E. Cupp, and C. D. Sifri. 2008. Am J Med. 121:855-857.
36. Yamamoto, Y., A. Hakki, H. Friedman, S. Okubo, T. Shimamura, P. S. Hoffman, and J. F. Rossignol. 1999. Nitazoxanide, a nitrothiazolide antiparasitic drug, is an anti-*Helicobacter pylori* agent with anti-vaculating toxin activity. Chemother. 45:303-312.
37. Yang, L., M. T. Rybtke, T. H. Jakobsen, M. Hentzer, T. Bjarnsholt, M. Givskov, and T. Tolker-Nielsen. 2009. Computer-aided identification of recognized drugs as *Pseudomonas aeruginosa* quorum-sensing inhibitors. Antimicrob Agents Chemother. 53:2432-2443.
38. Vuong, C., and M. Otto. 2002. *Staphylococcus epidermidis* infections. Microbes Infect. 4:481-489.

Example 2

Biofilms

Nitazoxanide Inhibits Biofilm Production and Hemagglutination by Enteroaggregative *Escherichia coli* Strains by Blocking Assembly of AafA Fimbriae Here we investigated whether the broad spectrum antiparasitic and anti-diarrheal drug nitazoxanide (NTZ) might be active against EAEC in vitro. While *E. coli* strains were resistant to NTZ in rich LB medium (MIC>64 µg/m), the drug was slightly inhibitory in a minimal medium supplemented with glucose (MinA-G medium, MIC~32 µg/m). NTZ also inhibited biofilm production by strain EAEC 042 in both DMEM and MinA-G media with an $IC_{50}$ of ~12 µg/ml. Immunofluorescence and immunoblot with antibody against AAF/II major fimbrial subunit AafA established that AAF/II filaments were dramatically reduced on bacteria grown in the presence of NTZ. Comparative qRT-PCR and reporter gene fusions (aafA:phoA) indicated that aafA expression was unaffected by NTZ while aggR transcript levels and aggR:lacZ expression were increased ~10- and 2.5-fold, respectively over untreated controls. More generally, NTZ inhibited hemagglutination (HA) of red blood cells by the non-biofilm producing strain JM221 expressing either AAF/I or Type I fimbriae. Our findings suggest that the inhibitory action of NTZ on biofilm formation and HA is likely due to inhibition of fimbrial assembly.

Nitazoxanide shows broad spectrum in vitro activity against anaerobic bacteria, including *Clostridium difficile* and members of the epsilon proteobacteria including *Helicobacter pylori* and *Campylobacter jejuni* (16, 38). In these organisms, NTZ is a potent inhibitor of the pyruvate ferredoxin oxidoreductase (16, 38). The anionic nature of the active form of NTZ and its ability to abstract protons from enzymatic reactions may account for the wide range of reactions that have been reported for this therapeutic and may account for the non-specific improvement of chronic diarrhea in humans (43).

In previous studies aimed at assessing the mutation frequency of NTZ for *E. coli* in a papillation type assay (LacZ reversions) in which MinA was the base medium, we noted that NTZ concentrations higher than 15 µg/m were inhibitory for growth (38). In contrast, no inhibitory action was observed in nutrient rich LB medium (MIC>64 µg/m), suggesting that NTZ affected some conditionally essential biosynthetic pathway. Given anecdotal reports that NTZ is a nonspecific antidiarrheal drug, we considered the possibility that the drug might affect fitness of enteric pathogens, much like how prophylaxis with bismuth subsalicylate wards off travelers' diarrhea (6). We have investigated the effect of NTZ on EAEC strain 042 that is often used as a model system for the study of biofilm production.

It is disclosed herein the unexpected result that NTZ inhibits biofilm production and hemagglutination at drug concentrations that do not appreciably inhibit growth. Furthermore, our studies reveal that the basis for this inhibition is due to inhibition of fimbrial filament formation and not on the regulation of aafA gene expression. Thus, NTZ, by blocking aggregative behavior of EAEC, might have efficacy in treating enteric diarrheal diseases.

Materials and Methods

Bacterial Strains and Culture Medium.

Enteroaggregative *E. coli* strains 042, 17-2 and JM221 were obtained from the collections of the Center for Vaccine Development, University of Maryland School of Medicine. Strains were cultured in Luria-Bertani (LB) medium or a modified chemically defined MinA medium (MinA-G) containing per liter: 1% glucose, 1 mM $MgSO_4$, 1 g $(NH_2)_2SO_4$, 4.5 g $KH_2PO_4$, 10.5 g $K_2HPO_4$, 0.5 g sodium citrate.

Effect of NTZ on Bacterial Growth and Motility.

EAEC strains were grown overnight in MinA-G medium at 37° C. with shaking and used to inoculate fresh MinA-G medium containing a range of NTZ concentrations (0, 5, 10, 15, 20, and 25 µg/m) to a starting $OD_{600}$ of 0.1. Growth was recorded as the absorbance at 600 nm at 30-minute intervals over a period of eight hours. MIC testing of all strains was done by microdilution in MinA-G medium (0 to 32 µg/m). Motility was assessed in LB soft agar (0.3% agar) containing 0 to 25 µg/m of NTZ. The diameter of outward spreading was measured daily and inhibition computed as percent of control.

Quantitative Biofilm Assay.

A quantitative biofilm assay was used to determine the effect of NTZ on biofilm formation (41). Strain 042 was grown overnight at 37° C. with shaking and inoculated 1:100 in 200 µl culture medium in Costar 96-well, flat-bottom, polystyrene microtiter plates containing appropriate concentrations of NTZ. Plates were incubated statically at 37° C. in a humidified incubator. At 24 h, bacterial growth was measured by either transferring 100 ml aliquots to another microtiter plate to determine turbidity or by diluting 100 µl aliquots 1:100 in 9.9 ml PBS for quantitative plate counts on LB medium. Bacterial counts in triplicate are reported as cfu/ml. Biofilm was visualized following staining with 0.5% crystal violet (41) and the absorbance was read at 570 nm using a microplate reader (Molecular Dynamics). All experiments were in triplicate and reported as mean and standard deviation.

Assays were initially performed with and without 25 µg/ml NTZ using five different growth media: DMEM, DMEM with 0.4% glucose, LB, LB with 0.4% glucose, and our chemically defined medium containing 1% glucose. *E. coli* DH5α served as a negative control for biofilm formation. Assays were then run with increasing concentrations of NTZ (0, 5, 10, 15, 20, 25 µg/ml) both in the chemically defined medium and in DMEM with 0.4% glucose. Denitro nitazoxanide, a biologically inert compound, was used as a negative control, and DMSO was used to control for any hydrophobic effects in adding NTZ (which is prepared as a 25 mg/ml stock solution in DMSO).

Hemagglutination of Red Blood Cells by Whole Bacterial Cells.

Hemagglutination (HA) has previously been shown to correlate with expression of AAF fimbriae by various EAEC strains (3). HA assays were performed in 96-well microplates as described in (1). Bacteria grown over night without shaking (MinA-G medium with and without 25 µg/ml NTZ) were suspended in PBS and diluted to $OD_{660}$ of 1.5, 1.0, and 0.5 and 100 ml was mixed with an equal volume of 3% (vol/vol) sheep erythrocyte suspension containing 1% mannose, except when type I fimbriae producing strains were assayed. In the latter, bacteria were grown statically in LB medium (with and without NTZ) for 48 h and HA was determined with guinea pig erythrocytes. HA reactions were incubated at 4° C. for 20 min. HA was determined visually against controls receiving no NTZ. All assays were prepared in triplicate and repeated twice.

RNA Extraction.

EAEC 042 was grown overnight in MinA-G medium and then diluted to a starting $OD_{600}$ of 0.05 in three 50 ml MinA-G cultures with 0, 10, and 25 µg/ml NTZ. Bacterial cells were grown with shaking until the cultures reached an $OD_{600}$ of ~0.4 and were harvested by centrifugation at 4° C. The pellets were resuspended in 200 µl TE buffer, transferred to polystyrene round bottom 14 ml tubes, and total RNA was extracted by the TES-hot phenol method as previously described (15). The RNA was re-precipitated and washed two times with 500 µl 70% DEPC ethanol to remove any remaining salts. The pellets were dried at 37° C. and suspended in 100 µl DEPC water. RNA concentration was determined with a NanoDrop ND-1000 UV-Vis Spectrophotometer. RNA yields were typically in the 1.6-3.2 µg/µl range. Residual DNA was removed by treatment with TURBO DNase and stored at −80° C. (15).

RT-PCR.

Primers for real-time qRT-PCR were designed to yield approximately 150 base pair amplicons for the virulence genes aggR and aafA and for the stringent response gene rpoS, which served as an internal control. SuperScript™ II Reverse Transcriptase (Invitrogen) was used to synthesize first-strand cDNA from 1 µg purified RNA with 100 ng random primers (Invitrogen). RNA, random primers, and dNTPs (0.5 mM final concentration) were mixed, heated for 65° C. for 5 min, centrifuged briefly, and quick chilled on ice. To each 20 µl reaction was added First-Strand Buffer, DTT (0.01 M final concentration), and 20 U RNase Inhibitor (Applied Biosystems). The contents of the tube were mixed gently and incubated at 25° C. for 2 min. SuperScript™ II RT was added, and the reactions were incubated at 25° C. for 10 min and 43° C. for 50 min followed by heat inactivation of the enzyme at 70° C. for 15 min. Each reaction was diluted by adding 80 µl DEPC water.

PCR of the three genes was performed for each of the three cDNA reactions in an iCycler Thermal Cycler with SYBR Green as the detection agent. Each 25 µl reaction consisted of 10 µl of diluted cDNA, 1×PCR Buffer (containing 1.5 mM $MgCl_2$), 0.5× Q-Solution, 4 mM $MgCl_2$, 0.2 mM dNTP mix, 0.05 µg each forward and reverse primers, 1.25 U HotStarTaq DNA Polymerase (QIAGEN), and 0.25 µl of SYBR Green (diluted $10^{-3}$). Reactions were incubated for 15 min at 95° C. to activate the HotStarTaq DNA polymerase, followed by 35 amplification cycles of 95° C. for 30 sec, 58° C. for 30 sec (optimized by gradient PCR of genomic DNA), and 60° C. for 20 sec, with a final 10 min 60° C. extension. Following PCR, the temperature was increased in 0.5° C. increments every 10 sec to generate melt curves of PCR amplicons. To account for any amplification due to contaminating genomic DNA, PCR reactions with RNA, corresponding to the concentration used for cDNA synthesis, served as negative controls for each sample. All reactions were performed in triplicate. Repeated trials were conducted to optimize RNA purification and PCR conditions and to verify the reproducibility of the results.

Reporter Gene Fusions.

Reporter gene fusions were provided by James Nataro (University of Maryland) and included *E. coli* 042aggR-lacZ and *E. coli* 042 aafA-phoA (3.4.14 and 2.94) (3) and an undefined promoterless lacZ control strain of *E. coli* 042. Strains were grown without shaking in MinA-G medium supplemented with 0, 12 or 25 µg/m of NTZ for 16 h at 37° C. β-Galactosidase activity was determined spectrophotometrically and reported in Miller units (24). Alkaline phosphatase activity was also determined spectrophotometrically using p-nitrophenol as previously described (23). All assays were performed in triplicate in three independent experiments and the mean and standard deviation are reported.

Purification and Analysis of Fimbrial Proteins by SDS-PAGE.

A simplified procedure for mechanical removal of fimbriae was modified from Dodd and Eisenstein (5). EAEC 042 was grown in MinA-G medium and LB overnight and inoculated 1:100 in 100 ml of the appropriate culture medium in 250 ml flasks with and without 25 µg/m of NTZ and grown statically overnight at 37° C. The cultures were spun down at 4,000 rpm for 5 min at 25° C. Pellets were resuspended in 2 ml PBS, vortexed 2× for 30 sec to shear off flagella and fimbriae, and then centrifuged at 8,000 rpm for 10 min to remove whole cells. The supernatants, containing fimbrial filaments, were transferred to new tubes, and 8 ml of acetone were added to precipitate proteins. Solutions were spun down again at 8,000 rpm for 10 min, and the acetone was decanted. The remaining protein pellets were resuspended in 50 µl PBS and 100 µl 3× loading buffer containing 2-mercaptoethanol.

Biofilms were observed at the air-liquid interface in LB culture and at the bottom of the flask in MinA-G without NTZ. To analyze the proteins contained in the biofilm, the flasks were rinsed with water to remove residual bacteria, and the biofilms were dissolved in 1-2 ml 1% SDS. 50 µl of each solution was combined with 100 µl 3× loading buffer in PCR tubes. All five samples were run in a NuPAGE 4-12% Bis-Tris gel at 120 V and stained with Coomassie brilliant blue or used directly for transfer of proteins to nitrocellulose.

Immunoblot and Immunofluorescence.

Ponceau red stained nitrocellulose was used to visualize transferred proteins and immunoblotting protocols used in this study as described (14). Hyperimmune rabbit serum raised against AafA fimbrial subunits of EAEC strain 042 was used at a dilution of 1/10000. Alkaline phosphatase conjugated goat anti-rabbit IgG (1/5000) was used with BCIP-NBT to identify immunoreactive proteins. For assessing fimbrial expression by immunofluorescence, bacteria were briefly heat fixed onto microscope slides and treated 1 min with 2% paraformaldehyde. Following treatment with anti-AafA serum for 30 min, slides were washed 3× with PBS and stained with rhodamine-conjugated goat anti-rabbit immunoglobulin. The slides were washed 3× in PBS, dried and visualized with a Zeiss epi-fluorescence microscope.

Statistical Analysis.

SigmaStat software was used to perform statistical analyses of data acquired from biofilm assays and qRT-PCR.

Results

NTZ Partly Inhibits Growth of EAEC 042.

Figure 9A:
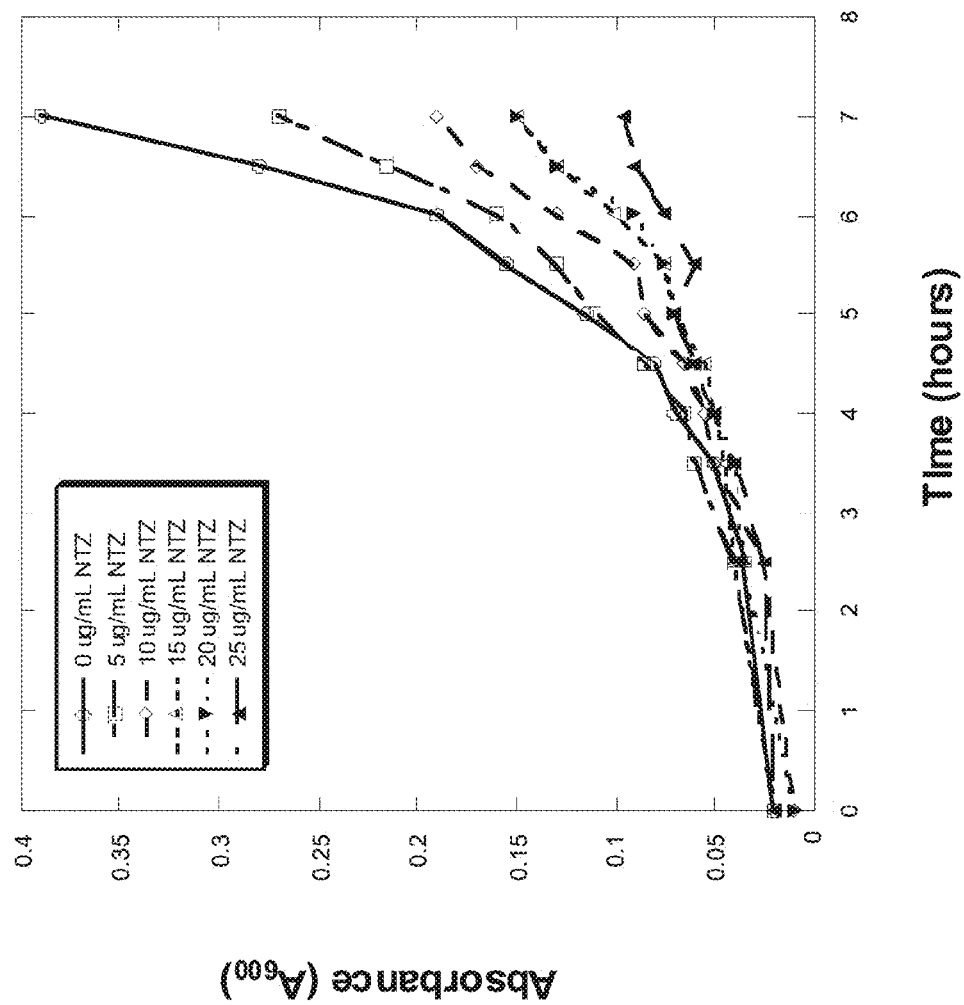
FIG. 9. Bacterial growth in MinA-G medium. A. AAFA/I EAEC strain 042 and B. AAFA/II EAEC strain 17-2 were grown in liquid culture supplemented with NTZ at the concentrations indicated in the legend.
Figure 9B:
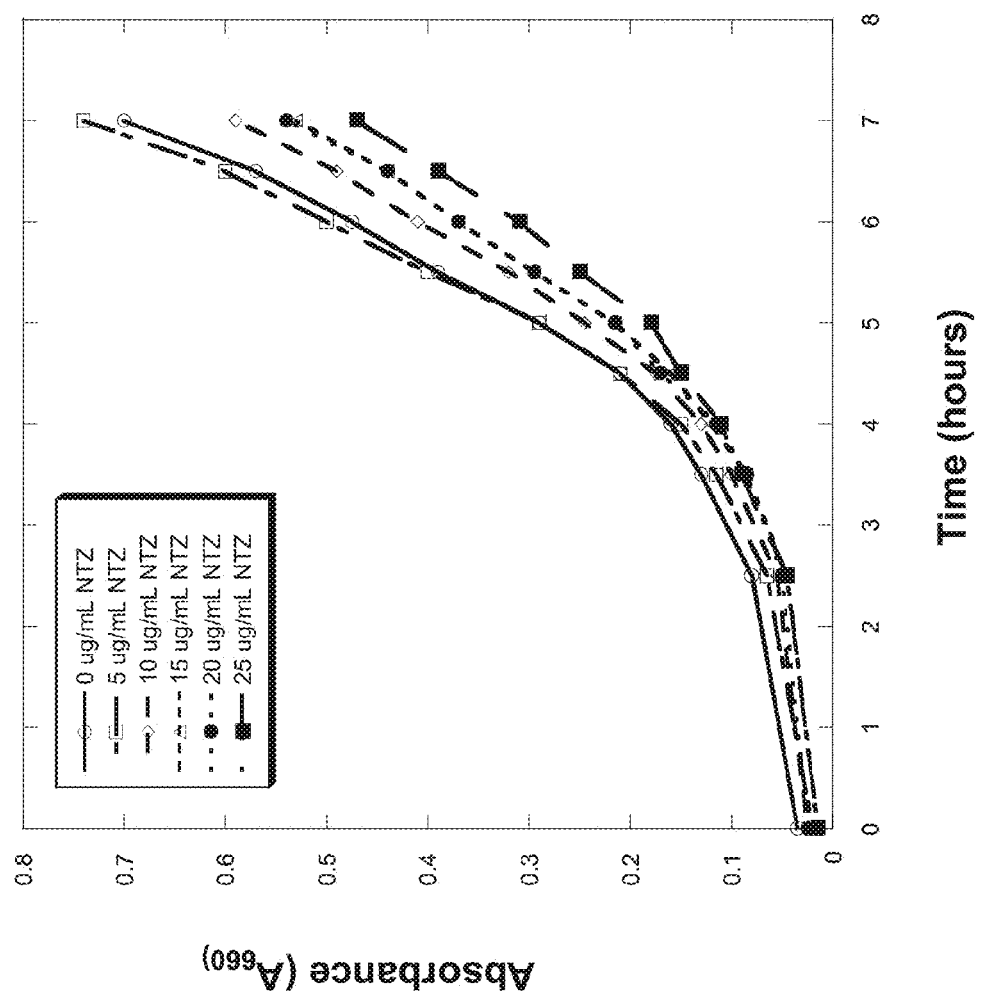

We previously reported that the antiparasitic drug NTZ partly inhibited the growth of *E. coli* strain CC 104 on MinA-G medium but not on LB (38). MIC testing under static conditions indicated that for LB medium, the MIC was >64 µg/m; while for MinA-G it was ~32 µg/ml. We reasoned that if the human intestine resembled the MinA-G medium nutritionally (i.e., nutrient poor) as opposed to nutrient rich LB medium, then perhaps NTZ might show some efficacy against these organisms (35). To test this hypothesis, we reproduced growth experiments with the EAEC 042 (AAF/II) and 17-2 (AAF/I) strains which are typical of strains causing persistent diarrhea. NTZ and the deacetylated metabolite tizoxanide inhibited aerobic growth of EAEC 042 (FIG. 9) and to a lesser extent 17-2 in a dose dependent manner in the MinA-G medium (only data with NTZ are shown). While growth was not completely inhibited at concentrations up to 25 µg/ml, we estimated that 50% inhibition could be achieved at NTZ concentrations between 15 to 20 µg/ml for the 042 strain and 20 to 25 µg/ml for the 17-2 strain. Under static conditions, EAEC strains exhibited a $MIC_{50}$ of ~20 µg/ml. Such concentrations are achievable clinically where doses of 1 g per day are used to treat parasitic infections (8, 13).

NTZ Inhibits Biofilm Formation.

Figure 10:
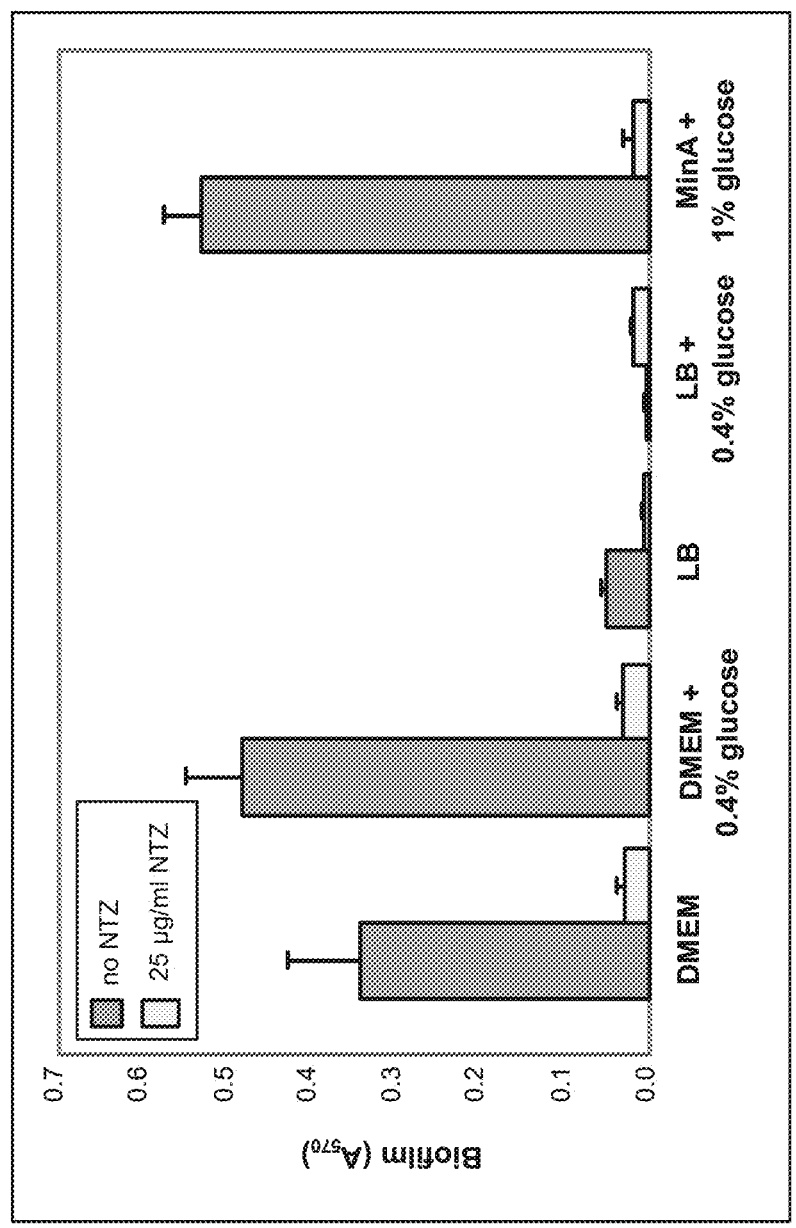
FIG. 10. Medium composition on biofilm production. Biofilm accumulation was determined in DMEM and LB medium (±0.4% glucose) and MinA-G medium (±1% glucose) with EAEC strain 042 in the presence or absence of 25 µg/m NTZ. Biofilm accumulation was quantified by the crystal violet assay. All assays were performed in triplicate.
Figure 11:
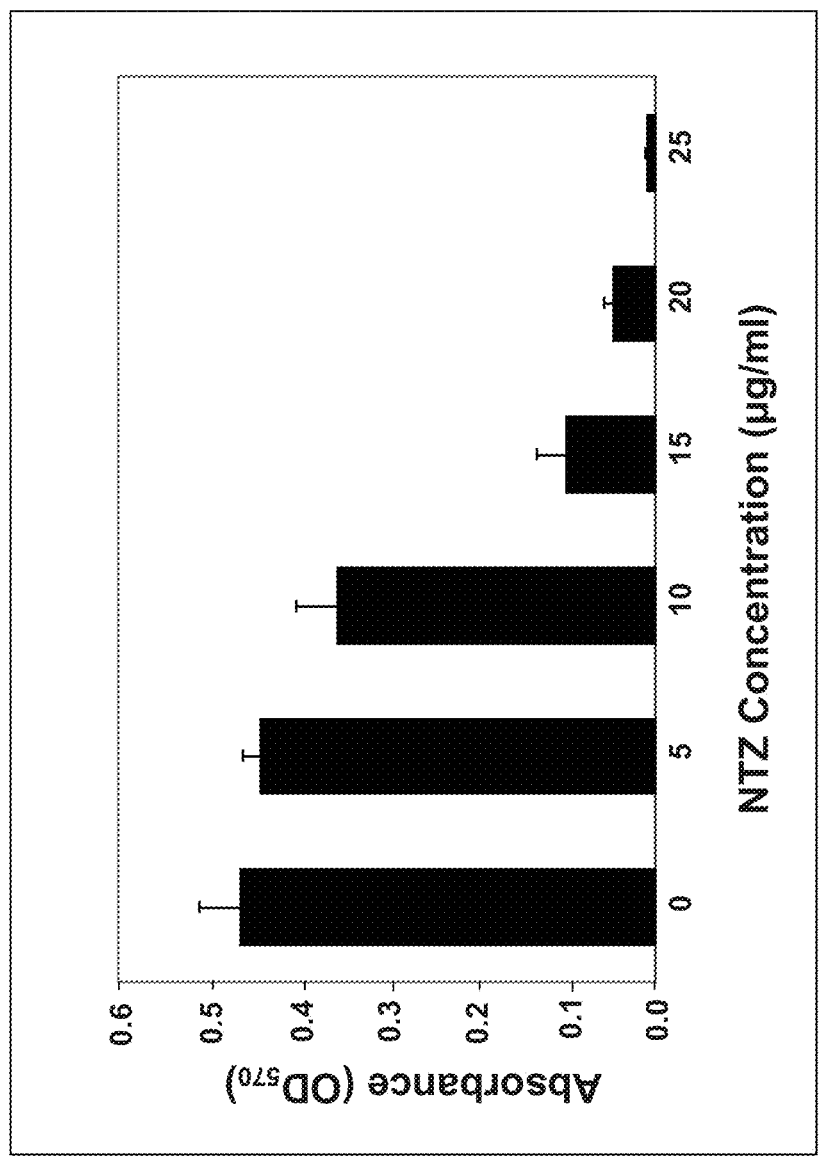
FIG. 11. Dose dependent inhibition of biofilm formation. EAEC strain 042 grown in MinA-G medium supplemented with the indicated concentrations of NTZ. All assays were performed in triplicate.

In MIC testing performed by microdilution, we noticed that EAEC strain 042 formed a biofilm in the plastic wells in MinA-G medium and that sub-MIC levels of NTZ inhibited biofilm production. It has been suggested that the presence of an EAEC mucosal biofilm correlates with infectivity by promoting persistent colonization and increasing resistance to antibiotics (25). Both biofilm and aggregative adherence behavior are attributable to expression of AAF/II fimbriae (41). To explore the effect of NTZ further, we compared biofilm formation in the MinA-G medium with that in DMEM and LB media. As seen in FIG. 10, EAEC biofilms (042 strain but not 17-2 or JM221 strains) were densest in the MinA-G medium ($OD_{570}$>0.5) and absent in LB ($OD_{570}$<0.01), consistent with previous findings that demonstrated higher biofilm expression in high-glucose media (37). Repeated assays in MinA-G medium revealed a dose dependent inhibition of biofilm formation with NTZ. Inhibition was most dramatic between 10 and 15 µg/ml, with almost complete inhibition at 20 µg/m (FIG. 11). Analogous assays with DMEM+0.4% glucose yielded comparable results but with lower overall biofilm density and a more steady decrease in response to increasing NTZ dose (data not shown). Plate counts from aliquots at every drug concentration revealed high bacterial density (>$10^8$ cfu/ml) in all wells, indicating that bacteria were in stationary phase by 24 h post inoculation. Thus, biofilm reduction was not due to inhibition of growth.

NTZ Inhibits Hemagglutination.

Both AAF/II and AAF/I fimbriae-producing strains hemagglutinate erythrocytes, and this was confirmed with sheep erythrocytes. As seen in Table 2, NTZ inhibited HA by both strains of EAEC, suggesting a common inhibitory mechanism. Moreover, similar concentrations of NTZ (20 µg/m) inhibited HA by EAEC strain JM221 grown statically in LB medium which promotes expression of type I fimbriae and represses AAF fimbriae. The distinction was further demonstrated by the ability of LB grown JM221 (but not MinA-G grown) to hemagglutinate guinea pig erythrocytes, but not sheep erythrocytes. The inhibitory action of NTZ on production of type I fimbriae in LB medium (MIC>64 µg/m), supports the likelihood of a specific target rather than a nonspecific growth related mechanism.

TABLE 2

Hemagglutination assay.

| Bacterial Strains | NTZ | 1.5 | 1.0 | 0.5 |
|---|---|---|---|---|
| | | HA (sheep erythrocytes)[a] Bacterial $OD_{660}$ | | |
| EAEC 042 | − | +++ | ++ | + |
| EAEC 042 | + | + | − | − |
| EAEC JM221 | − | +++ | ++ | − |
| EAEC JM221 | + | ++ | − | − |
| | | HA (guinea pig erythrocytes)[b] | | |
| EAEC JM221 | − | +++ | ++ | ++ |
| EAEC JM221 | + | + | − | − |

[a]Hemagglutination assays were performed in 96 well microplates in triplicate. +++ = strong hemagglutination reaction, + weak and − no hemagglutination. NTZ + indicates that the bacteria were grown over night in MinA-G medium supplemented with 20 µg/ml of NTZ.
[b]For determination of hemagglutination by Type 1 fimbriae, bacteria were grown statically in LB broth for 48 h in the presence (+) or absence (−) of NTZ (20 µg/ml). LB grown bacteria do not hemagglutinate sheep erythrocytes indicating the absence of AAF fimbriae. The bacterial OD used are as indicated for sheep erythrocytes.

NTZ Inhibits Fimbrial Filament Assembly.

Figure 12:
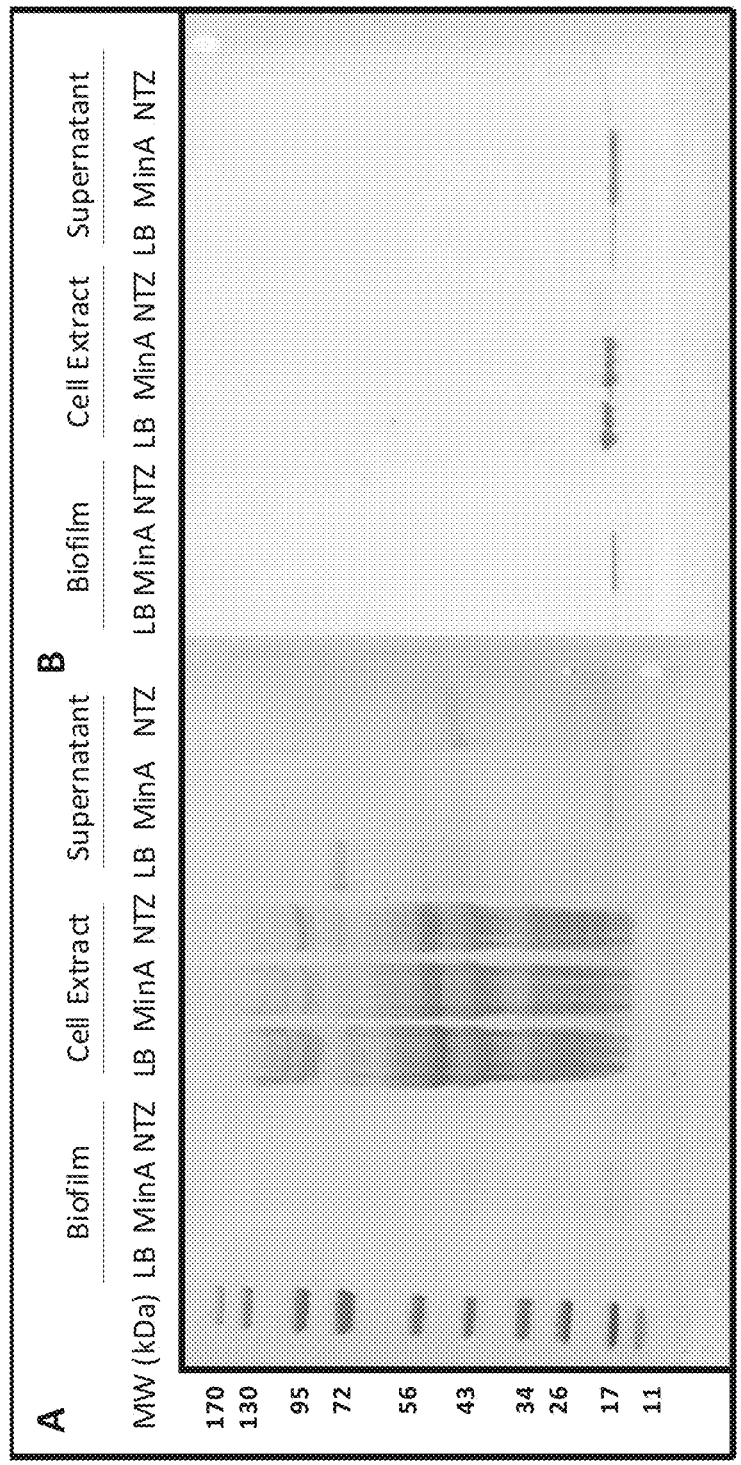
FIG. 12 (A and B). Inhibition of pilin assembly by NTZ. Pilin was collected from whole cells following vortexing and centrifugation followed by TCA precipitation as described in the text. Ponceau stain (A) and immunoblot (B) of SDS-PAGE of extracts prepared from bacteria grown statically in MinA-G, MinA-G+NTZ (20 µg/m) and from LB medium.

Both the aggregative adherence phenotype and biofilm formation by EAEC 042 are attributable to the production of AAF fimbriae and not to production of polysaccharides (30). While both EAEC strains produce AAF fimbriae, only fimbriae from the 042 strain adhere to plastic. Thus, the inhibition of biofilm formation and HA by NTZ must be due to the absence of surface filaments on the EAEC strains. To distinguish between fimbrial gene expression and assembly, we first determined if fimbriae were indeed absent on NTZ treated EAEC 042 bacteria by immunoblot of whole bacteria subjected to vortexing to shear off filaments. As seen in FIG. 12 (A—protein stain and B—immunoblot), intact filaments were obtained from bacteria grown statically in MinA-G medium without NTZ (supernatants). Fimbrial subunits were also detected in cell free extracts that would represent both monomers and filaments and in biofilm scrapings from plastic wells that would represent filaments. In contrast, filaments obtained by vortex (FIG. 12B, supernatants) of LB grown bacteria were much less abundant as previously confirmed (35, 37), though fimbrial subunits were detected in cellular extracts and to a much lesser extent from surface ring material extracted from wells of microtiter dishes. At 20 µg/ml, NTZ inhibited biofilm formation in MinA-G medium and fimbrial filaments were nearly absent from vortexed whole cells (much less than observed for LB-grown bacteria). No fimbrial subunits were detected in cellular extracts, which might suggest that NTZ might affect gene expression. While not depicted, indirect immunofluorescent assays with whole cells were consistent with the immunoblot results. These findings suggest that NTZ affects the production of AafA filaments by either repressing aafA gene expression or by inhibiting some step in AafA assembly.

NTZ does not Affect aafA Expression.

Figure 13:
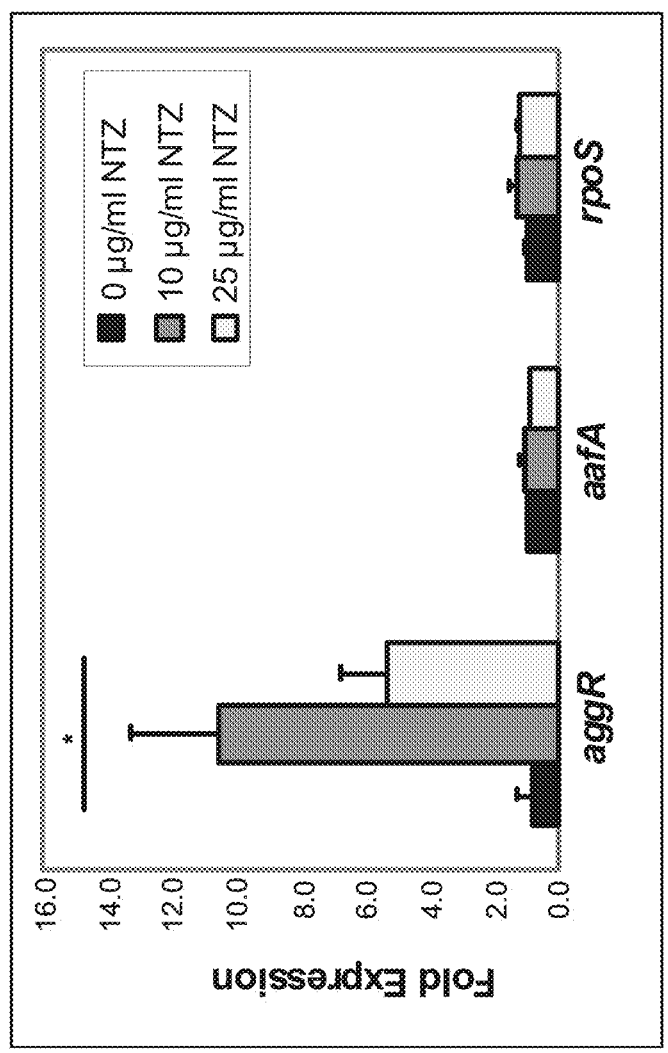
FIG. 13. qRT-PCR of aggR, aafA, and rpoS. Total RNA was prepared from EAEC strain 042 grown in MinA-G medium at the indicated concentrations of NTZ. Assays were performed in triplicate and relative fold expression is indexed to aggR equal to 1 in the absence of drug.
Figure 14A:
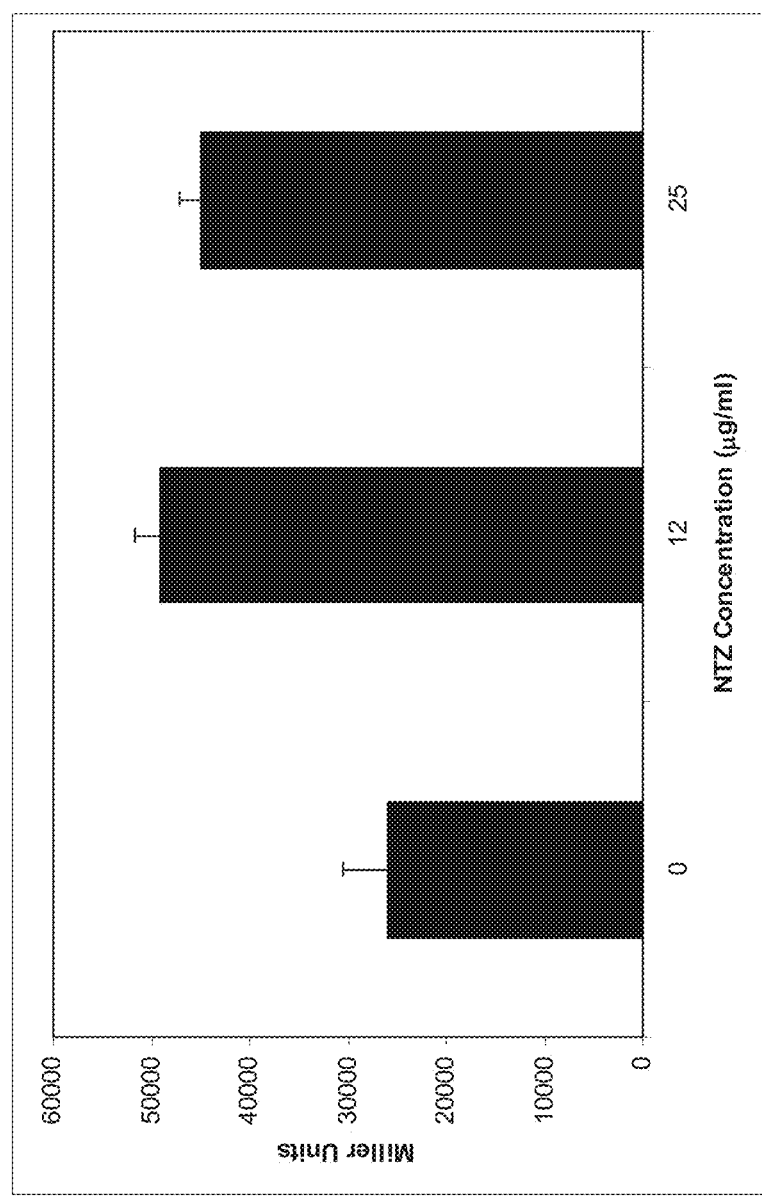
FIG. 14 (A and B). Expression of reporter fusions. A. β-galactosidase activity of aggR-lacZ fusion in response to different concentrations of NTZ. B. PhoA activity of aafA-phoA fusions in response to different concentrations of NTZ.
Figure 14B:
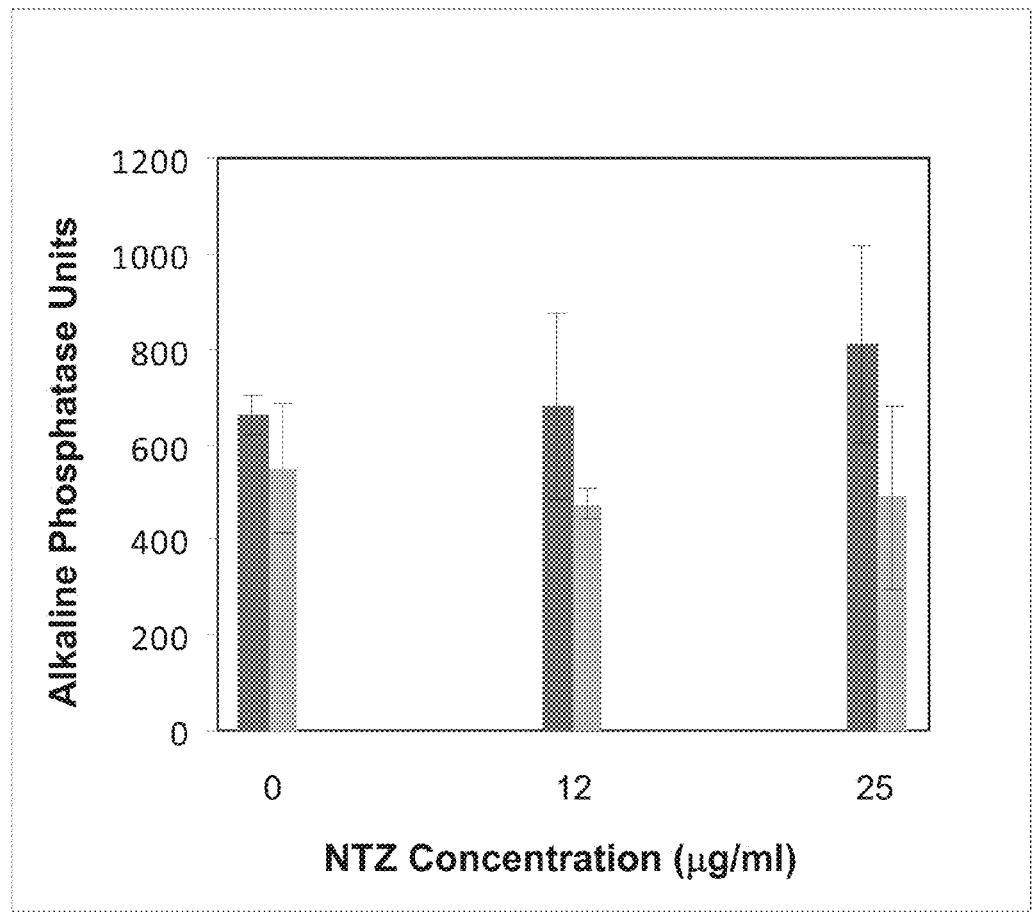
Figure 15:
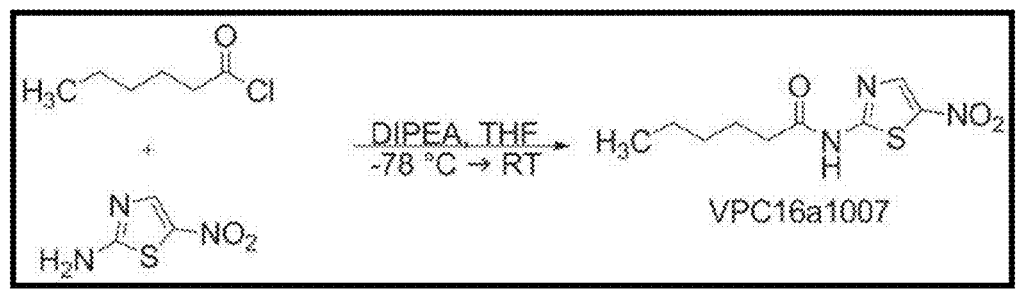
FIG. 15. Scheme for Aliphatic Derivatives of 2-amino-5-nitrothiazole.
Figure 16A:
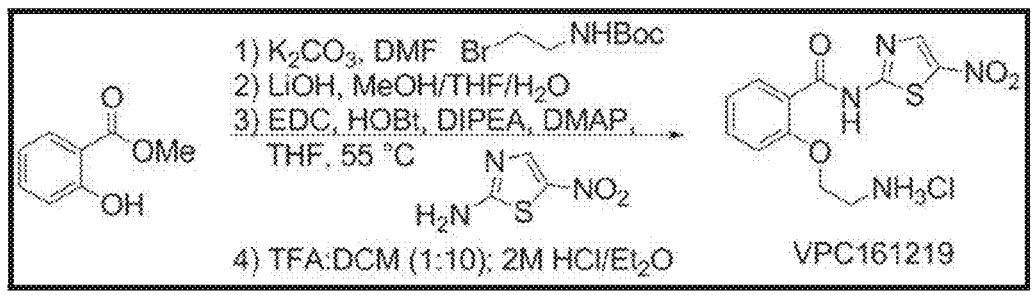
FIG. 16 (A, B, and C). Scheme for Aliphatic Amine Analogues of 2-amino-5-nitrothiazole FIG. 17. Scheme for Amino Acid Analogues of 2-amino-5-nitrothiazole FIG. 18. Scheme for Anthranilic Analogues of 2-amino-5-nitrothiazole FIG. 19. Scheme for Pyridine Analogues of 2-amino-5-nitrothiazole FIG. 20. Scheme for Indole Analogues of 2-amino-5-nitrothiazole FIG. 21. Scheme for Carboxylic Acid Analogues of 2-amino-5-nitrothiazole FIG. 22. Scheme for Dimer-like Analogues of 2-amino-5-nitrothiazole FIG. 23. Scheme for Halide Analogues of 2-amino-5-nitrothiazole FIG. 24. Scheme for Monosubstituted Analogues of 2-amino-5-nitrothiazole FIG. 25 Scheme for Disubstituted Analogues of 2-amino-5-nitrothiazole FIG. 26 (A, B, C, and D). Scheme for Furan Analogues of 2-amino-5-nitrothiazole FIG. 27 (A, B, and C). Scheme for Thiophene Analogues of 2-amino-5-nitrothiazole FIG. 28. Scheme for Amide Isosteres of 2-amino-5-nitrothiazole FIG. 29. Scheme for Analogues of 2-amino-4-chloro-5-nitrothiazole FIG. 30 (A, B, and C). Scheme for Analogues of 2-amino-3,5-dinitrothiophene For FIGS. 15-30, those schemes generating lead compounds are highlighted in bold boxes, i.e., FIGS. 15, 16, 19, 25, 26, 27, 29, and 30. Schemes for analog and derivative generation are further provided in Tables 3-18.
Figure 16B:
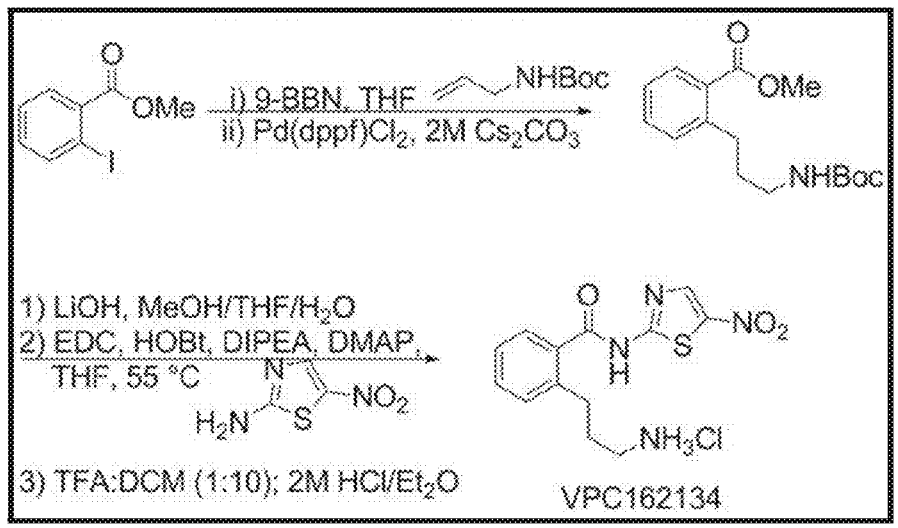
Figure 16C:
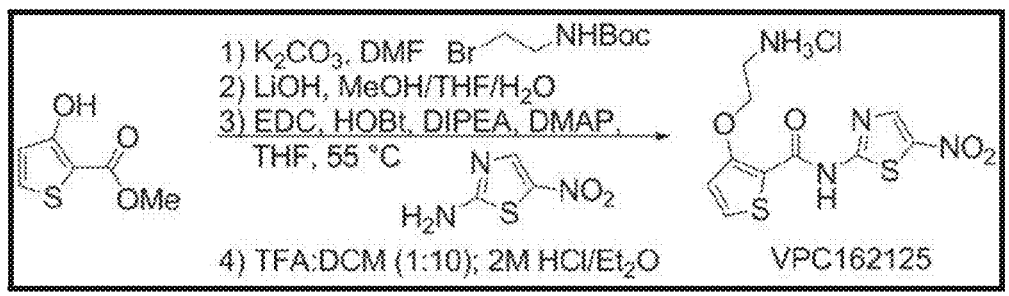
Figure 17:
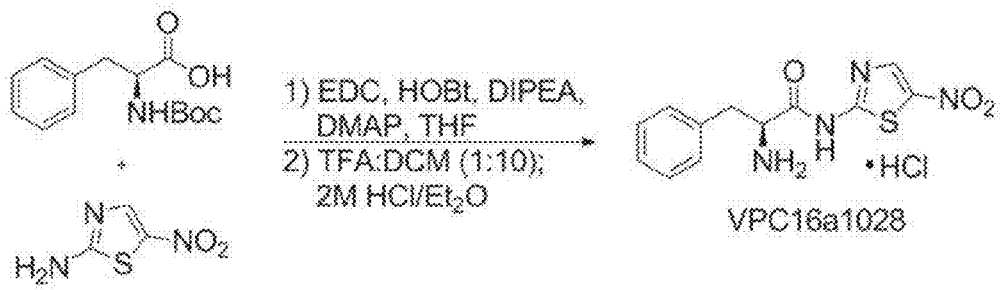
Figure 18:
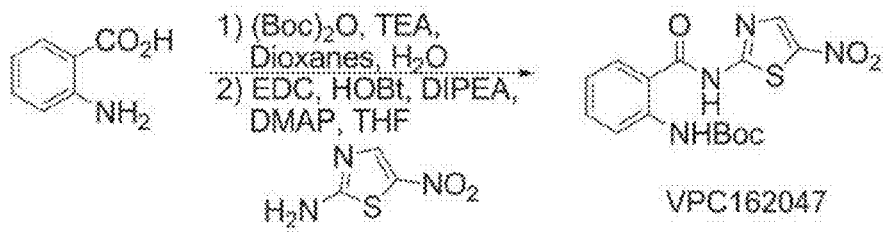
Figure 19:
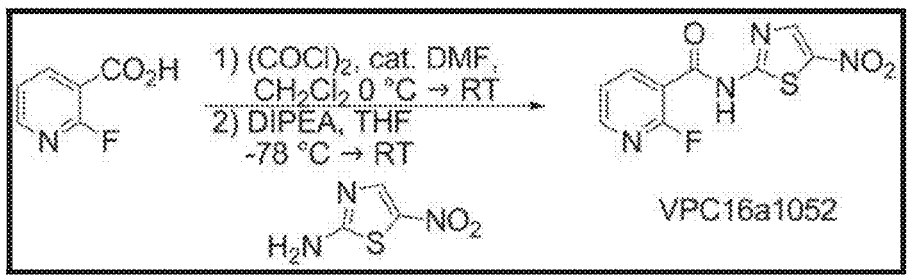
Figure 20:
Figure 21:
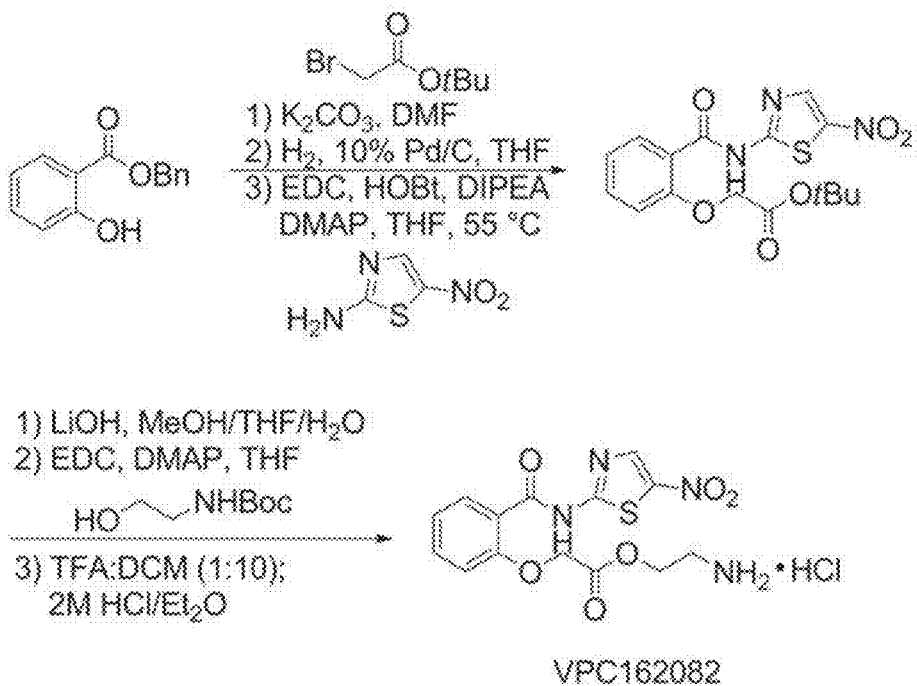
Figure 22:
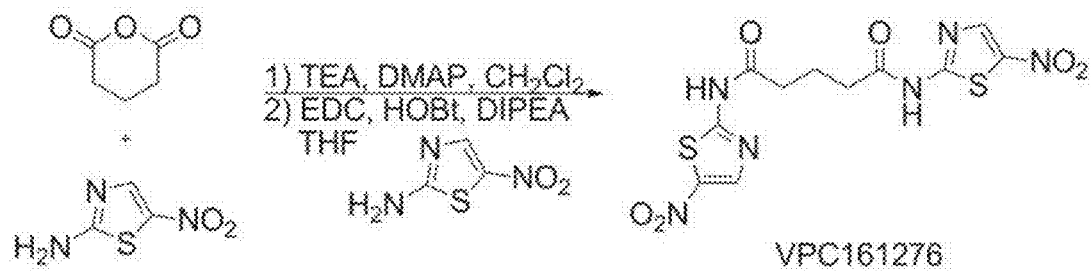
Figure 23:
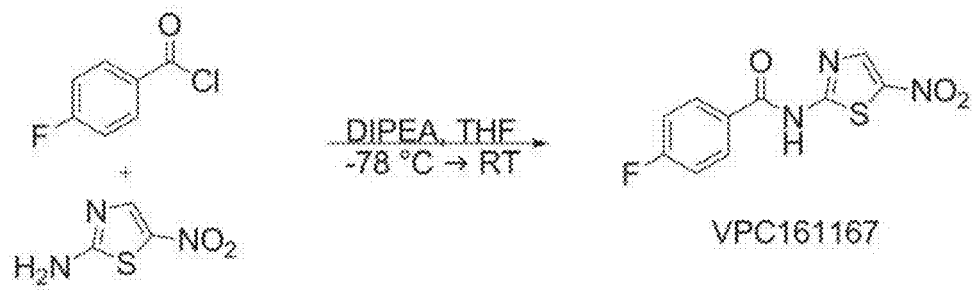
Figure 24:
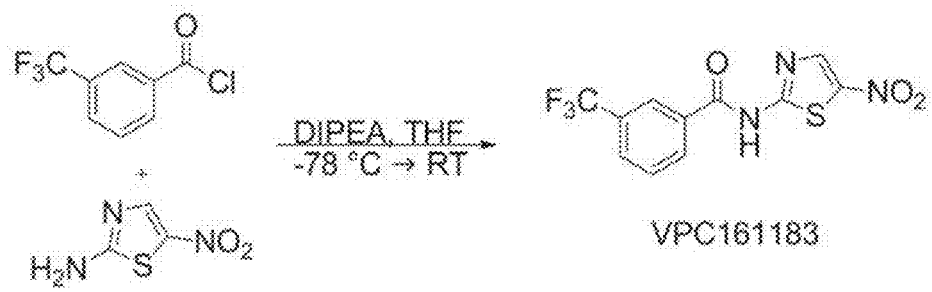
Figure 25:
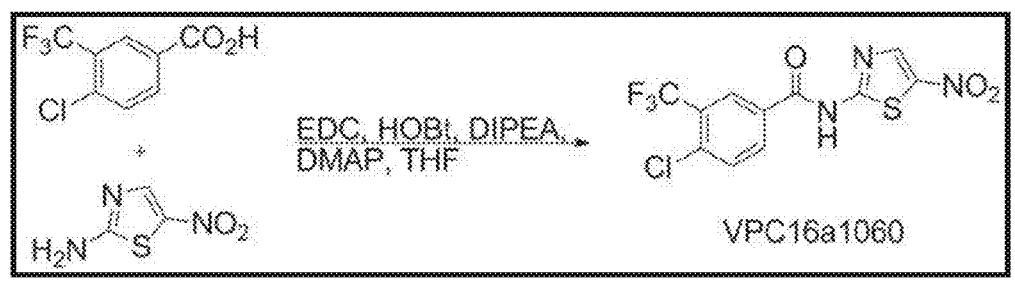
Figure 26A:
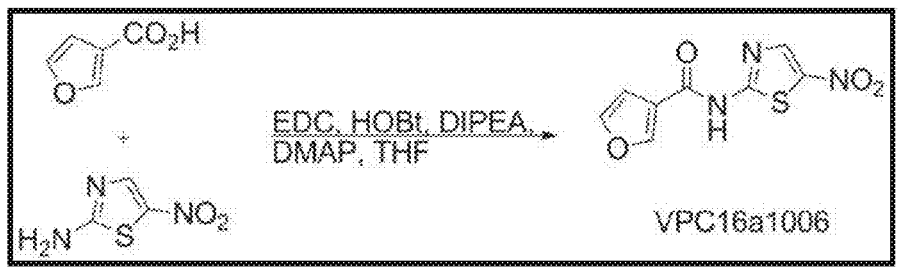
Figure 26B:
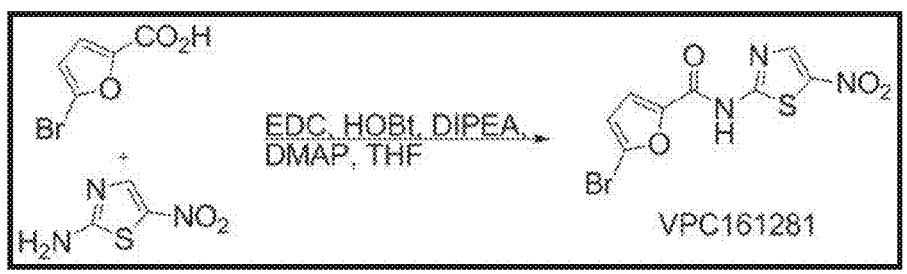
Figure 26C:
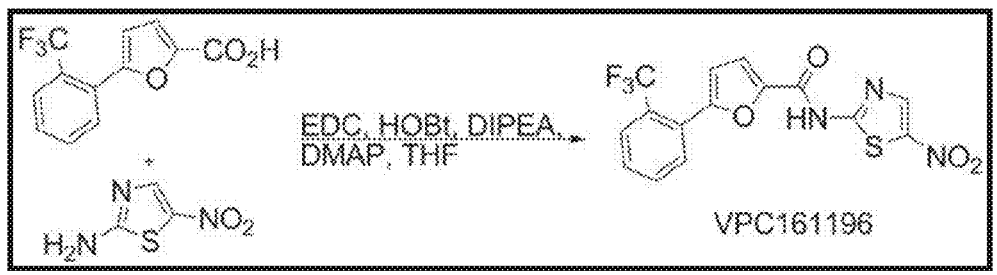
Figure 26D:
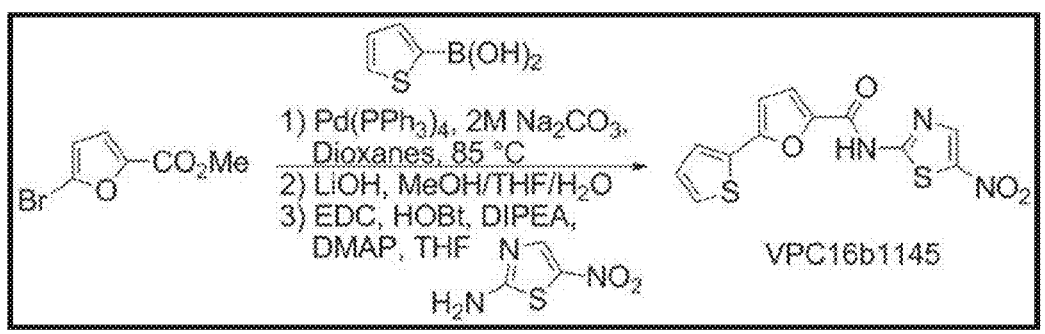
Figure 27A:
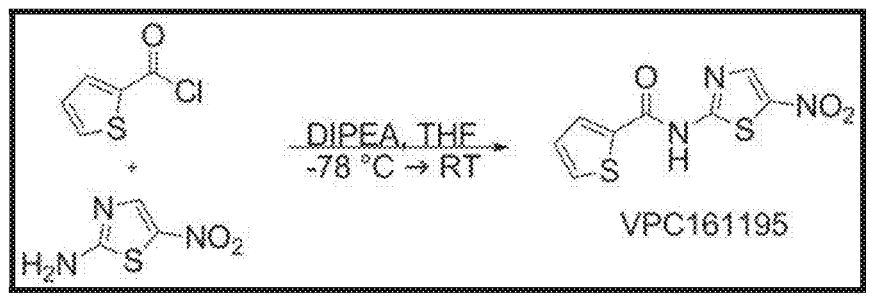
Figure 27B:
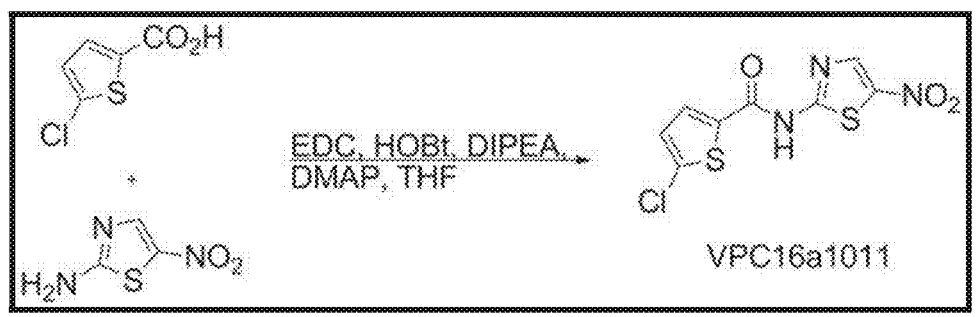
Figure 27C:
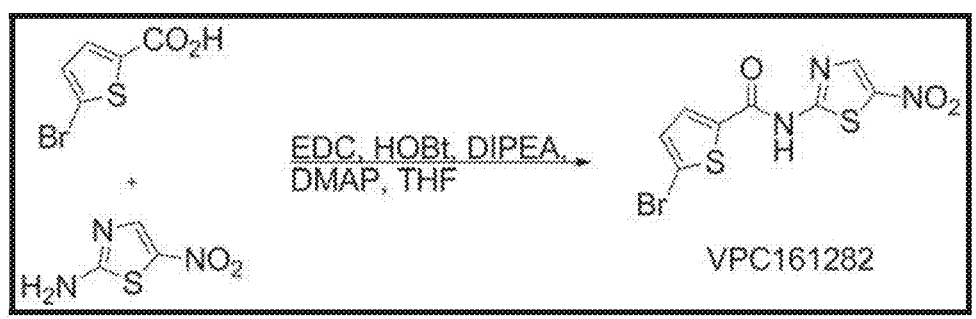
Figure 28:
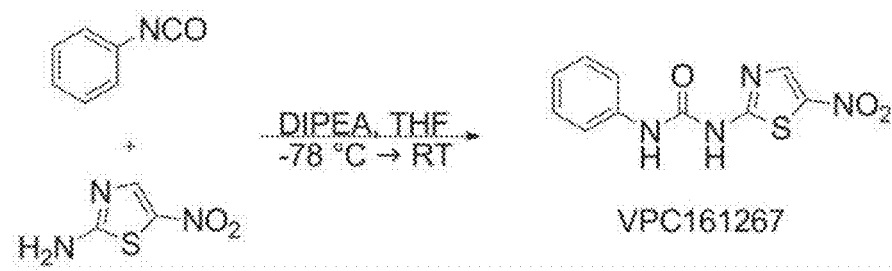
Figure 29:
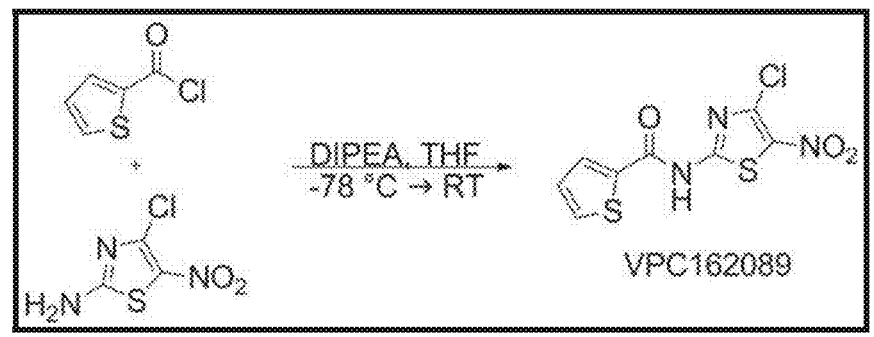
Figure 30A:
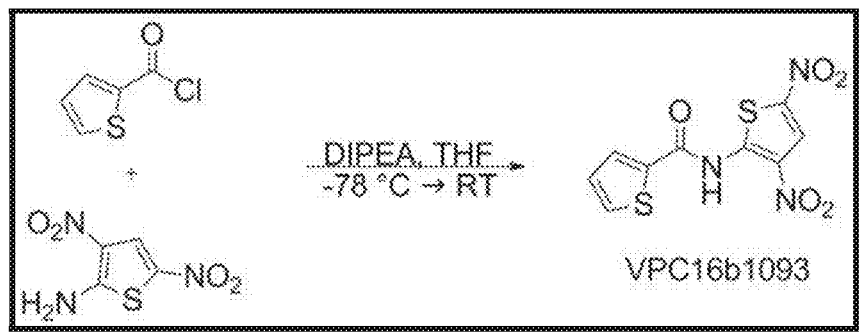
Figure 30B:
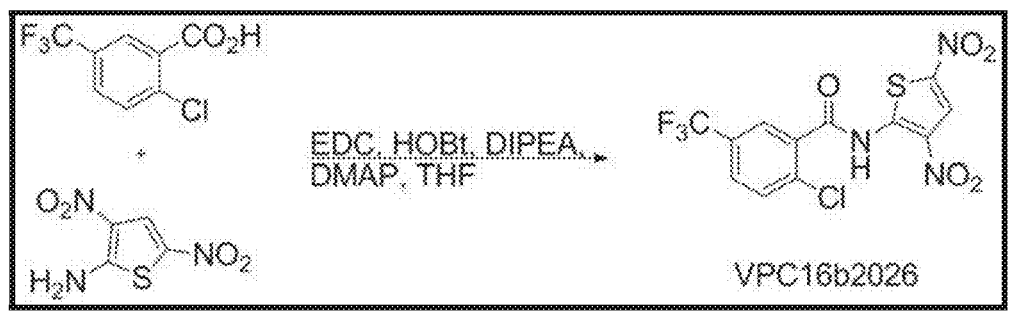
Figure 30C:
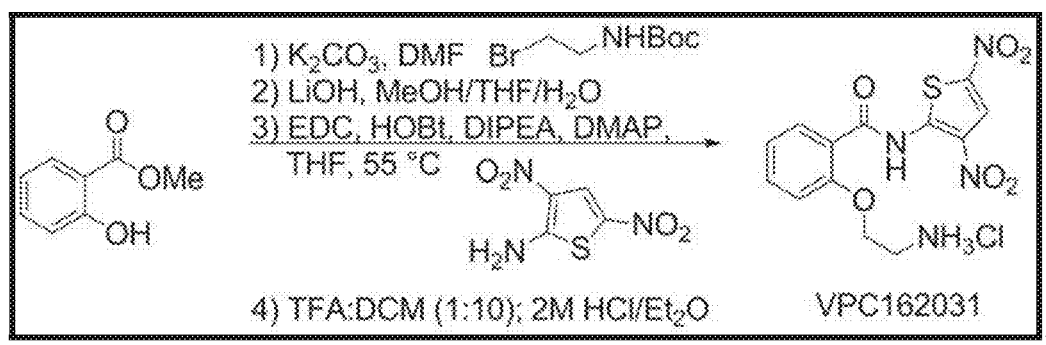

To determine whether NTZ affected aafA gene expression, real-time qRT-PCR was used to monitor aggR and aafA transcript levels in bacteria grown with gentle shaking in MinA-G medium with and without NTZ. The stationary phase sigma factor gene rpoS served as an internal control in qRT-PCR. As seen in FIG. 13, aafA expression was unaffected by NTZ: a Kruskal-Wallis One Way ANOVA on Ranks ($\alpha$=0.05) found no statistically significant difference in aafA expression (P=0.086) or in rpoS expression (P=0.086) in the presence or absence of NTZ. However, the drug caused a 10-fold increase in expression of aggR (P=0.002, One Way ANOVA). The NTZ induced increase in aggR expression could also be demonstrated with lacZ reporter fusions as depicted in FIG. 14A. $\beta$-galactosidase assays showed a similar increase in aggR gene expression (~2.5-fold) with cells grown statically in the presence of 12 µg/ml NTZ and a slight decrease with cells grown at 25 µg/ml. In contrast, aafA expression, as monitored by PhoA activity, was consistent with the qPCR findings that NTZ treatment did not alter aafA gene expression when compared to untreated controls (see FIG. 14B). The qRT-PCR and reporter fusion results indicate that NTZ does not affect aafA gene expression. The up-regulation of argR and not aafA might suggest a requirement for additional regulatory factors for activation of aafA.

NTZ does not Affect Bacterial Motility.

Since disulfide bond formation is required for fimbrial assembly into filaments (20, 33), we considered the possibility that DsbA, a periplasmic protein that catalyzes this reaction, might be a potential target of NTZ action based on previous reports of NTZ binding to related enzymes (13). Since DsbA function is also required for assembly and function of flagella, we examined NTZ treated bacteria for motility. Wet mounts of bacteria grown in MinA-G medium with and without NTZ retained motility as viewed by phase contrast microscopy and NTZ concentrations that inhibited biofilm formation had no effect on swarming motility in soft agar chemotaxis assays (data not presented). NTZ concentrations at the MIC did affect swarming, but this was attributed to inhibition of bacterial growth. The motility results are consistent with the aafA::phoA fusion studies (DsbA is required to activate PhoA) and indicate that NTZ is not an inhibitor of DsbA function.

Discussion

In this study, we report that the antiparasitic drug nitazoxanide and its deacetylated metabolite tizoxanide inhibit biofilm production by EAEC strain 042, and HA by both biofilm producing and non-producing strains, when cultured under conditions that promote biofilm formation and that are permissive for bacterial growth. MinA-G was generally superior to DMEM-G in promoting biofilm production and little biofilm was produced in nutritionally rich LB medium. Since biofilm formation is due to the production of aggregative adhesion fimbriae (AAF), we showed by immunoblot and immunofluorescence that the abundance of intact fimbrial filaments recovered from NTZ-treated bacteria was dramatically reduced over controls, suggesting that NTZ inhibited filament biogenesis. AafA levels in cell-free extracts from NTZ treated bacteria were undetectable, consistent with previous reports that unassembled monomers are rapidly degraded (18). Gene expression studies (qRT-PCR and reporter gene fusions) of EAEC 042 bacteria treated with $IC_{50}$ doses of NTZ, showed no change in expression of the aafA gene over controls, while its regulator aggR was increased several fold. The up regulation of aggR might reflect feedback signaling associated with biofilm permissive environmental conditions resulting from drug action; whereas, the absence of increased synthesis of AafA subunits might indicate negative feedback from aborted AafA assembly and protein turnover possibly mediated by extracytoplasmic sigma factors. Alternatively, additional regulatory elements are required in addition to AggR to activate aafA gene expression. While the inhibitory effect of NTZ on EAEC growth in MinA-G medium likely results from the cumulative effects on multiple biosynthetic targets, the profound effect on AAF assembly, a recognized virulence determinant, might be expected to affect colonization and severity of disease. Further in vivo studies in animal models would be required to determine if loss of aggregative adherence is sufficient to reduce infection, persistence and severity of diarrhea.

The AAF fimbrial group is plasmid encoded type IV bundle filaments that utilize the periplasmic chaperone-membrane usher system for monomer assembly into filaments (1). Other required activities include disulfide bond formation in AafA monomers by DsbA and filament dispersal on the surface by an outer membrane dispersin protein (20, 40). The DsbA thiol:disulfide oxidoreductase plays an essential role in facilitating formation of disulfide linkages in many extracellular proteins, including fimbrial antigens and flagellin in which this bond stabilizes the major structural subunits that are required for assembly (33, 42). While DsbA represents an attractive target for the inhibitory action of NTZ, the drug had no effect on bacterial motility or on PhoA activity, which are dependent on DsbA function (42). Our studies suggest that NTZ inhibits fimbrial filament assembly at a later step, perhaps by inhibiting chaperone or usher functions as noted for the PilD chaperone in urogenic E. coli (1, 31, 33). This mechanism is further supported by our finding that NTZ also inhibits HA by EAEC strains that do not adhere to plastic and by EAEC strains expressing type 1 fimbriae. The term pilicide has been coined for small molecule inhibitors of filament biogenesis (31). Several classes of inhibitors have been found to interact with the immunoglobulin-like PapD chaperone of the uropathogenic E. coli P pili system to block chaperone-usher function (31). Our studies do not rule out interference with other steps in the process such as secretion or processing of prepilin or perhaps assembly of pilin monomers. The anionic form of NTZ appears to be required for biological activity as the denitro form of NTZ does not inhibit biofilm formation. Further study is required to identify the underlying molecular mechanisms of NTZ action.

Most gut flora are non-adherent and metabolically adapted to the available nutrient menu. Enteric pathogens, on the other hand, tend to become directly adherent via fimbriae or adherent as part of invading epithelial tissue, but regardless of strategy, their action tends to promote inflammation, which through serum leakage provides amino acids and sugars—a more growth permissive diet. In the case of EAEC, infection is believed to result from initial attachment by aggregative adhesins, displacement of resident flora, elaboration of various toxins that induce inflammation and production of biofilm that promotes clonal persistence by the organisms (28). Pilicides, by inhibiting microbial adherence to gut epithelial cells should dramatically reduce colonization efficiency. In this regard, NTZ should have efficacy against enteric pathogens whose infection strategy is dependent on adherence through fimbrial adhesins.

We demonstrate here that NTZ, an FDA approved antidiarrheal drug, inhibits biofilm formation by impairing a key step in EAEC's pathogenesis and offers a novel approach to combating an increasingly prevalent enteric pathogen that is highly and variably resistant to many antibiotics. NTZ does not kill EAEC but inhibits filament assembly associated with mucosal biofilm that plays a critical role in helping the bacteria to colonize the intestine and compromise the host's immune defense. NTZ could serve as a single knockout of the three primary enteric pathogens that cause repeated or prolonged diarrheal illness among children in the developing world and could significantly allay the burden of diarrhea-associated morbidity.

BIBLIOGRAPHY

Example 2

1. Boisen, N., C. Struve, F. Scheutz, K. A. Krogfelt, and J. P. Nataro. 2008. New adhesion of enteroaggregative *Escherichia coli* related to the Afa/Dr/AAF family. Infect. Immun. 76:3281-3292.
2. Clarke, S. C. 2001. Diarrhoeagenic *Escherichia coli*—an emerging problem? Diagn. Microbiol. Infect. Dis. 41:93-98.
3. Czeczulin, J. R., Balepur, S., Hicks, S., Phillips, A., Hall, R., Kothary, M. H., et al. (1997) Aggregative adherence fimbria II, a second fimbrial antigen mediating aggregative adherence in enteroaggregative *Escherichia coli*. Infect Immun 65: 4135-4145.
4. de Onis, M., M. Blossner, E. Borghi, R. Morris, and E. A. Frongillo. 2004. Methodology for estimating regional and global trends of child malnutrition. Int. J. Epidemiol. 33:1260-70.
5. Dodd, D. C., and B. I. Eisenstein. 1982. Antigenic quantitation of Type I fimbriae on the surface of *Escherichia coli* cells by an enzyme-linked immunosorbent inhibition assay. Infect. Immun. 38:764-773.
6. DuPont, H. L., C. D. Ericsson, P. C. Johnson, and F. E. de la Cablda. 1990. Use of bismuth subsalicylate for the prevention of travellers' diarrhea. Rev. Infect. Dis. 12(suppl. 1):564-567.
7. Elias, W. P. Jr, J. R. Czeczulin, I. R. Henderson, L. R. Trabulsi, and J. P. Nataro. 1999. Organization of biogenesis genes for aggregative adherence fimbria II defines a virulence gene cluster in enteroaggregative *Escherichia coli*. J. Bacteriol. 181:1779-85.
8. Fox, L. M., and L. D. Saravolatz. 2005. Nitazoxanide: A New Thiazolide Antiparasitic Agent. Clin. Infect. Dis. 40:1173-80.
9. Glandt, M., J. A. Adachi, J. J. Mathewson, Z. D. Jiang, D. DiCesare, D. Ashley, C. D. Ericsson, and H. L. DuPont. 1999. Enteroaggregative *Escherichia coli* as a cause of traveler's diarrhea: clinical response to ciprofloxacin. Clin. Infect. Dis. 29:335-8.
10. Guerrant, R. L., et al. 2001. Practice guidelines for the management of infectious diarrhea. Clin. Infect. Dis. 32:331-51.
11. Guerrant, R. L., M. Kosek, A. A. M. Lima, B. Lorntz, and H. L. Guyatt. 2002. Updating the DALYs for diarrhoeal disease. Trends Parasitol. 18:191-3.
12. Harrington, S. M., E. G. Dudley, and J. P. Nataro. 2006. Pathogenesis of enteroaggregative *Escherichia coli* infection. FEMS Microbiol. Lett. 254:12-18.
13. Hemphill, A., J. Mueller, and M. Esposito. 2006. Nitazoxanide, a broad-spectrum thiazolide anti-infective agent for the treatment of gastrointestinal infections. Expert Opin Pharmacother. 7:953-964.
14. Hoffman, P. S., C. A. Butler, and F. D. Quinn. 1989. Cloning and temperature-dependent expression in *Escherichia coli* of a *Legionella pneumophila* gene coding for a genus-common 60-kilodalton antigen. Infect. Immun. 57:1731-1739.
15. Hoffman, P. S., J. H. Seyer, and C. A. Butler. 1992. Molecular characterization of the 28 and 31 kilodalton subunits of the *Legionella pneumophila* porin. J. Bacteriol. 174:908 913.
16. Hoffman, P. S., G. Sisson, M. A. Croxen, K. Welch, W. D. Harman, N. Cremades, and M. G. Morash. 2007. Anti-parastic drug nitazoxanide inhibits the pyruvate oxidoreductases of *Helicobacter pylori*, selected anaerobic bacteria and parasites, and *Campylobacter jejuni*. Antimicrob. Agents Chemother. 51:868-876.
17. Huang, D. B., and H. L. DuPont. 2004. Enteroaggregative *Escherichia coli*: An emerging pathogen in children. Semin. Pediatr. Infect. Dis. 15:266-271.
18. Huang, D. V., A. Mohanty, H. L. DuPont, P. C. Okhuysen, and T. Chiang. 2006. A review of an emerging enteric pathogen: enteroaggregative *Escherichia coli*. J. Med. Microbiol. 55:1303-11.
19. Infante, R. M., C. D. Ericsson, Z. D. Jiang, S. Ke, R. Steffen, L. Riopel, D. A. Sack, and H. L. DuPont. 2004. Enteroaggregative *Escherichia coli* diarrhea in travelers: response to rifaximin therapy. Clin. Gastroenterol. Hepatol. 2:135-8.
20. Jacob-Dubuisson, F., J. Pinkner, Z. Xu, R. Striker, A. Padmanhaban, and S. J. Hultgren. 1994. PapD chaperone function in pilus biogenesis depends on oxidant and chaperone-like activities of DsbA. Proc Natl Acad Sci USA. 91:11552-11556.
21. Kosek, M., C. Bern, and R. L. Guerrant. 2003. The global burden of diarrhoeal disease, as estimated from studies published between 1992 and 2000. Bull. World Health Organ. 81:197-204.
22. Louis, P., K. P. Scott, S. H. Duncan, and H. J. Flint. 2007. Understanding the effects of diet on bacterial metabolism in the large intestine. J Appl Microbiol. 102:1197-1208.
23. Manoil, C., and J. Beckwith. 1985. TnphoA: a transposon probe for protein export signals. Proc. Natl. Acad. Sci. USA 82:8129-8133.
24. Miller, J. H. 1972. Experiments in molecular genetics. Cold Spring Harbor Laboratory, Cold spring Harbor, N.Y.
25. Mohamed, J. A., D. B. Huang, Z. Jiang, H. L. DuPont, J. P. Nataro, J. Belkind-Gerson, and P. C. Okhuysen. 2007. Association of putative enteroaggregative *Escherichia coli* virulence genes and biofilm production in isolates from travelers to developing countries. J. Clin. Microbiol. 45:121-126.

26. Moreira, C. G., S. M. Carneiro, J. P. Nataro, L. R. Trabulsi, and W. P. Elias. 2003. Role of type I fimbriae in the aggregative adhesion pattern of enteroaggregative *Escherichia coli*. FEMS Microbiol. Lett. 226:79-85.
27. Musher, D. M., N. Logan, A. M. Bressler, D. P. Johnson, J. F. Rossignol. 2009. Nitazoxanide versus vancomycin in *Clostridium difficile* infection: A randomized, double-blind study. Clin Infect Dis. 48:41-46.
28. Nataro, J. P. 2005. Enteroaggregative *Escherichia coli* pathogenesis. Curr. Opin. Gastroenterol. 21:4-8.
29. Nataro, J. P., J. B. Kaper, R. Robins-Browne, V. Prado, P. Vial, and M. M. Levine. 1987. Patterns of adherence of diarrheagenic *Escherichia coli* to HEp-2 cells. Pediatr. Infect. Dis. J. 6:829-831.
30. Nataro, J. P., D. Yikang, D. Yingkang, and K. Walker. 1994. AggR, a transcriptional activator of aggregative adherence fimbria I expression in enteroaggregative *Escherichia coli*. J. Bacteriol. 176:4691-4699.
31. Pinkner, J. S., H. Remaut, F. Buelens, E. Miller, V. Aberg, N. Pemberton, M. Hedenström, A. Larsson, P. Seed, G. Waksman, S. J. Hultgren, and F. Almqvist. 2006. Rationally designed small compounds inhibit pilus biogenesis in uropathogenic bacteria. Proc Natl Acad Sci USA. 103: 17897-17902.
32. Pupo, G. M., D. K. R. Karadis, R. Lan, and P. R. Reeves. 1997. Evolutionary relationships among pathogenic and non-pathogenic *Escherichia coli* strains inferred from multilocus enzyme electrophoresis and mdh sequence studies. Infect. Immun. 64:2685-2692.
33. Remaut, H., C. Tang, N. S. Henderson, J. S. Pinkner, T. Wang, S. J. Hultgren, D. G. Thanassi, G. Waksman, and H. Li. 2009. Fiber formation across the bacterial outer membrane by the chaperone/usher pathway. Cell. 133:640-652.
34. Ricci, K. A., F. Girosi, P. I. Tarr, Y. Lim, C. Mason, M. Miller, J. Hughes, L. Seidlein, J. M. Agosti, and R. L. Guerrant. 2006. Reducing stunting among children: the potential contribution of diagnostics. Nature 444:29-38.
35. Ruiz-Perez F., J. Sheikh, S. Davis, E. C. Boedeker, and J. P. Nataro. 2004. Use of a continuous-flow anaerobic culture to characterize enteric virulence gene expression. Infect. Immun. 72:3793-3802.
36. Sarantuya, J., J. Nishi, N. Wakimoto, S. Erdene, J. P. Nataro, J. Sheikh, M. Iwashita, K. Manago, K. Tokuda, M. Yoshinaga, K. Miyata, and Y. Kawano. 2004. Typical enteroaggregative *Escherichia coli* is the most prevalent pathotype among *E. coli* strains causing diarrhea in Mongolian children. J. Clin. Microbiol. 42:133-139.
37. Sheikh, J., S. Hicks, M. Dall'Agnol, A. D. Phillips, and J. P. Nataro. 2001. Roles for Fis and YafK in biofilm formation by enteroaggregative *Escherichia coli*. Mol. Microbiol. 41:983-997.
38. Sisson, G., A. Goodwin, A. Raudonikiene, N. J. Hughes, A. K. Mukhopadhyay, D. E. Berg, and P. S. Hoffman. 2002. Enzymes associated with reductive activation and action of nitazoxanide, nitrofurans, and metronidazole in *Helicobacter pylori*. Antimicrob. Agents Chemother. 46:2116-2123.
39. Steiner, T. S., A. A. Lima, J. P. Nataro, and R. L. Guerrant. 1998. Enteroaggregative *Escherichia coli* produce intestinal inflammation and growth impairment and cause interleukin-8 release from intestinal epithelial cells. J. Infect. Dis. 177:88-96.
40. Velarde J J, Varney K M, Inman K G, Farfan M, Dudley E, Fletcher J, Weber D J, Nataro J P. 2007. Solution structure of the novel dispersin protein of enteroaggregative *Escherichia coli*. Mol Microbiol. 2007 December; 66(5):1123-35.
41. Wakimoto, N., J. Nishi, J. Sheikh, J. P. Nataro, J. Sarantuya, M. Iwashita, K. Manago, K. Tokuda, M. Yoshinaga, and Y. Kawano. 2004. Quantitative biofilm assay using a microtiter plate to screen for enteroaggregative *Escherichia coli*. Am. J. Trop. Med. Hyg. 71:687-690.
42. Zhang, H.-Z., and M. S. Donnenberg. 1996. DsbA is required for stability of the type IV pilin of enteropathogenic *Escherichia coli*. Mol. Microbiol. 21:787-797.
43. Zulu, I, P. Kelly, L. Njobvu, S. Sianongo, K. Kaonga, V. McDonald, M. Farthing, and R. Pollok. 2005. Nitazoxanide for persistent diarrhoea in Zambian acquired immune deficiency syndrome patients: a randomized-controlled trial. Aliment Pharmacol Ther. 21:757-763.

Example 3

New Compounds and their Activity

Additional work was performed to determine the effect of Nitazoxanide, and analogs and derivatives thereof, on various microbes. To that end, a series of general formulas has been devised and a series of compounds has been synthesized for each general formula and tested in several types of assays with multiple microorganisms. Data and tables below provide structures as well as biologic activity. Structural formulas are provided in the Summary of the Invention (above) and parent compounds and derivatives and analogs are provided below in the Tables.

General Experimental Procedures and Preparation of Compounds:

General Considerations:

All reagents were purchased from commercially available sources and used as is without further purification. All reactions were run under a nitrogen or argon atmosphere unless otherwise noted. Flash silica gel chromatography was performed with 60 Å mesh standard grade silica gel (Sortech). $^1$H and $^{13}$C NMR spectra were obtained using Varian 300 MHz or 500 MHz spectrometers and recorded at 23° C. Chemical shifts (s=singlet, bs=broad singlet, d=doublet, dd=doublet of doublets, dt=doublet of triplets, t=triplet, tt=triplet of triplets, m=multiplet) are given in parts per million relative to DMSO-$d_6$ (δ 2.50) for proton spectra and relative to DMSO-$d_6$ (δ 39.51) for carbon spectra. Mass spectra were obtained at the NCSU Department of Chemistry Mass Spectrometry Facility which is funded by the North Carolina Biotechnology Center and the NCSU Department of Chemistry.

Method A: Acid Chloride Amide Coupling:

Acid chloride (100 mg, 0.1 mL, 1 eq) was dissolved in THF (0.1M) and cooled to −78° C. then amino-heterocycle (1 eq) was added in one portion. DIPEA (1.1 eq) was added to the resulting slurry at −78° C. and the solution was held at this temperature for 10 mins then allowed to warm to room temperature overnight. The solution was judged complete by TLC analysis (~24 h) and was diluted with EtOAc (30 mL) and washed with sat. NaHCO$_3$ (3×20 mL), 1M HCl (3×20 mL) and brine (2×20 mL) then dried (MgSO$_4$) followed by filtration and evaporation to dryness. The resulting residue was purified by gradient flash column chromatography (10-60% EtOAc/hexanes or 1-2% MeOH/CH$_2$Cl$_2$) to obtain the product.

Method B: Carboxylic Acid EDC Amide Coupling:

Carboxylic acid (100 mg, 1 eq), EDC (2 eq), HOBT (2 eq) and DIPEA (3 eq) were dissolved in THF (0.1M) and stirred for 15 mins. Amino-heterocycle (1 eq) was then added in one portion and the reaction was stirred at ambient temperature. Once judged complete by TLC analysis (~24 h), the resulting suspension was diluted with EtOAc (30 mL) and washed with sat. NaHCO$_3$ (3×20 mL), 1M HCl (3×20 mL) and brine (2×20 mL) then dried (MgSO$_4$) followed by filtration and evaporation to dryness. The resulting residue was purified by gradient flash column chromatography (10-60% EtOAc/hexanes) to obtain the product.

Method C: Aromatic Alcohol Alkylation:

Aromatic alcohol (2.0 mL, 1 eq) was dissolved in DMF (0.3M) then finely ground K$_2$CO$_3$ (2 eq) and Boc-aminoethylbromide (1.5 eq) were added. The solution was warmed to 65° C. and stirred for 3 days then concentrated to near dryness. Water was then added and the resulting slurry was extracted with EtOAc (3×40 mL) The organic layers were combined and washed with H$_2$O (2×20 mL), 5% LiCl (2×20 mL) and brine (2×20 mL) then dried (MgSO$_4$) followed by filtration and evaporation to dryness to obtain the product.

Method D: Alkyl Ester Saponification:

Ester (240 mg, 1 eq) was dissolved in a mixture of MeOH: THF:H$_2$O (1M: 1M: 1M) then LiOH.H$_2$O (3 eq) was added. The solution was stirred for 24 hours then was quenched with 1M HCl (20 mL) and extracted with EtOAc (4×15 mL). The combined organic layers were then washed with brine (2×20 mL) then dried (MgSO$_4$) followed by filtration and evaporation to dryness to obtain the product.

Method E: Boc-Group Deprotection and HCl Salt Exchange:

Boc-Amine (1 eq) was suspended in anhydrous CH$_2$Cl$_2$ (0.02M) and cooled to 0° C. TFA (0.2M) was charged into the flask and the reaction stirred overnight. After that time the reaction was evaporated to dryness and hexanes was added. Again the mixture was concentrated and the process repeated. The resulting TFA salt was dissolved in CH$_2$Cl$_2$ and 2M HCl in Et$_2$O (0.15M) was added followed by cold Et$_2$O. The precipitate was collected by filtration and washed with Et$_2$O to obtain the title compound.

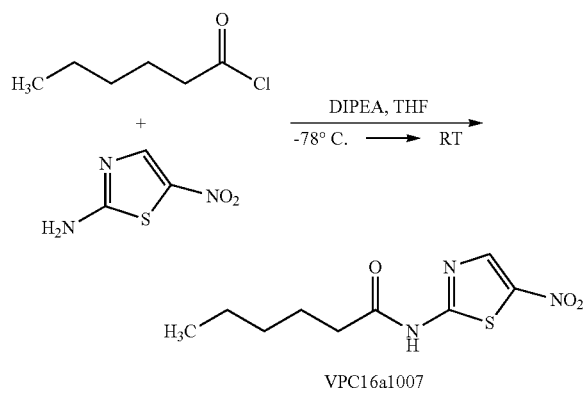

N-(5-Nitrothiazol-2-yl)hexanamide (VPC16a1007)

Method A yielded the title compound VPC16a1007 (126 mg, 71%) as a light orange solid. $^1$H NMR (500 MHz, DMSO-d$_6$) δ 13.02 (s, 1H), 8.57 (s, 1H), 2.50 (t, J=7.5 Hz, 2H), 1.67-1.44 (m, 2H), 1.44-1.07 (m, 4H), 0.85 (t, J=7.0 Hz, 3H); $^{13}$C NMR (125 MHz, DMSO-d$_6$) δ 173.1, 161.7, 142.6, 141.6, 34.9, 30.7, 24.0, 21.8, 13.8; HRMS (ESI) calcd for [C$_9$H$_{13}$N$_3$O$_3$S+H]$^+$ 244.0750. found 244.0757.

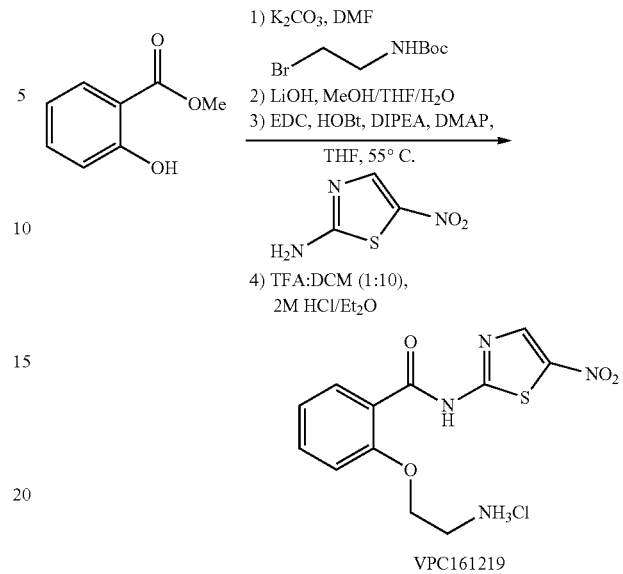

2-(2-Aminoethoxy)-N-(5-nitrothiazol-2-yl)benzamide hydrochloride (VPC161219)

Method C with methyl 2-hydroxybenzoate (2.0 mL, 15.4 mmol) afforded methyl 2-(2-(tert-butoxycarbonylamino) ethoxy)benzoate (4.55 g, 99%) as an amber oil. $^1$H NMR (300 MHz, DMSO-d$_6$) δ 7.64 (dd, J=7.6, 1.1 Hz, 1H), 7.57-7.45 (m, 1H), 7.14 (d, J=8.4 Hz, 1H), 7.02 (t, J=7.5 Hz, 1H), 6.83 (t, J=5.3 Hz, 1H), 4.03 (t, J=5.9 Hz, 2H), 3.79 (s, 3H), 3.31 (q, J=5.8 Hz, 2H), 1.38 (s, 9H); $^{13}$C NMR (75 MHz, DMSO-d$_6$) δ 157.4, 155.6, 133.4, 130.7, 120.6, 120.5, 114.0, 77.8, 67.4, 51.8, 39.3, 31.4, 28.2, 27.6; HRMS (ESI) calcd for [C$_{15}$H$_{21}$NO$_5$+Na]$^+$ 318.1312. found 318.1319. Method D with ethyl 2-(2-(tert-butoxycarbonylamino)ethoxy)benzoate (240 mg, 0.81 mmol) afforded 2-(2-(tert-butoxycarbonylamino)ethoxy)benzoic acid (221 mg, 97%) as a white solid. $^1$H NMR (300 MHz, DMSO-d$_6$) δ 12.56 (s, 1H), 7.65 (dd, J=7.6, 1.7 Hz, 1H), 7.48 (td, J=8.3, 1.7 Hz, 1H), 7.13 (d, J=8.4 Hz, 1H), 7.01 (t, J=7.5 Hz, 1H), 6.85 (t, J=5.3 Hz, 1H), 1.37 (s, 9H); $^{13}$C NMR (75 MHz, DMSO-d$_6$) δ 167.3, 157.3, 155.7, 133.1, 130.8, 121.7, 120.6, 114.1, 77.9, 67.6, 39.2, 28.2; HRMS (ESI) calcd for [C$_{14}$H$_{19}$NO$_5$+Na]$^+$ 304.115. found 304.1168. Method B with 2-(2-(tert-butoxycarbonylamino)ethoxy)benzoic acid (100 mg, 0.36 mmol) and cat. DMAP afforded tert-butyl 2-(2-(5-nitrothiazol-2-ylcarbamoyl)phenoxy)ethylcarbamate (56 mg, 38%) as a beige solid. $^1$H NMR (300 MHz, DMSO-d$_6$) δ 12.75 (s, 1H), 8.69 (s, 1H), 7.71 (dd, J=7.6, 1.7 Hz, 1H), 7.66-7.53 (m, 1H), 7.24 (d, J=8.4 Hz, 1H), 7.08 (dt, J=10.9, 6.4 Hz, 2H), 4.15 (t, J=5.7 Hz, 2H), 3.37 (q, J=5.6 Hz, 2H), 1.34 (s, 9H); $^{13}$C NMR (75 MHz, DMSO-d$_6$) δ 165.7, 161.6, 156.5, 155.7, 142.8, 141.9, 134.2, 130.6, 121.0, 120.9, 113.2, 77.9, 67.6, 39.2, 28.2; HRMS (ESI) calcd for [C$_{17}$H$_{20}$N$_4$O$_6$S+H]$^1$ 409.1176. found 409.1189. Method E with tert-butyl 2-(2-(5-nitrothiazol-2-ylcarbamoyl)phenoxy)ethylcarbamate (32 mg, 0.07 mmol) afforded the title compound VPC161219 (27 mg, 99%) as a tan solid. $^1$H NMR (300 MHz, DMSO-d$_6$) δ 12.94 (s, 1H), 8.71 (s, 1H), 8.24 (s, 3H), 7.69 (dd, J=7.6, 1.4 Hz, 1H), 7.66-7.57 (m, 1H), 7.25 (d, J=8.4 Hz, 1H), 7.15 (t, J=7.5 Hz, 1H), 4.35 (t, J=4.8 Hz, 3H), 3.24 (q, J=4.3 Hz, 2H); $^{13}$C NMR (75 MHz, DMSO-d$_6$) δ 165.8, 161.8, 155.7, 142.8, 141.9, 134.1, 130.8, 121.6, 121.3, 113.2, 65.2, 38.2; HRMS (ESI) calcd for [C$_{12}$H$_{12}$N$_4$O$_4$S+H]$^+$ 309.0652. found 309.0666.

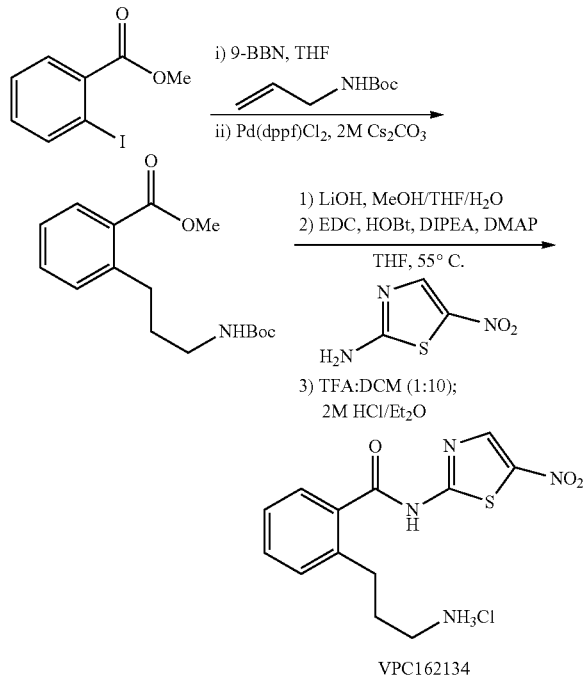

2-(3-Aminopropyl)-N-(5-nitrothiazol-2-yl)benzamide hydrochloride (VPC162134)

tert-Butyl allylcarbamate (113 mg, 0.72 mmol) and THF (1.5 mL) were charged into a flame-dried round bottom flask followed by the dropwise addition of 0.5M 9-BBN in THF (1.92 mL). After 2 h, 2M Cs$_2$CO$_3$ (0.72 mL), methyl 2-iodobenzoate (0.07 mL, 0.48 mmol) and Pd(dppf)Cl$_2$ (27.7 mg, 5 mol %) were added to the flask and held at room temperature. Once judged complete my TLC (~24 h), the crude mixture was diluted with EtOAc (30 mL) and washed with sat. NH$_4$Cl (2×20 mL) and brine (2×20 mL) then dried (MgSO$_4$) followed by filtration and evaporation to dryness. The resulting residue was purified by gradient flash column chromatography (5-30% EtOAc/hexanes) to obtain methyl 2-(3-(tert-butoxycarbonylamino)propyl)benzoate (130 mg, 93%) as an amber oil. $^1$H NMR (500 MHz, DMSO-d$_6$) δ 7.76 (dd, J=7.8, 1.1 Hz, 1H), 7.49 (td, J=7.5, 1.4 Hz, 1H), 7.34-7.28 (m, 2H), 6.85 (t, J=5.4 Hz, 1H), 3.82 (s, 3H), 2.93 (q, J=6.7 Hz, 2H), 2.86-2.79 (m, 2H), 1.65-1.58 (m, 2H), 1.37 (s, 9H); $^{13}$C NMR (125 MHz, DMSO-d$_6$) δ 167.5, 155.57, 143.0, 132.0, 130.9, 130.1, 129.4, 126.1, 77.4, 52.0, 39.8, 31.6, 31.0, 28.3; HRMS (ESI) calcd for [C$_{16}$H$_{23}$NO$_4$+Na]$^+$ 316.1519. found 316.1152. Method D with methyl 2-(3-(tert-butoxycarbonylamino)propyl)benzoate (130 mg, 0.45 mmol) afforded 2-(3-(tert-butoxycarbonylamino)propyl)benzoic acid (120 mg, 96%) as a white solid. $^1$H NMR (500 MHz, DMSO-d$_6$) δ 12.82 (bs, 1H), 7.77 (dd, J=7.7, 1.1 Hz, 1H), 7.45 (td, J=7.5, 1.3 Hz, 1H), 7.33-7.24 (m, 2H), 6.81 (t, J=5.3 Hz, 1H), 3.00-2.83 (m, 4H), 1.78-1.53 (m, 2H), 1.37 (s, 9H); $^{13}$C NMR (125 MHz, DMSO-d$_6$) δ 168.8, 155.6, 142.9, 131.6, 130.8, 130.5, 130.2, 125.9, 77.4, 31.5, 30.9, 28.3; HRMS (ESI) calcd for [C$_{15}$H$_{21}$NO$_4$+Na]$^+$ 302.1363. found 302.1359. Method B with 2-(3-(tert-butoxycarbonylamino)propyl)benzoic acid (95 mg, 0.34 mmol) and cat. DMAP at 55° C. afforded tert-butyl 3-(2-(5-nitrothiazol-2-ylcarbamoyl)phenyl)propylcarbamate (58 mg, 42%) as a light yellow solid. $^1$H NMR (500 MHz, DMSO-d$_6$) δ 13.54 (bs, 1H), 8.69 (s, 1H), 7.60 (d, J=7.6 Hz, 1H), 7.51 (t, J=7.6 Hz, 1H), 7.43-7.32 (m, 2H), 6.81 (t, J=5.5 Hz, 1H), 2.91 (q, J=6.5 Hz, 2H), 2.79-2.67 (m, 2H), 1.74-1.40 (m, 2H), 1.34 (s, 9H); $^{13}$C NMR (125 MHz, DMSO-d$_6$) δ 168.7, 162.0, 155.5, 142.6, 142.0, 141.2, 132.3, 131.5, 130.2, 128.5, 125.9, 77.3, 39.6, 31.5, 30.0, 28.2; HRMS (ESI) calcd for [C$_{18}$H$_{22}$N$_4$O$_5$S+Na]$^+$ 429.1203. found 429.1201. Method E with tert-butyl 3-(2-(5-nitrothiazol-2-ylcarbamoyl)phenyl)propylcarbamate (310 mg, 0.76 mmol) afforded the title compound VPC162134 (257 mg, 98%) as a beige solid. $^1$H NMR (500 MHz, DMSO-d$_6$) δ 13.60 (s, 1H), 8.71 (s, 1H), 8.05 (bs, 3H), 7.65 (d, J=7.7 Hz, 1H), 7.55 (t, J=7.6 Hz, 1H), 7.47-7.35 (m, 2H), 2.81 (t, J=7.5 Hz, 2H), 2.79-2.71 (m, 2H), 1.87 (quint., J=7.5 Hz, 2H); $^{13}$C NMR (125 MHz, DMSO-d$_6$) δ 168.6, 162.1, 142.7, 142.0, 140.3, 132.2, 131.7, 130.2, 128.8, 126.3, 38.4, 29.6, 28.9; HRMS (ESI) calcd for [C$_{13}$H$_{14}$N$_4$O$_3$S+H]$^+$ 307.0859. found 307.0855.

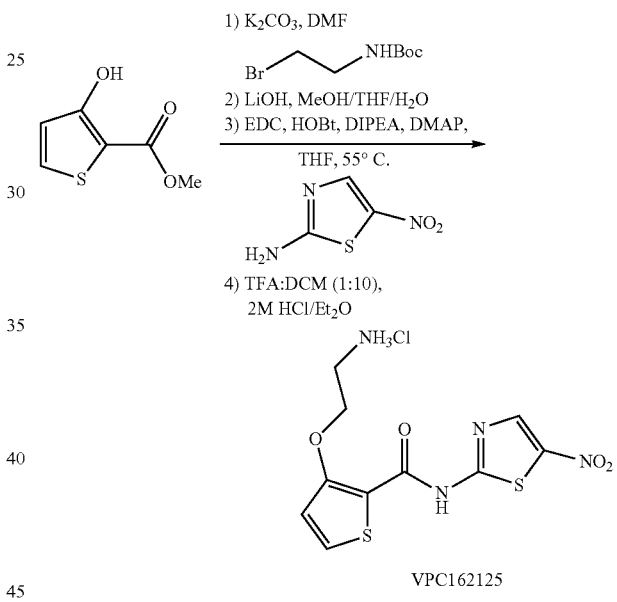

3-(2-Aminoethoxy)-N-(5-nitrothiazol-2-yl)thiophene-2-carboxamide hydrochloride (VPC162125)

Method C with methyl 3-hydroxythiophene-2-carboxylate (1.0 g 6.32 mmol) afforded methyl 3-(2-(tert-butoxycarbonylamino)ethoxy)thiophene-2-carboxylate (1.9 g, 100%) as an amber oil. $^1$H NMR (500 MHz, DMSO-d$_6$) δ 7.81 (d, J=5.5 Hz, 1H), 7.11 (d, J=5.5 Hz, 1H), 6.91 (t, J=5.5 Hz, 1H), 4.12 (t, J=6.0 Hz, 2H), 3.72 (s, 3H), 3.27 (q, J=5.9 Hz, 2H), 1.37 (s, 9H); $^{13}$C NMR (125 MHz, DMSO-d$_6$) δ 161.3, 160.9, 155.6, 132.0, 118.2, 108.7, 77.9, 70.0, 51.4, 39.4, 28.2; HRMS (ESI) calcd for [C$_{13}$H$_{19}$NO$_5$S+Na]$^+$ 324.0876. found 324.0877. Method D with methyl 3-(2-(tert-butoxycarbonylamino)ethoxy)thiophene-2-carboxylate (70 mg, 0.23 mmol) afforded 3-(2-(tert-butoxycarbonylamino)ethoxy)thiophene-2-carboxylic acid (63 mg, 95%) as a white solid. $^1$H NMR (500 MHz, DMSO-d$_6$) δ 12.43 (bs, 1H), 7.74 (d, J=5.5 Hz, 1H), 7.08 (d, J=5.5 Hz, 1H), 6.91 (t, J=5.5 Hz, 1H), 4.10 (t, J=6.1 Hz, 2H), 3.25 (q, J=6.0 Hz, 2H), 1.37 (s, J=12.2 Hz, 9H); $^{13}$C NMR (125 MHz, DMSO-$d_6$) δ 162.4, 160.3, 155.7, 131.3, 118.4, 110.5, 77.9, 70.0, 39.5, 28.2; HRMS (ESI) calcd for $[C_{12}H_{17}NO_5S+Na]^+$ 310.0720. found 310.0719. Method B with 3-(2-(tert-butoxycarbonylamino)ethoxy)thiophene-2-carboxylic acid (100 mg, 0.35 mmol) and cat. DMAP at 55° C. afforded tert-butyl 2-(2-(5-nitrothiazol-2-ylcarbamoyl)thiophen-3-yloxy)ethylcarbamate (100 mg, 69%) as a beige solid. $^1$H NMR (500 MHz, DMSO-$d_6$) δ 11.30 (bs, 1H), 8.67 (s, 1H), 8.06 (d, J=5.5 Hz, 1H), 7.29-7.22 (m, 2H), 4.34 (t, J=5.1 Hz, 2H), 3.39 (q, J=5.2 Hz, 2H), 1.33 (s, 9H); $^{13}$C NMR (125 MHz, DMSO-$d_6$) δ 160.9, 159.4, 159.1, 155.8, 142.5, 142.2, 134.9, 117.7, 78.0, 71.9, 39.4, 28.1; HRMS (ESI) calcd for $[C_{15}H_{18}N_4O_6S_2+H]^+$ 415.0741. found 415.0745. Method E with tert-butyl 2-(2-(5-nitrothiazol-2-ylcarbamoyl)thiophen-3-yloxy)ethylcarbamate (25 mg, 0.06 mmol) afforded the title compound VPC162125 (21 mg, 100%) as a light yellow solid. $^1$H NMR (500 MHz, DMSO-$d_6$) δ 11.62 (bs, 1H), 8.70 (bs, 1H), 8.51 (bs, 3H), 8.07 (bs, 1H), 7.27 (bs, 1H), 4.52 (bs, 2H), 3.26 (bs, 2H); $^{13}$C NMR (125 MHz, DMSO-$d_6$) δ 160.9, 159.3, 157.8, 142.4, 141.9, 134.8, 117.5, 111.8, 68.7, 38.2; HRMS (ESI) calcd for $[C_{10}H_{10}N_4O_4S_2+H]^+$ 315.0216. found 315.0217.

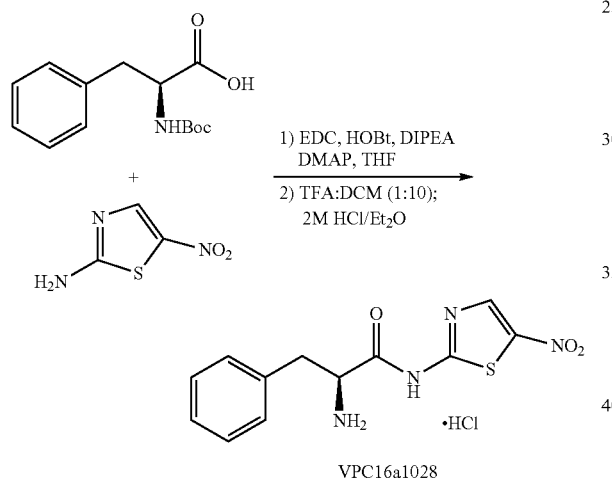

S)-2-Amino-N-(5-nitrothiazol-2-yl)-3-phenylpropanamide hydrochloride (VPC16a1028)

Method B with Boc-L-phenylalanine (100 mg, 0.38 mmol) afforded (S)-tert-butyl-1-(5-nitrothiazol-2-ylamino)-1-oxo-3-phenylpropan-2-ylcarbamate (107 mg, 72%) as a beige solid. $^1$H NMR (300 MHz, DMSO-$d_6$) δ 13.37 (s, 1H), 8.64 (s, 1H), 7.44 (d, J=7.5 Hz, 1H), 7.35-7.18 (m, 5H), 4.47 (bs, 1H), 3.03 (dd, J=13.6, 4.3 Hz, 1H), 2.92-2.75 (m, 1H), 1.31 (s, 9H); $^{13}$C NMR (75 MHz, DMSO-$d_6$) δ 173.0, 161.5, 155.5, 142.7, 142.0, 137.2, 129.3, 128.2, 126.6, 78.5, 56.2, 36.5, 28.1; HRMS (ESI) calcd for $[C_{17}H_{20}N_4O_5S+Na]^+$ 415.1047. found 415.1057. Method E with (5)-tert-butyl-1-(5-nitrothiazol-2-ylamino)-1-oxo-3-phenylpropan-2-ylcarbamate (30 mg, 0.08 mmol) afforded the title compound VPC16a1028 (25 mg, 99%) as a brown solid. $^1$H NMR (500 MHz, DMSO-$d_6$) δ 13.83 (bs, 1H), 8.71 (bs, 3H), 8.67 (s, 1H), 7.35-7.30 (m, 2H), 7.27 (t, J=8.5 Hz, 3H), 4.44 (t, J=6.4 Hz, 1H), 3.24 (dd, J=13.8, 6.4 Hz, 1H), 3.17 (dd, J=13.8, 7.5 Hz, 1H); $^{13}$C NMR (125 MHz, DMSO-$d_6$) δ 169.0, 160.6, 142.5, 134.1, 129.5, 128.7, 127.4, 53.8, 36.5; HRMS (ESI) calcd for $[C_{12}H_{12}N_4O_3S+H]^+$ 292.0703. found 292.0711.

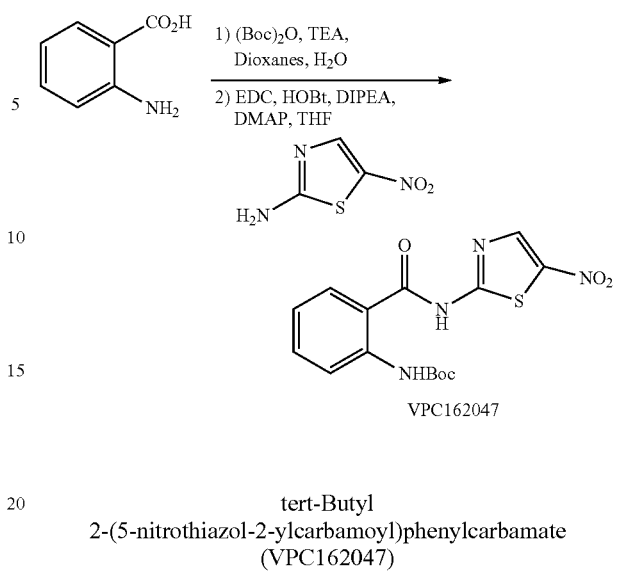

tert-Butyl 2-(5-nitrothiazol-2-ylcarbamoyl)phenylcarbamate (VPC162047)

Method B with 2-(tert-butoxycarbonylamino)benzoic acid[1] (100 mg, 0.42 mmol) and catalytic DMAP in DMF (in place of THF) afforded the title compound VPC162047 (108 mg, 71%) as a beige solid. $^1$H NMR (300 MHz, DMSO-$d_6$) δ 13.47 (bs, 1H), 9.65 (s, 1H), 8.69 (s, 1H), 7.77 (d, J=7.7 Hz, 1H), 7.70 (d, J=8.2 Hz, 1H), 7.55 (t, J=7.7 Hz, 1H), 7.19 (t, J=7.6 Hz, 1H), 1.39 (s, 9H); $^{13}$C NMR (75 MHz, DMSO-$d_6$) δ 167.9, 162.6, 152.7, 142.5, 141.7, 138.2, 132.9, 129.4, 122.7, 122.4, 121.4, 79.8, 27.9; HRMS (ESI) calcd for $[C_{15}H_{16}N_4O_5S+H]^+$ 387.0734. found 387.0745.

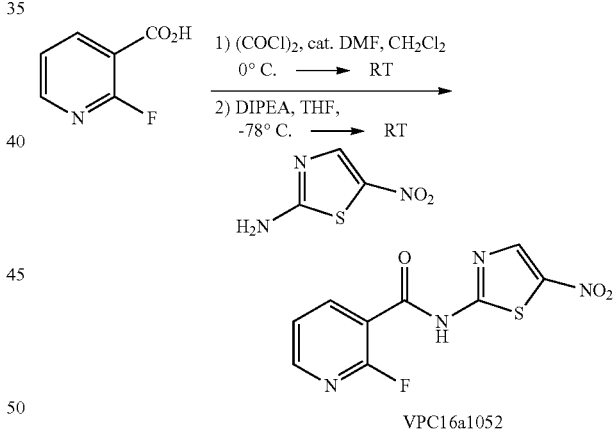

2-Fluoro-N-(5-nitrothiazol-2-yl)nicotinamide (VPC16a1052)

2-Fluoronicotinic acid (100 mg, 0.71 mmol) was dissolved in $CH_2Cl_2$ (2 mL) with a drop of DMF (catalytic) and cooled to 0° C. then $(COCl)_2$ (0.18 mL, 2.12 mmol) was added dropwise to the stirring solution. The slurry was allowed to warm to room temperature for 2 hours then concentrated to dryness using hexanes to remove the excess $(COCl)_2$. The resulting acid chloride was dissolved in THF (7 mL) and DIPEA (0.26 mL, 1.49 mmol) was added. The solution was cooled to −78° C. and 2-amino-5-nitrothiazole (108 mg, 0.78 mmol) was then added in one portion and the solution was held at −78° C. for 10 mins then warmed to room temperature and stirred for 2 days until judged complete by TLC analysis. The resulting suspension was quenched with 2M HCl in Et$_2$O (0.78 mL, 1.56 mmol) and concentrated to dryness then purified by flash column chromatography (1% MeOH/CH$_2$Cl$_2$) to obtain the title compound VPC16a1052 (118 mg, 62%) as a yellow solid. $^1$H NMR (300 MHz, DMSO-d$_6$) δ 13.77 (bs, 1H), 8.70 (s, 1H), 8.54-8.44 (m, 1H), 8.41-8.35 (m, 1H), 7.63-7.50 (m, 1H); $^{13}$C NMR (75 MHz, DMSO-d$_6$) δ 163.0 (d, $J_{CF}$=5.9 Hz), 161.5, 159.4 (d, $J_{CF}$=242 Hz), 151.3 (d, $J_{CF}$=15.2 Hz), 142.4, 142.3, 122.3 (d, $J_{CF}$=4.1 Hz), 115.9 (d, $J_{CF}$=28.5 Hz); HRMS (ESI) calcd for [C$_9$H$_5$FN$_4$O$_3$S+H]$^+$ 269.0139. found 269.0143.

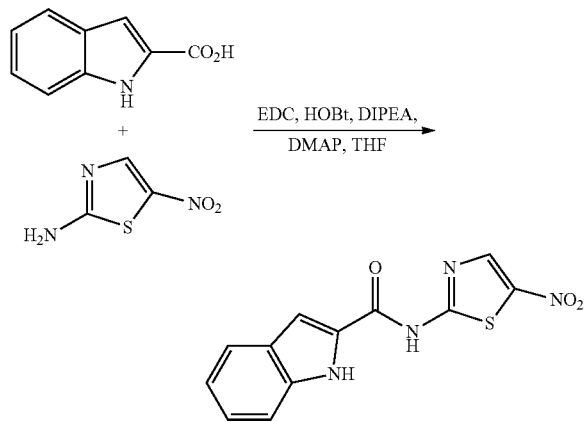

N-(5-Nitrothiazol-2-yl)-1H-indole-2-carboxamide (VPC16b1031)

Method B with 1H-indole-2-carboxylic acid (75 mg, 0.47 mmol) with cat. DMAP afforded the title compound VPC16b1031 (92 mg, 69%) as an orange solid. $^1$H NMR (500 MHz, DMSO-d$_6$) δ 13.65 (s, 1H), 12.10 (s, 1H), 8.69 (s, 1H), 7.76 (s, 1H), 7.70 (d, J=8.0 Hz, 1H), 7.48 (d, J=8.2 Hz, 1H), 7.29 (t, J=7.5 Hz, 1H), 7.10 (t, J=7.4 Hz, 1H); $^{13}$C NMR (125 MHz, DMSO-d$_6$) δ 162.4, 160.1, 142.8, 141.9, 137.9, 128.1, 126.8, 125.3, 122.5, 120.5, 112.6, 107.6; HRMS (ESI) calcd for [C$_{12}$H$_8$N$_4$O$_3$S+H]$^+$ 289.0390. found 289.0396.

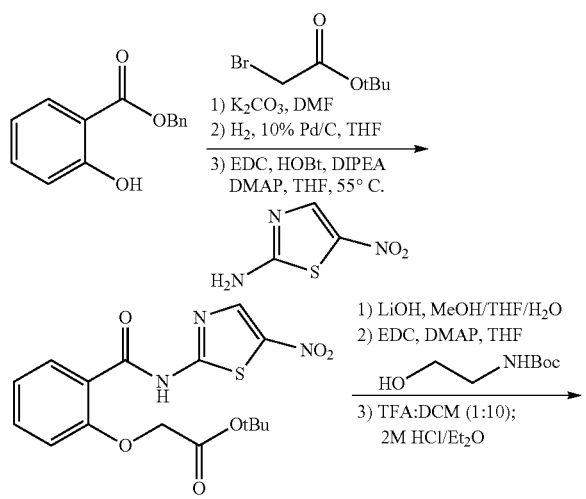

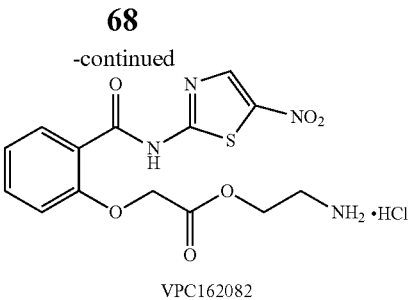

2-Aminoethyl 2-(2-(5-nitrothiazol-2-ylcarbamoyl)phenoxy)acetate hydrochloride (VPC162082)

Method C with benzyl 2-hydroxybenzoate (1.05 mL, 5.2 mmol) and tert-butyl 2-bromoacetate (in place of Boc-aminoethylbromide) afforded benzyl 2-(2-tert-butoxy-2-oxoethoxy)benzoate (1.82 g, 98%) as a amber oil. $^1$H NMR (300 MHz, DMSO-d$_6$) δ 7.69 (dd, J=7.6, 1.3 Hz, 1H), 7.65-7.42 (m, 3H), 7.42-7.19 (m, 3H), 7.13-6.97 (m, 2H), 5.31 (s, 2H), 4.76 (s, 2H), 1.40 (s, 9H); $^{13}$C NMR (75 MHz, DMSO-d$_6$) δ 167.4, 165.4, 156.7, 136.2, 133.3, 130.7, 128.4, 127.9, 127.7, 120.8, 120.5, 113.5, 81.5, 65.9, 65.5, 27.6; HRMS (ESI) calcd for [C$_{20}$H$_{22}$O$_5$+Na]$^+$ 365.1359. found 365.1367. To a solution of anhydrous THF (42 mL) and 10% Pd/C (0.15 g) was charged benzyl 2-(2-tert-butoxy-2-oxoethoxy)benzoate (1.56 g, 4.29 mmol). Air was removed from the system and the reaction was back flushed with hydrogen. This process was repeated three times before setting the reaction under a hydrogen balloon at atmospheric pressure and temperature for 22 h. After that time the reaction was filtered through a Celite® pad and the filter cake was washed with THF (20 mL). The filtrate was concentrated under reduced pressure to afford 2-(2-tert-butoxy-2-oxoethoxy)benzoic acid (1.14 g, 99%) as a tan amorphous solid. $^1$H NMR (300 MHz, DMSO-d$_6$) δ 12.61 (bs, 1H), 7.67 (dd, J=7.6, 1.5 Hz, 1H), 7.56-7.40 (m, 1H), 7.11-6.92 (m, 2H), 4.74 (s, 2H), 1.41 (s, 9H); $^{13}$C NMR (75 MHz, DMSO-d$_6$) δ 167.6, 167.1, 156.5, 132.8, 130.8, 121.6, 120.8, 113.5, 81.5, 65.6, 27.7; HRMS (ESI) calcd for [C$_{13}$H$_{16}$O$_5$+Na]$^+$ 275.0890. found 275.0898. Method B with 2-(2-tert-butoxy-2-oxoethoxy)benzoic acid (200 mg, 0.79 mmol) afforded tert-butyl 2-(2-(5-nitrothiazol-2-ylcarbamoyl)phenoxy)acetate (VPC162035) (178 mg, 59%) as a light yellow solid. $^1$H NMR (300 MHz, DMSO-d$_6$) δ 12.71 (s, 1H), 8.71 (s, 1H), 7.83 (dd, J=7.7, 1.5 Hz, 1H), 7.69-7.54 (m, 1H), 7.26-7.10 (m, 2H), 4.89 (s, 2H), 1.44 (s, 9H); $^{13}$C NMR (75 MHz, DMSO-d$_6$) δ 167.6, 165.0, 161.3, 155.7, 142.7, 142.1, 134.4, 130.8, 121.7, 120.4, 113.6, 82.1, 66.0, 27.7; HRMS (ESI) calcd for [C$_{16}$H$_{17}$N$_3$O$_6$S+H]$^+$ 380.0911. found 380.0936. Method D with tert-butyl 2-(2-(5-nitrothiazol-2-ylcarbamoyl)phenoxy)acetate (100 mg, 0.26 mmol) afforded 2-(2-(5-nitrothiazol-2-ylcarbamoyl)phenoxy)acetic acid (VPC162042) (78 mg, 92%) as a beige solid. $^1$H NMR (300 MHz, DMSO-d$_6$) δ 12.93 (bs, 2H), 8.67 (s, 1H), 7.87 (dd, J=7.7, 1.7 Hz, 1H), 7.72-7.57 (m, 1H), 7.24 (d, J=8.5 Hz, 1H), 7.18 (t, J=7.6 Hz, 1H), 4.94 (s, 2H); $^{13}$C NMR (75 MHz, DMSO-d$_6$) δ 170.5, 164.8, 161.4, 156.1, 142.8, 142.2, 134.7, 131.1, 121.9, 120.2, 114.2, 66.1; HRMS (ESI) calcd for [C$_{12}$H$_9$N$_3$O$_6$S+H]$^+$ 324.0285. found 324.0298. EDC (30 mg, 0.15 mmol), catalytic DMAP, Boc-ethanolamine (14 μL, 0.09 mmol) and 2-(2-(5-nitrothiazol-2-ylcarbamoyl)phenoxy)acetic acid (25 mg, 0.08 mmol) were dissolved in THF (1 mL) and stirred at ambient temperature for 21 hours. Once judged complete by TLC analysis, the resulting suspension was diluted with EtOAc (30 mL) and washed with sat. NaHCO$_3$ (3×20 mL), 0.5M HCl (3×20 mL) and brine (2×20 mL) then dried (MgSO$_4$) followed by filtration and evaporation to dryness. The resulting residue was purified by flash column chromatography (10-70% EtOAc/hexanes) to obtain 2-(tert-butoxycarbonylamino)ethyl 2-(2-(5-nitrothiazol-2-ylcarbamoyl)phenoxy)acetate (33 mg, 92%) as a beige solid. $^1$H NMR (300 MHz, DMSO-d$_6$) δ 12.69 (s, 1H), 8.71 (s, 1H), 7.87 (dd, J=7.7, 1.6 Hz, 1H), 7.69-7.57 (m, 1H), 7.25 (d, J=8.4 Hz, 1H), 7.19 (t, J=7.5 Hz, 1H), 6.97 (t, J=5.6 Hz, 1H), 4.98 (s, 2H), 4.19 (t, J=5.5 Hz, 2H), 3.21 (q, J=5.5 Hz, 2H), 1.35 (s, 9H); $^{13}$C NMR (75 MHz, DMSO-d$_6$) δ 168.4, 164.8, 161.3, 155.8, 142.79, 142.2, 134.6, 131.0, 121.8, 120.1, 113.8, 77.9, 65.9, 64.0, 38.8, 28.2; HRMS (ESI) calcd for [C$_{19}$H$_{22}$N$_4$O$_8$S+H]$^+$ 467.1231. found 467.1241. Method E with 2-(tert-butoxycarbonylamino)ethyl 2-(2-(5-nitrothiazol-2-ylcarbamoyl)phenoxy)acetate (24 mg, 0.05 mmol) afforded the title compound VPC162082 (19 mg, 93%) as a beige solid. $^1$H NMR (300 MHz, DMSO-d$_6$) δ 12.69 (s, 1H), 8.73 (s, 1H), 8.11 (s, 3H), 7.87 (dd, J=7.7, 1.5 Hz, 1H), 7.65 (t, J=7.0 Hz, 1H), 7.28 (d, J=8.4 Hz, 1H), 7.20 (t, J=7.5 Hz, 1H), 5.04 (s, 2H), 4.41 (t, J=5.1 Hz, 2H), 3.15 (s, 2H); $^{13}$C NMR (75 MHz, DMSO-d$_6$) δ 168.3, 164.8, 161.3, 155.7, 142.8, 142.1, 134.6, 131.0, 121.9, 120.1, 113.8, 65.9, 61.4, 37.9; HRMS (ESI) calcd for [C$_{14}$H$_{14}$N$_4$O$_6$S+Na]$^+$ 389.0526. found 389.0535.

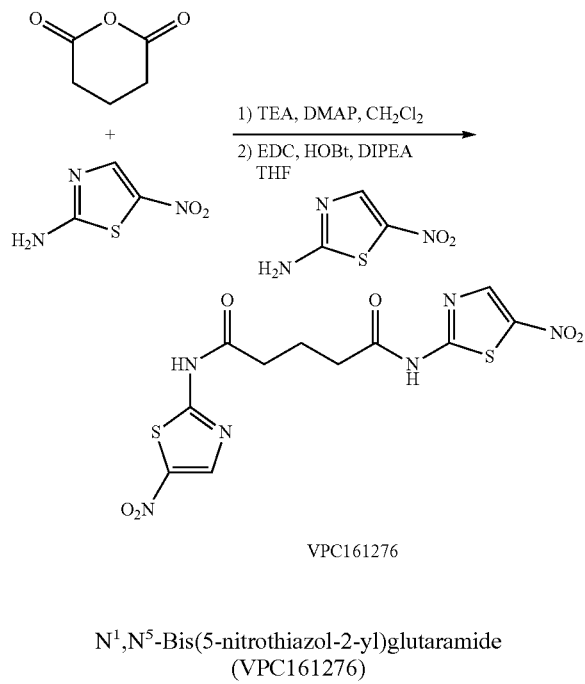

VPC161276

N$^1$,N$^5$-Bis(5-nitrothiazol-2-yl)glutaramide (VPC161276)

Glutaric anhydride (1.0 g, 8.8 mmol), TEA (1.35 ml, 9.6 mmol) and cat. DMAP were dissolved in CH$_2$Cl$_2$ (7 mL). 2-Amino-5-nitrothiazole (1.4 g, 9.64 mmol) was then added and the solution was held at ambient temperature. After 18 hours, the solution was diluted with EtOAc (50 mL) and extracted with 1M NaOH (3×30 mL). The combined aqueous layers were washed with EtOAc (20 mL) then acidified with 12M HCl and subsequently extracted with EtOAc (5×20 mL). The combined organics were washed with brine (2×20 mL), dried (MgSO$_4$), filtered and concentrated to dryness to yield 5-(5-nitrothiazol-2-ylamino)-5-oxopentanoic acid (1.13 g, 54%) as an orange solid. $^1$H NMR (300 MHz, DMSO-d$_6$) δ 12.59 (bs, 1H), 8.59 (s, 1H), 2.57 (t, J=7.4 Hz, 2H), 2.28 (t, J=7.3 Hz, 2H), 1.82 (quint., J=7.3 Hz, 2H); $^{13}$C NMR (75 MHz, DMSO-d$_6$) δ 174.0, 172.8, 161.8, 142.8, 141.7, 34.1, 32.7, 19.6; HRMS (ESI) calcd for [C$_8$H$_9$N$_3$O$_5$S+H]$^+$ 260.0336. found 260.0344. Method B with 5-(5-nitrothiazol-2-ylamino)-5-oxopentanoic acid (30 mg, 0.12 mmol) afforded the title compound VPC161276 (23 mg, 46%) as an orange solid. $^1$H NMR (300 MHz, DMSO-d$_6$) δ 8.61 (s, 2H), 2.61 (t, J=7.2 Hz, 4H), 1.97 (quint., J=7.0 Hz, 2H); $^{13}$C NMR (75 MHz, DMSO-d$_6$) δ 172.8, 162.0, 142.8, 141.5, 34.0, 19.3; HRMS (ESI) calcd for [C$_{11}$H$_{10}$N$_6$O$_6$S$_2$+H]$^+$ 387.0176. found 387.0185.

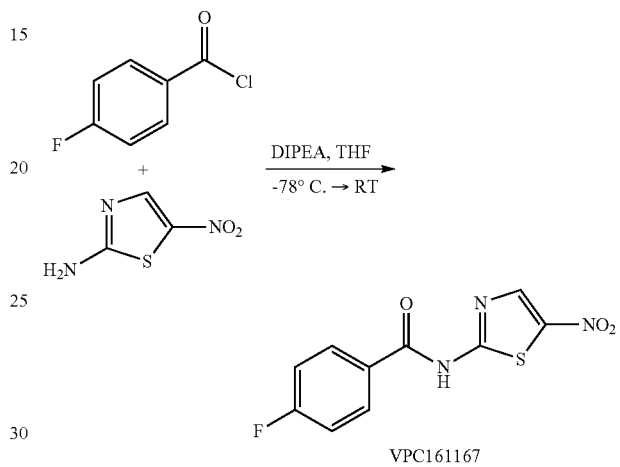

4-Fluoro-N-(5-nitrothiazol-2-yl)benzamide (VPC161167)

Method A with 4-fluorobenzoyl chloride (0.1 mL, 0.84 mmol) afforded the title compound VPC161167 (96 mg, 43%) as a tan solid. $^1$H NMR (300 MHz, DMSO-d$_6$) δ 13.62 (s, 1H), 8.72 (s, 1H), 8.22 (dd, J=8.8, 5.4 Hz, 2H), 7.43 (t, J=8.9 Hz, 2H); $^{13}$C NMR (125 MHz, DMSO-d$_6$) δ 165.3, 165.2 (d, J$_{CF}$=150 Hz), 162.6, 142.6, 142.1, 131.6 (d, J$_{CF}$=9.5 Hz), 127.4, 115.9 (d, J$_{CF}$=22.1 Hz); HRMS (ESI) calcd for [C$_{10}$H$_6$FN$_3$O$_3$S+H]$^+$ 268.0187. found 268.0196.

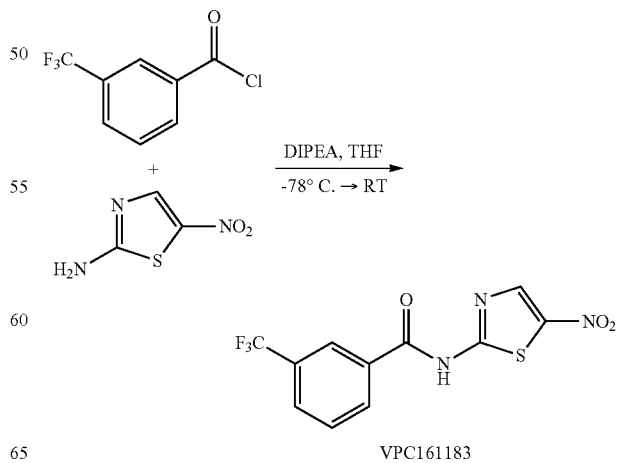

VPC161183

N-(5-Nitrothiazol-2-yl)-3-(trifluoromethyl)benzamide (VPC161183)

Method A with 3-(trifluoromethyl)benzoyl chloride (0.1 mL, 0.68 mmol) afforded the title compound VPC161183 (157 mg, 75%) as a light yellow solid. $^1$H NMR (300 MHz, DMSO-$d_6$) δ 13.85 (bs, 1H), 8.74 (s, 1H), 8.51 (s, 1H), 8.39 (d, J=8.2 Hz, 1H), 8.06 (d, J=7.9 Hz, 1H), 7.83 (t, J=7.9 Hz, 1H); $^{13}$C NMR (125 MHz, DMSO-$d_6$) δ 165.2, 162.4, 142.5, 142.2, 132.7, 131.9, 130.1, 129.8 (q, $J_{CF}$=3.4 Hz), 129.4 (q, $J_{CF}$=32.6 Hz), 125.2 (q, $J_{CF}$=3.9 Hz), 123.8 (q, $J_{CF}$=273 Hz); HRMS (ESI) calcd for $[C_{11}H_6F_3N_3O_3S+H]^+$ 318.0155. found 318.0164.

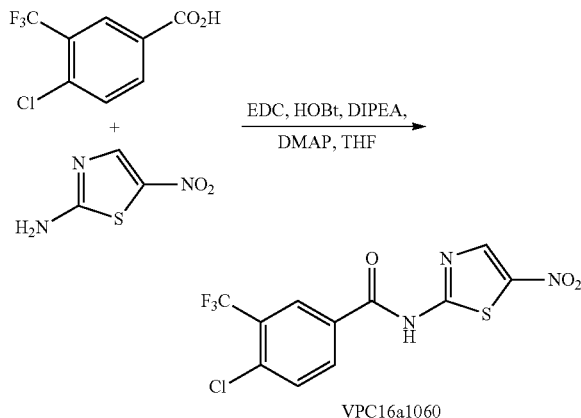

4-Chloro-N-(5-nitrothiazol-2-yl)-3-(trifluoromethyl)benzamide) (VPC16a1060)

Method B with 4-chloro-3-(trifluoromethyl)benzoic acid (100 mg, 0.45 mmol) afforded the title compound VPC16a1060 (126 mg, 80%) as an orange solid. $^1$H NMR (300 MHz, DMSO-$d_6$) δ 13.89 (bs, 1H), 8.71 (d, J=0.6 Hz, 1H), 8.58 (d, J=1.9 Hz, 1H), 8.35 (dd, J=8.4, 2.1 Hz, 1H), 7.94 (d, J=8.4 Hz, 1H); $^{13}$C NMR (75 MHz, DMSO-$d_6$) δ 164.4, 162.4, 142.3, 135.7, 134.2, 132.3, 130.4, 127.9 (d, $J_{CF}$=4.8 Hz), 126.9 (q, $J_{CF}$=31.6 Hz), 122.5 (q, $J_{CF}$=274 Hz); HRMS (ESI) calcd for $[C_{11}H_5C_1F_3N_3O_3S+H]^+$ 351.9765. found 351.9775.

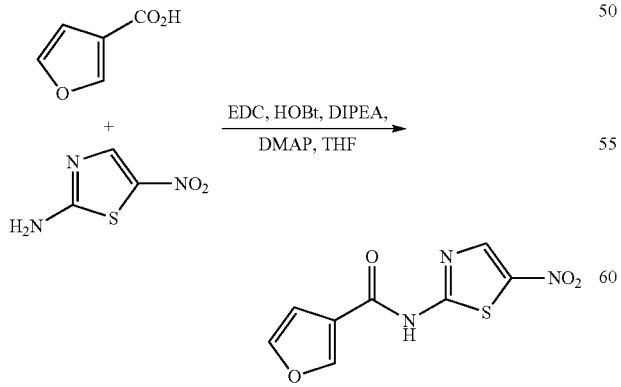

N-(5-Nitrothiazol-2-yl)furan-3-carboxamide (VPC16a1006)

Method B with 3-furoic acid (100 mg, 0.89 mmol) afforded the title compound VPC16a1006 (105 mg, 49%) as a yellow solid. $^1$H NMR (300 MHz, DMSO-$d_6$) δ 13.44 (bs, 1H), 8.70 (s, 1H), 8.68 (dd, J=1.5, 0.8 Hz, 1H), 7.93-7.85 (m, 1H), 7.17-7.09 (m, 1H); $^{13}$C NMR (75 MHz, DMSO-$d_6$) δ 162.2, 161.1, 148.4, 145.1, 144.7, 142.6, 120.0, 109.1; HRMS (ESI) calcd for $[C_8H_5N_3O_4S+H]^+$ 240.0074. found 240.0082.

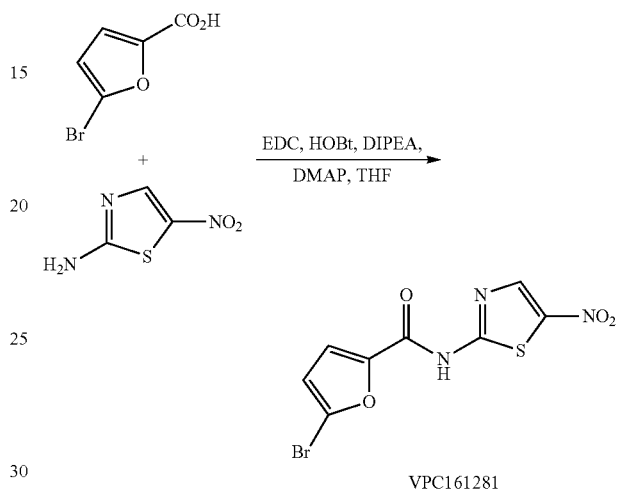

5-Bromo-N-(5-nitrothiazol-2-yl)furan-2-carboxamide (VPC161281)

Method B with 5-bromo-2-furoic acid (100 mg, 0.52 mmol) afforded the title compound VPC161281 (72 mg, 44%) as a red solid. $^1$H NMR (300 MHz, DMSO-$d_6$) δ 13.57 (bs, 1H), 8.63 (s, 1H), 7.73 (d, J=3.7 Hz, 1H), 6.89 (d, J=3.7 Hz, 1H); $^{13}$C NMR (75 MHz, DMSO-$d_6$) δ 161.9, 155.5, 146.6, 142.4, 142.1, 128.9, 120.5, 114.9; HRMS (ESI) calcd for $[C_8H_4BrN_3O_4S+H]^+$ 317.9179. found 317.918.

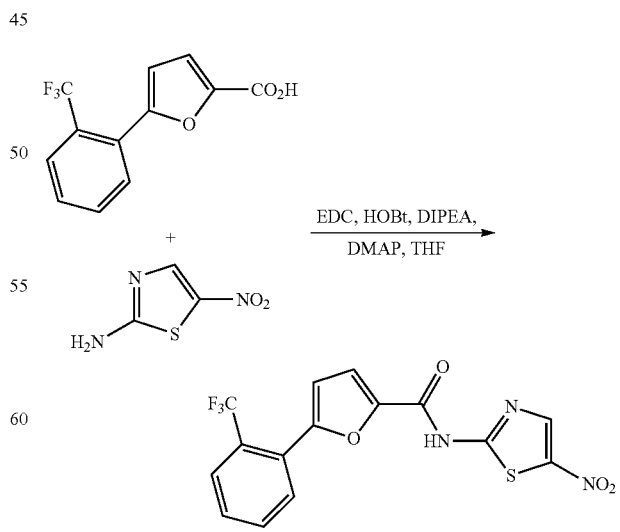

N-(5-Nitrothiazol-2-yl)-5-(2-(trifluoromethyl)phenyl)furan-2-carboxamide (VPC161196)

Method B with 5-(2-(trifluoromethyl)phenyl)-2-furoic acid (100 mg, 0.39 mmol) afforded the title compound VPC161196 (82 mg, 55%) as a bright yellow solid. ¹H NMR (500 MHz, DMSO-d₆) δ 13.78 (bs, 1H), 8.70 (s, 1H), 8.03 (d, J=7.7 Hz, 1H), 7.92 (d, J=7.8 Hz, 1H), 7.87 (d, J=3.8 Hz, 1H), 7.84 (t, J=7.6 Hz, 1H), 7.71 (t, J=7.7 Hz, 1H), 7.05 (d, J=3.7 Hz, 1H); ¹³C NMR (125 MHz, DMSO-d₆) δ 162.1, 156.3, 154.1, 144.9, 142.6, 142.1, 132.9, 131.1, 130.2, 127.2, 126.9 (q, $J_{CF}$=5.1 Hz), 125.8 (q, $J_{CF}$=31.7 Hz), 123.7 (q, $J_{CF}$=273 Hz), 119.9, 112.7; HRMS (ESI) calcd for [$C_{15}H_{8}F_{3}N_{3}O_{4}S$+H]⁺ 384.0260. found 384.0270.

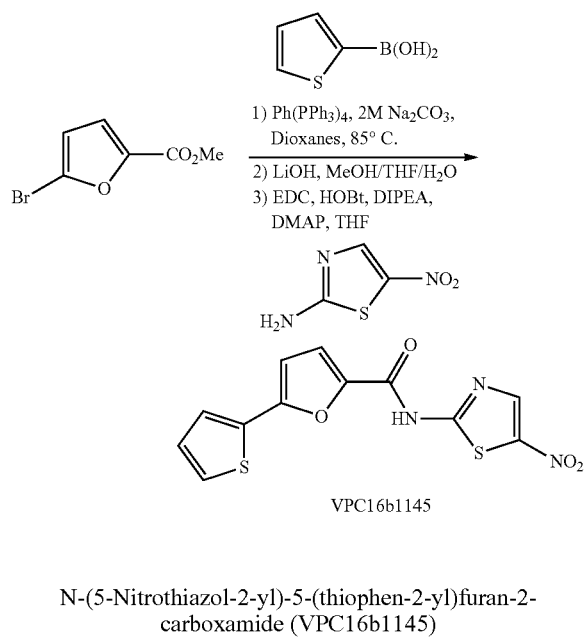

N-(5-Nitrothiazol-2-yl)-5-(thiophen-2-yl)furan-2-carboxamide (VPC16b1145)

Methyl 5-bromofuran-2-carboxylate (150 mg, 0.73 mmol), Pd(PPh₃)₄ (42 mg, 0.04 mmol), 2M Na₂CO₃ (0.73 ml, 1.46 mmol) and thiophen-2-ylboronic acid (121 mg, 0.95 mmol) in 1,4-dioxanes (7 ml) and was warmed to 90° C. The solution was then held at this temperature for 26 hours then cooled and washed with 1M HCl (2×20 mL), brine (2×20 mL) then dried (MgSO₄) followed by filtration and evaporation to dryness. The resulting residue was then purified by flash column chromatography (5% EtOAc/hexanes) to obtain methyl 5-(thiophen-2-yl)furan-2-carboxylate (138 mg, 91%) as a yellow oil. ¹H NMR (500 MHz, DMSO-d₆) δ 7.69 (dt, J=5.0, 0.9 Hz, 1H), 7.59 (dt, J=3.6, 0.8 Hz, 1H), 7.40 (dd, J=3.7, 0.6 Hz, 1H), 7.23-7.15 (m, 1H), 6.99 (d, J=3.7 Hz, 1H), 3.83 (s, 3H); ¹³C NMR (125 MHz, DMSO-d₆) δ 158.1, 152.5, 142.3, 131.2, 128.5, 127.7, 125.8, 120.7, 107.5, 51.8; HRMS (ESI) calcd for [$C_{10}H_{8}O_{3}S$+H]⁺ 209.0267. found 209.0272. Method D with methyl 5-(thiophen-2-yl)furan-2-carboxylate (100 mg, 0.48 mmol) afforded 5-(thiophen-2-yl)furan-2-carboxylic acid (92 mg, 99%) as a white solid. ¹H NMR (300 MHz, DMSO-d₆) δ 13.16 (bs, 1H), 7.68 (dd, J=5.0, 1.1 Hz, 1H), 7.56 (dd, J=3.6, 1.1 Hz, 1H), 7.30 (d, J=3.6 Hz, 1H), 7.18 (dd, J=5.0, 3.7 Hz, 1H), 6.95 (d, J=3.6 Hz, 1H); ¹³C NMR (125 MHz, DMSO-d₆) δ 159.1, 152.0, 143.5, 131.5, 128.5, 127.4, 125.5, 120.0, 107.4; HRMS (ESI) calcd for [$C_{9}H_{6}O_{3}S$+H]⁺ 195.0110. found 195.0112. Method B with 5-(thiophen-2-yl)furan-2-carboxylic acid (75 mg, 0.39 mmol) afforded the title compound VPC16b1145 (46 mg, 37%) as a yellow solid. ¹H NMR (300 MHz, DMSO-d₆) δ 13.69 (bs, 1H), 8.72 (s, 1H), 7.81 (d, J=3.8 Hz, 1H), 7.73 (t, J=4.4 Hz, 2H), 7.22 (dd, J=4.9, 3.7 Hz, 1H), 7.07 (d, J=3.8 Hz, 1H); ¹³C NMR (125 MHz, DMSO-d₆) δ 162.2, 156.0, 153.2, 143.2, 142.5, 141.9, 131.1, 128.4, 128.1, 126.5, 120.7, 107.8; HRMS (ESI) calcd for [$C_{12}H_{7}N_{3}O_{4}S_{2}$+H]⁺ 321.9951. found 321.9963.

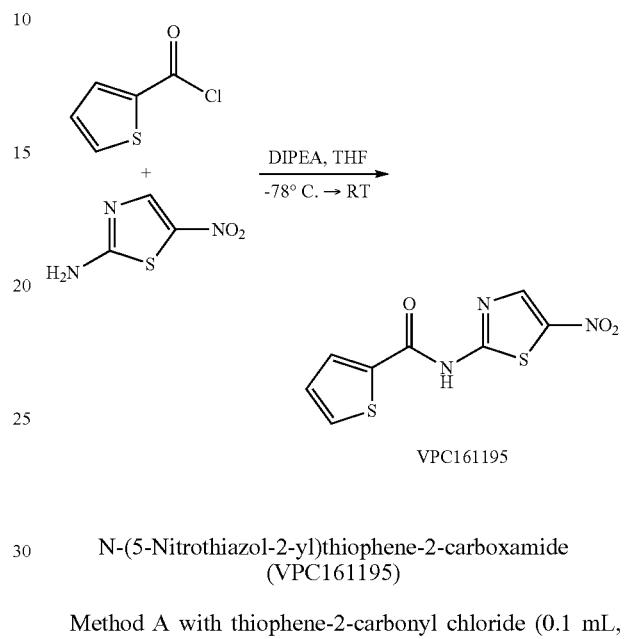

N-(5-Nitrothiazol-2-yl)thiophene-2-carboxamide (VPC161195)

Method A with thiophene-2-carbonyl chloride (0.1 mL, 0.94 mmol) afforded the title compound VPC161195 (85 mg, 36%) as a light yellow solid. ¹H NMR (300 MHz, DMSO-d₆) δ 13.70 (bs, 1H), 8.72 (s, 1H), 8.32 (dd, J=3.8, 1.1 Hz, 1H), 8.09 (dd, J=5.0, 1.1 Hz, 1H), 7.30 (dd, J=5.0, 3.9 Hz, 1H); ¹³C NMR (125 MHz, DMSO-d₆) δ 162.5, 160.8, 142.6, 142.0, 135.7, 135.3, 132.4, 128.9; HRMS (ESI) calcd for [$C_{8}H_{5}N_{3}O_{3}S_{2}$+H]⁺ 255.9845. found 255.9846.

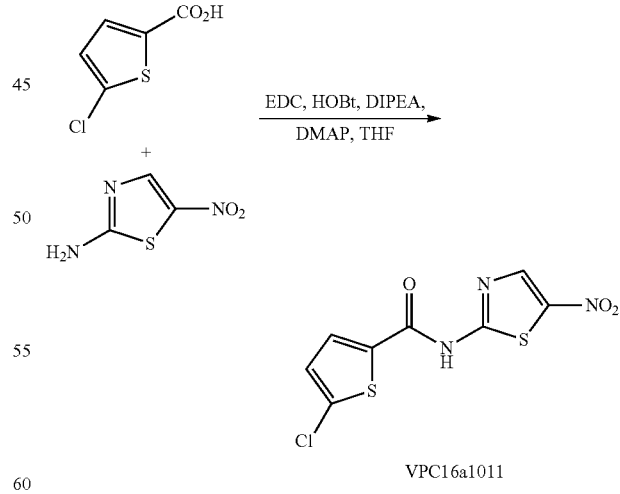

5-Chloro-N-(5-nitrothiazol-2-yl)thiophene-2-carboxamide (VPC16a1011)

Method B with 5-chlorothiophene-2-carboxylic acid (100 mg, 0.62 mmol) afforded the title compound VPC16a1011

(122 mg, 69%) as a yellow solid. $^1$H NMR (500 MHz, DMSO-$d_6$) δ 13.79 (s, 1H), 8.71 (s, 1H), 8.17 (d, J=4.2 Hz, 1H), 7.35 (d, J=4.2 Hz, 1H); $^{13}$C NMR (125 MHz, DMSO-$d_6$) δ 162.4, 160.0, 142.3, 142.0, 137.1, 134.9, 132.4, 129.1; HRMS (ESI) calcd for $[C_8H_4C_1N_3O_3S_2+H]^+$ 289.9455. found 289.9465.

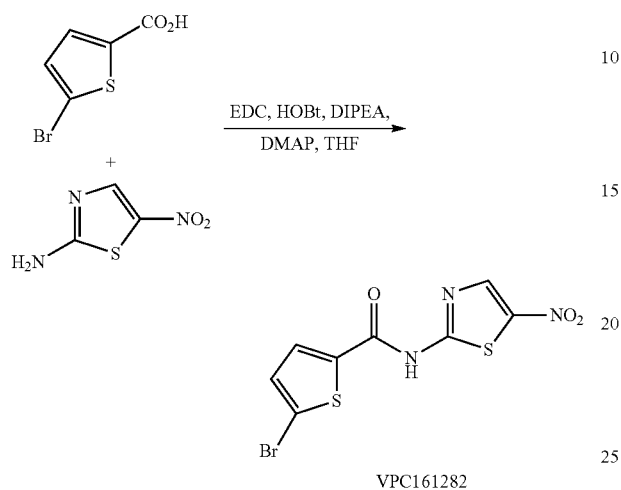

VPC161282

5-Bromo-N-(5-nitrothiazol-2-yl)thiophene-2-carboxamide (VPC161282)

Method B with 5-bromothiophene-2-carboxylic acid (100 mg, 0.48 mmol) afforded the title compound VPC161282 (128 mg, 75%) as a tan solid. $^1$H NMR (300 MHz, DMSO-$d_6$) δ 13.77 (bs, 1H), 8.71 (s, 1H), 8.11 (d, J=4.1 Hz, 1H), 7.44 (d, J=4.1 Hz, 1H); $^{13}$C NMR (75 MHz, DMSO-$d_6$) δ 162.3, 159.9, 142.3, 142.0, 137.5, 133.1, 132.5, 121.4; HRMS (ESI) calcd for $[C_8H_4BrN_3O_3S_2+H]^+$ 333.8950. found 333.8959.

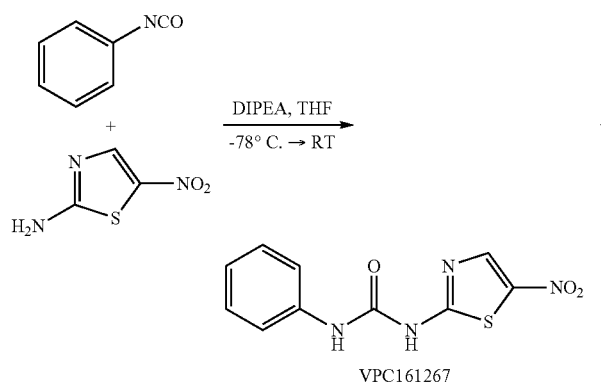

VPC161267

1-(5-Nitrothiazol-2-yl)-3-phenylurea (VPC161223)

Method A with 4-Fluorophenyl isocyanate (in place of acid chloride) (0.1 mL, 0.92 mmol) afforded the title compound VPC161223 (123 mg, 55%) as a tan solid. $^1$H NMR (300 MHz, DMSO-$d_6$) δ 11.58 (bs, 1H), 9.19 (s, 1H), 8.58 (s, 1H), 7.50 (d, J=8.5 Hz, 2H), 7.35 (t, J=7.7 Hz, 2H), 7.17-7.03 (m, 1H); $^{13}$C NMR (75 MHz, DMSO-$d_6$) δ 163.6, 151.4, 142.9, 141.2, 137.8, 129.1, 123.7, 119.2; HRMS (ESI) calcd for $[C_{10}H_8N_4O_3S+H]^+$ 265.0390. found 265.0398.

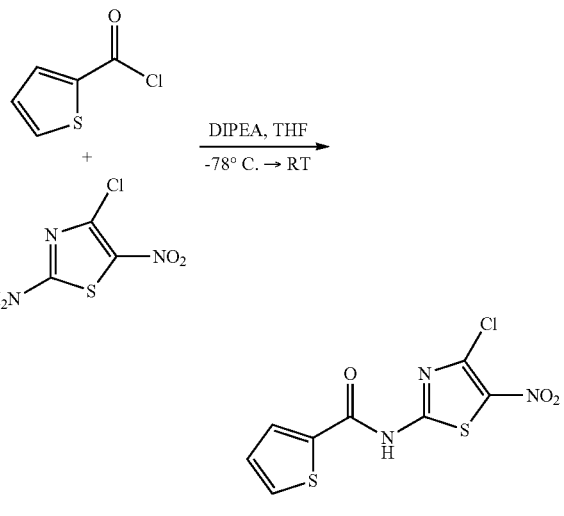

VPC162089

N-(4-Chloro-5-nitrothiazol-2-yl)thiophene-2-carboxamide (VPC162089)

Method A with thiophene-2-carbonyl chloride (0.05 mL, 0.42 mmol) and 2-amino-4-chloro-5-nitrothiazole[2] afforded the title compound VPC162089 (59 mg, 49%) as a yellow solid. $^1$H NMR (300 MHz, DMSO-$d_6$) δ 13.87 (bs, 1H), 8.28 (dd, J=3.8, 0.8 Hz, 1H), 8.09 (dd, J=4.9, 0.8 Hz, 1H), 7.29 (dd, J=4.8, 4.0 Hz, 1H); $^{13}$C NMR (75 MHz, DMSO-$d_6$) δ 161.2, 159.4, 138.2, 135.9, 135.2, 132.7, 129.0; HRMS (ESI) calcd for $[C_8H_4C_1N_3O_3S_2+H]^+$ 289.9455. found 289.9467.

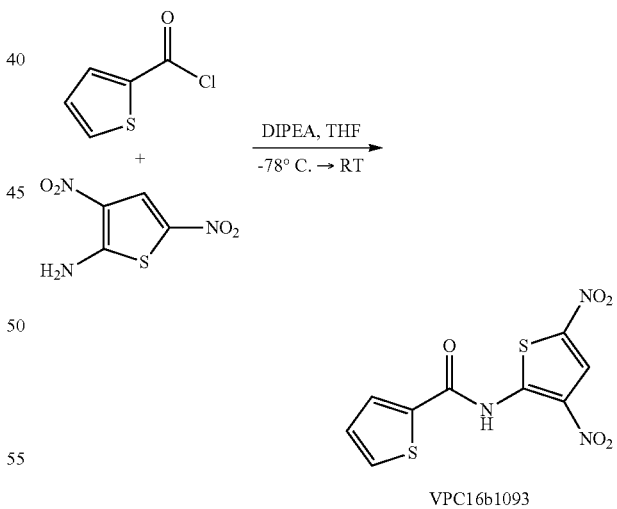

VPC16b1093

N-(3,5-Dinitrothiophen-2-yl)thiophene-2-carboxamide (VPC16b1093)

Method A with thiophene-2-carbonyl chloride (0.1 mL, 0.94 mmol) afforded the title compound VPC16b1093 (188 mg, 67%) as a brown solid. $^1$H NMR (500 MHz, DMSO-$d_6$) δ 8.52 (s, 1H), 8.15 (d, J=4.6 Hz, 1H), 8.05 (d, J=3.8 Hz, 1H), 7.34 (t, J=4.6 Hz, 1H); $^{13}$C NMR (125 MHz, DMSO-$d_6$) δ

160.2, 146.9, 138.9, 136.2, 134.4, 133.1, 130.2, 129.1, 123.2; HRMS (ESI) calcd for $[C_9H_5N_3O_5S_2+H]^+$ 299.9743. found 299.9755.

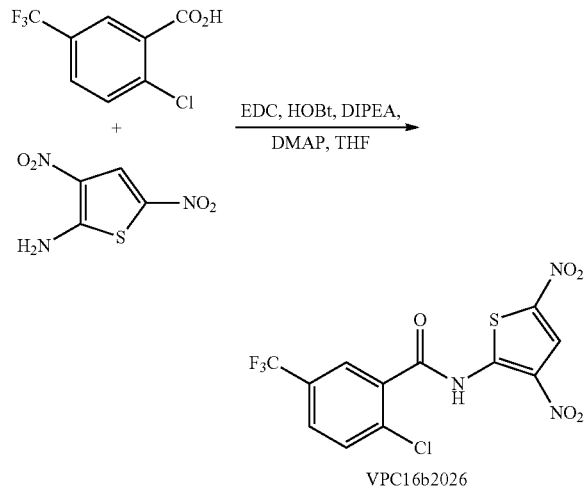

2-Chloro-N-(3,5-dinitrothiophen-2-yl)-5-(trifluoromethyl)benzamide (VPC16b2026)

Method B with 2-chloro-5-(trifluoromethyl)benzoic acid (100 mg, 0.45 mmol) afforded the title compound VPC16b2026 (99 mg, 56%) as an orange solid. $^1$H NMR (500 MHz, DMSO-d$_6$) δ 12.66 (bs, 1H), 8.54 (s, 1H), 8.20 (d, J=0.8 Hz, 1H), 8.00 (ddd, J=8.5, 1.5, 0.8 Hz, 1H), 7.89 (d, J=8.5 Hz, 1H); $^{13}$C NMR (125 MHz, DMSO-d$_6$) δ 165.4, 145.8, 139.3, 135.2, 133.7, 131.2, 130.7, 129.4, 127.9 (q, $J_{CF}$=33.0 Hz), 127.4, 123.4 (q, $J_{CF}$=271 Hz), 123.1; HRMS (ESI) calcd for $[C_{12}H_5ClF_3N_3O_5S+H]^+$ 395.9663. found 395.9658.

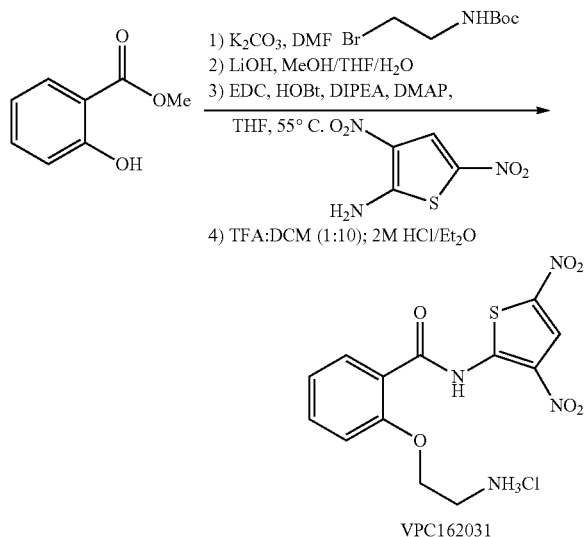

2-(2-Aminoethoxy)-N-(3,5-dinitrothiophen-2-yl) benzamide (VPC16b2031)

Method C with methyl 2-hydroxybenzoate (2.0 mL, 15.4 mmol) afforded methyl 2-(2-(tert-butoxycarbonylamino) ethoxy)benzoate (4.55 g, 99%) as an amber oil. $^1$H NMR (300 MHz, DMSO-d$_6$) δ 7.64 (dd, J=7.6, 1.1 Hz, 1H), 7.57-7.45 (m, 1H), 7.14 (d, J=8.4 Hz, 1H), 7.02 (t, J=7.5 Hz, 1H), 6.83 (t, J=5.3 Hz, 1H), 4.03 (t, J=5.9 Hz, 2H), 3.79 (s, 3H), 3.31 (q, J=5.8 Hz, 2H), 1.38 (s, 9H); $^{13}$C NMR (75 MHz, DMSO-d$_6$) δ 157.4, 155.6, 133.4, 130.7, 120.6, 120.5, 114.0, 77.8, 67.4, 51.8, 39.3, 31.4, 28.2, 27.6; HRMS (ESI) calcd for $[C_{15}H_{21}NO_5+Na]^+$ 318.1312. found 318.1319. Method D with ethyl 2-(2-(tert-butoxycarbonylamino)ethoxy)benzoate (240 mg, 0.81 mmol) afforded 2-(2-(tert-butoxycarbonylamino)ethoxy)benzoic acid (221 mg, 97%) as a white solid. $^1$H NMR (300 MHz, DMSO-d$_6$) δ 12.56 (s, 1H), 7.65 (dd, J=7.6, 1.7 Hz, 1H), 7.48 (td, J=8.3, 1.7 Hz, 1H), 7.13 (d, J=8.4 Hz, 1H), 7.01 (t, J=7.5 Hz, 1H), 6.85 (t, J=5.3 Hz, 1H), 1.37 (s, 9H); $^{13}$C NMR (75 MHz, DMSO-d$_6$) δ 167.3, 157.3, 155.7, 133.1, 130.8, 121.7, 120.6, 114.1, 77.9, 67.6, 39.2, 28.2; HRMS (ESI) calcd for $[C_{14}H_{19}NO_5+Na]^+$ 304.115. found 304.1168. Method B 2-(2-(tert-butoxycarbonylamino) ethoxy)benzoic acid (250 mg, 1.15 mmol) afforded tert-butyl 2-(2-(3,5-dinitrothiophen-2-ylcarbamoyl)phenoxy)ethylcarbamate (325 mg, 68%) as an orange solid. $^1$H NMR (500 MHz, DMSO-d$_6$) δ 13.04 (s, 1H), 8.58 (s, 1H), 8.11 (d, J=6.6 Hz, 1H), 7.71 (dd, J=11.4, 4.3 Hz, 1H), 7.40 (d, J=8.4 Hz, 1H), 7.21 (t, J=7.5 Hz, 1H), 7.06 (t, J=5.7 Hz, 1H), 4.43 (t, J=4.8 Hz, 2H), 3.44 (q, J=4.7 Hz, 2H), 1.24 (s, 9H); $^{13}$C NMR (125 MHz, DMSO-d$_6$) δ 163.5, 157.3, 155.7, 146.6, 139.0, 136.3, 132.3, 130.1, 123.0, 121.8, 117.3, 113.9, 77.8, 69.1, 38.6, 28.0; HRMS (ESI) calcd for $[C_{18}H_{20}N_4O_8S+Na]^+$ 475.0894. found 475.0892. Method E with tert-butyl 2-(2-(3,5-dinitrothiophen-2-ylcarbamoyl)phenoxy)ethylcarbamate (51 mg, 0.11 mmol) afforded the title compound VPC16b2031 (40 mg, 91%) as a yellow solid. $^1$H NMR (500 MHz, DMSO-d$_6$) δ 12.77 (s, 1H), 8.55 (s, 1H), 8.46 (bs, 3H), 8.12 (dd, J=7.8, 1.5 Hz, 1H), 7.88-7.65 (m, 1H), 7.43 (d, J=8.5 Hz, 1H), 7.25 (t, J=7.5 Hz, 1H), 4.65 (t, J=4.8 Hz, 2H), 3.42 (bs, 2H); $^{13}$C NMR (125 MHz, DMSO-d$_6$) δ 163.5, 156.6, 146.9, 139.1, 136.4, 132.5, 129.9, 122.9, 122.2, 117.3, 113.7, 66.5, 37.6.

Additional Synthetic Schemes

FIGS. 15-30 provide synthetic Schemes for compounds of the invention. Schemes generating "lead" compounds in those Figures are marked with bold boxes.

Bibliography for General Experimental Procedures and Preparation of Compounds

[1] R. A. Forsch, J. E. Wright, A. Rosowsky, Bioorg. Med. Chem. 2002, 10, 2067.
[2] G. D. Beck, Stefan; Brandes, Wilhelm; Paulus, Wilfried, EPO402716 (A1) ed., 1990, p. 61.

Activity Tables for PFOR and for Biofilm:
MIC Testing by Broth Dilution.

A standard broth dilution protocol was used in 96 well microplates containing a standard dilution of the microorganism to be tested in 100 microliters of the appropriate medium. Appropriate medium: E. coli, LB medium; Staphylococcus strains, Trypticase Soy; and for H. pylori and C. jejuni, Brain Heart Infusion. The compounds to be tested were set at 32 µg/m in 200 microliters in well one and then serially diluted to provide a range from 32 to 0.06. The wells were scored visually at 24 h. The well where there was no growth was recorded as the MIC. Clostridium difficile was tested by agar diffusion and disk diffusion (Kirby Bower) methods under anaerobic conditions on Wilkins Chalgrin agar. In these assays, zone of inhibited growth was measured and compared by relative ratio to the zone recorded for NTZ. In the agar dilution the MIC was scored as the concentration of compound that completely inhibited bacterial growth.

Representative compounds of the invention were tested in a series of assays against a series of organisms as described above. The tables below (Tables 3-18) provide a parent structure and formula and the analogs and derivatives tested, as well as the results of the various assays used. The organisms tested include, *C. difficile, H. pylori, C. jejuni*, MRSA, *S. epidermidis*, and *E. coli. S. epidermidis* and *E. coli* were tested in the plank and biofilm assay. A disk diffusion assay was also used for *C. difficile*. Direct PFOR enzyme assays were also performed. All analogues and derivatives were not tested on every organism in every type of assay (the "-" in each table means that it was not tested).

The following types of compounds were made and tested:
Table 3—Aliphatic Derivatives of 2-amino-5-nitrothiazole
Table 4—Aliphatic Amine Analogues of 2-amino-5-nitrothiazole
Table 5—Amino Acid Analogues of 2-amino-5-nitrothiazole
Table 6—Anthranilic Analogues of 2-amino-5-nitrothiazole
Table 7—Pyridine Analogues of 2-amino-5-nitrothiazole
Table 8—Indole Analogues of 2-amino-5-nitrothiazole
Table 9—Carboxylic Acid Analogues of 2-amino-5-nitrothiazole
Table 10—Dimer-like Analogues of 2-amino-5-nitrothiazole
Table 11—Halide Analogues of 2-amino-5-nitrothiazole
Table 12—Monosubstituted Analogues of 2-amino-5-nitrothiazole
Table 13—Disubstituted Analogues of 2-amino-5-nitrothiazole
Table 14—Furan Analogues of 2-amino-5-nitrothiazole
Table 15—Thiophene Analogues of 2-amino-5-nitrothiazole
Table 16—Amide Isosteres of 2-amino-5-nitrothiazole
Table 17—Analogues of 2-amino-4-chloro-5-nitrothiazole
Table 18—Analogues of 2-amino-3,5-dinitrothiophene

| | Aliphatic Derivatives of 2-amino-5-nitrothiazole | | | | | | | | |
|---|---|---|---|---|---|---|---|---|---|
| | MIC (µM) | | | | | | | Disk Diffusion (%) | Direct PFOR Enzyme Assay (%) |
| R = | *C. difficile* | *H. pylori* | *C. jejuni* | MRSA | *S. epidermidis* Plank | *S. epidermidis* Biofilm | *E. coli* Plank | *E. coli* Biofilm | *C. difficile* | |
| Nitazoxanide (o-OAc phenyl) | 52.1 | 13.0 | 39.1 | 39.1 | 52.1 | 32.5 | 104.1 | 26.0 | 100 | 100 |
| VPC161178 (phenyl) | — | 1.3 | 3.0 | 12.0 | 32.1 | 32.1 | 128.4 | 128.4 | 78 ± 3 | 73 |
| VPC16a1010 (cyclohexyl) | 62.6 | 0.7 | 11.4 | 125.2 | 31.3 | — | 125.2 | 31.3 | 53 ± 3 | 93 |
| VPC16a1013 (n=1, benzyl) | — | 21.6 | 1.8 | 121.5 | 22.8 | — | 121.5 | — | — | — |
| VPC16b1030 (n=2, phenethyl) | — | 0.3 | 1.30 | 115.4 | 14.4 | — | 115.4 | 50.5 | 54.5 ± 0.5 | — |

-continued

Aliphatic Derivatives of 2-amino-5-nitrothiazole

| R = | MIC (μM) | | | | | | | | Disk Diffusion (%) | Direct PFOR Enzyme Assay |
|---|---|---|---|---|---|---|---|---|---|---|
| | C. difficile | H. pylori | C. jejuni | MRSA | S. epidermidis | | E. coli | | C. difficile | (%) |
| | | | | | Plank | Biofilm | Plank | Biofilm | | |
| n = 3 VPC16a1020 | — | 13.8 | 2.6 | 109.8 | 109.8 | — | 109.8 | 54.9 | 33 ± 3 | — |
| VPC16b1032 | — | 1.7 | 26.6 | 13.8 | 13.8 | — | 110.6 | — | — | — |
| VPC16a1018 | — | 0.7 | 10.7 | 106.2 | 106.2 | 26.5 | 106.2 | 53.1 | — | — |
| VPC16a1033 | — | 3.5 | 14.0 | 171.0 | 21.4 | 21.4 | 42.7 | 42.7 | — | — |
| n = 2 VPC16b1045 | — | 0.5 | 2.1 | 148.7 | 37.2 | 4.6 | 148.7 | 148.7 | — | — |
| n = 4 VPC16a1007 | 65.8 | 1.4 | 5.5 | 131.5 | 32.9 | — | 131.5 | 131.5 | 56.5 ± 0.5 | 123 |
| n = 6 VPC16b1046 | — | 0.8 | 106.9 | 59.0 | 11.1 | 7.4 | 117.9 | 88.4 | 54 ± 4 | — |
| n = 8 VPC16b1043 | — | 1.2 | 3.9 | 106.9 | 106.9 | 1.7 | 106.9 | 106.9 | — | — |

-continued

Aliphatic Derivatives of 2-amino-5-nitrothiazole

| R = | MIC (μM) | | | | | | | | Disk Diffusion (%) C. difficile | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | | |
| VPC161200 (styryl) | — | 0.3 | 2.7 | 116.2 | 29.1 | 14.5 | 116.2 | 116.2 | — | 93 |
| VPC161239 (4-CF₃ styryl) | — | 0.6 | 93.2 | 93.2 | 2.9 | — | 93.2 | — | — | — |

Aliphatic Amine Analogues of 2-amino-5-nitrothiazole

| R = | MIC (μM) | | | | | | | | Disk Diff (%) C. difficile | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | | |
| Nitazoxanide | 52.1 | 13.0 | 39.1 | 39.1 | 52.1 | 32.5 | 104.1 | 26.0 | 100 | 100 |
| n = 1; X = HCl VPC161219 | 46.4 | 0.7 | 17.4 | 92.8 | 92.8 | 46.4 | 69.6 | 46.4 | 88 ± 4 | 114 |
| n = 1; X = TFA VPC161219TFA | — | 1.88 | 14.2 | 75.8 | 75.8 | — | 75.8 | — | 81 | — |
| n = 2; X = HCl VPC162102HCl | — | 1.0 | 8.4 | 89.2 | 44.6 | — | 89.2 | — | 74 | — |
| n = 2; X = TFA VPC162102TFA | — | 0.9 | 13.8 | 73.3 | 73.3 | — | 73.3 | — | 79 | — |
| n = 3; X = HCl VPC162096HCl | — | 2.0 | 5.4 | 85.8 | 42.9 | — | 85.8 | — | 111 | — |
| n = 3; X = TFA VPC162096TFA | — | 1.7 | 6.7 | 71.0 | 35.5 | — | 71.0 | — | 111 | — |

-continued

Aliphatic Amine Analogues of 2-amino-5-nitrothiazole

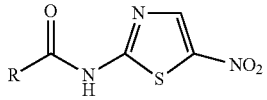

| R = | MIC (μM) | | | | | | | Disk Diff (%) | Direct PFOR Enzyme Assay (%) |
| --- | --- | --- | --- | --- | --- | --- | --- | --- | --- |
| | C. difficile | H. pylori | C. jejuni | MRSA | S. epidermidis Plank | S. epidermidis Biofilm | E. coli Plank | E. coli Biofilm | C. difficile | |

| R = | C. difficile | H. pylori | C. jejuni | MRSA | Plank | Biofilm | Plank | Biofilm | C. difficile | |
| --- | --- | --- | --- | --- | --- | --- | --- | --- | --- | --- |
| 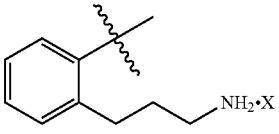<br>X = HCl<br>VPC162134 | — | 2.9 | 17.5 | 93.3 | 93.3 | — | — | — | — | 144 |
| 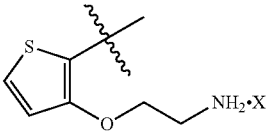<br>X = HCl<br>VPC162125 | — | 0.7 | 11.4 | 91.2 | 91.2 | — | 91.2 | — | — | 137 |
| 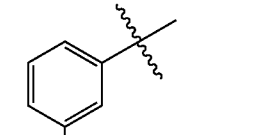<br>VPC16a1021 | — | 4.4 | 34.8 | 92.8 | 92.8 | — | 92.8 | — | — | — |
| 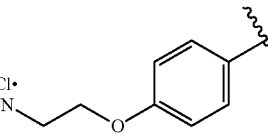<br>VPC16b1037 | — | 2.2 | 2.9 | 92.8 | 92.8 | 92.8 | 92.8 | 23.2 | 77 ± 4 | 78 |
| 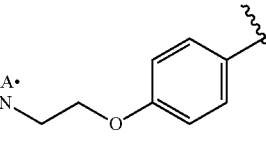<br>VPC16b1037TFA | — | 2.4 | 3.6 | 75.8 | 37.9 | — | 75.8 | — | 84 | — |
| 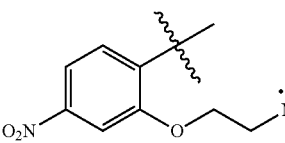<br>VPC161256 | — | 1.3 | 5.1 | 82.1 | 82.1 | — | 82.1 | — | — | — |

Aliphatic Amine Analogues of 2-amino-5-nitrothiazole

| R = | MIC (μM) | | | | | | | Disk Diff (%) | Direct PFOR Enzyme Assay |
|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | (%) |
| VPC162052 (2-OCH₂CH₂N(CH₃)₂-phenyl) | — | 1.5 | 17.8 | 95.1 | 95.1 | — | 95.1 | — | | — |
| VPC162044 (2-OCH₂CH₂NHC(O)CH₃-phenyl) | — | 1.1 | 34.3 | 91.3 | 22.8 | — | 91.3 | — | 77 | — |
| VPC162045 (2-OCH₂CH₂NHSO₂CH₃-phenyl) | — | 0.6 | 51.8 | 82.8 | 62.1 | — | 82.8 | — | 51 | — |
| VPC162049 (2-OCH₂CH₂NHC(O)Ph-phenyl) | — | 0.6 | 77.6 | 77.6 | 77.6 | — | 77.6 | — | 26 | — |
| VPC162048 (2-OCH₂CH₂NHC(O)NHPh-phenyl) | — | 0.4 | 74.9 | 74.9 | 74.9 | — | 74.9 | — | 31 | — |
| VPC162059 (R = Boc) | — | 0.7 | 61.6 | 61.6 | 61.6 | — | 61.6 | — | 38 | — |

Aliphatic Amine Analogues of 2-amino-5-nitrothiazole

| R = | MIC (μM) | | | | | | | Disk Diff (%) C. difficile | Direct PFOR Enzyme Assay (%) |
|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | | |

| R = | C. difficile | H. pylori | C. jejuni | MRSA | S. epi. Plank | S. epi. Biofilm | E. coli Plank | E. coli Biofilm | Disk Diff (%) | PFOR (%) |
|---|---|---|---|---|---|---|---|---|---|---|
| VPC162068 (2-phenoxyethyl-piperidine-4-carboxamide·HCl) | — | 52.6 | 35.1 | 70.2 | 70.2 | — | 70.2 | — | — | — |

Amino Acid Analogues of 2-amino-5-nitrothiazole

| R = | C. difficile | H. pylori | C. jejuni | MRSA | S. epi. Plank | S. epi. Biofilm | E. coli Plank | E. coli Biofilm | Disk Diffusion (%) C. difficile | Direct PFOR Enzyme Assay (%) |
|---|---|---|---|---|---|---|---|---|---|---|
| Nitazoxanide (2-OAc-phenyl) | 52.1 | 13.0 | 39.1 | 39.1 | 52.1 | 32.5 | 104.1 | 26.0 | 100 | 100 |
| VPC16a1027 (α-methylbenzylamine·HCl) | — | 76.3 | 38.1 | 101.7 | 101.7 | 101.7 | 101.7 | 25.4 | — | — |
| VPC16a1028 (phenylalaninyl·HCl) | — | 18.3 | 36.5 | 97.3 | 97.3 | 97.3 | 97.3 | 48.7 | — | — |
| VPC16a1032 (lysinyl·2HCl) | — | 69.3 | 92.4 | 92.4 | 92.4 | 92.4 | 92.4 | 0.1 | — | — |

| Anthranilic Analogues of 2-amino-5-nitrothiazole | | | | | | | | | | |
|---|---|---|---|---|---|---|---|---|---|---|
| | | MIC (μM) | | | | | | | Disk Diffusion (%) | Direct PFOR Enzyme Assay |
| | | C. | H. | C. | | S. epidermidis | | E. coli | | |
| R = | | difficile | pylori | jejuni | MRSA | Plank | Biofilm | Plank | Biofilm | C. difficile | (%) |
| Nitazoxanide (OAc) | | 52.1 | 13.0 | 39.1 | 39.1 | 52.1 | 32.5 | 104.1 | 26.0 | 100 | 100 |
| VPC162055 (NH₂) | | — | 2.4 | 11.4 | 121.1 | 90.8 | — | 45.4 | — | 83 | — |
| VPC162046b (NHAc) | | — | 6.9 | 41.6 | 55.5 | 111.0 | — | 111.0 | — | — | — |
| VPC162047 (NHBoc) | | — | 0.3 | 27.4 | 5.5 | 5.5 | — | 87.8 | — | 83 | — |

| Pyridine Analogues of 2-amino-5-nitrothiazole | | | | | | | | | | |
|---|---|---|---|---|---|---|---|---|---|---|
| | | MIC (μM) | | | | | | | Disk Diffusion (%) | Direct PFOR Enzyme Assay |
| | | C. | H. | C. | | S. epidermidis | | E. coli | | |
| R = | | difficile | pylori | jejuni | MRSA | Plank | Biofilm | Plank | Biofilm | C. difficile | (%) |
| Nitazoxanide (OAc) | | 52.1 | 13.0 | 39.1 | 39.1 | 52.1 | 32.5 | 104.1 | 26.0 | 100 | 100 |

Pyridine Analogues of 2-amino-5-nitrothiazole

| R = | MIC (μM) | | | | | | | | Disk Diffusion (%) | Direct PFOR Enzyme Assay |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | (%) |
| VPC161177 (4-pyridyl) | — | 16.0 | 24.0 | 127.9 | 127.9 | 127.9 | 127.9 | 127.9 | — | — |
| VPC161176 (3-pyridyl) | — | 4.0 | 71.9 | 127.9 | 127.9 | 63.9 | 127.9 | 127.9 | — | — |
| VPC16a1053 (3-F-4-pyridyl) | — | 3.7 | 14.9 | 119.3 | 119.3 | — | 119.3 | — | — | — |
| VPC16a1052 (2-F-3-pyridyl) | — | 3.7 | 7.5 | 119.3 | 119.3 | — | 119.3 | — | 100 | 91 |

Indole Analogues of 2-amino-5-nitrothiazole

| R = | MIC (μM) | | | | | | | | Disk Diffusion (%) | Direct PFOR Enzyme Assay |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | (%) |
| Nitazoxanide (2-OAc-phenyl) | 52.1 | 13.0 | 39.1 | 39.1 | 52.1 | 32.5 | 104.1 | 26.0 | 100 | 100 |

Indole Analogues of 2-amino-5-nitrothiazole

R-C(=O)-NH-[thiazole]-NO₂

| R = | MIC (μM) C. difficile | H. pylori | C. jejuni | MRSA | S. epidermidis Plank | S. epidermidis Biofilm | E. coli Plank | E. coli Biofilm | Disk Diffusion (%) C. difficile | Direct PFOR Enzyme Assay (%) |
|---|---|---|---|---|---|---|---|---|---|---|
| VPC16a1014 (3-indolyl, N-CH₃) | — | 1.2 | 19.9 | 105.9 | 5.0 | — | 105.9 | — | — | — |
| VPC16b1028 (2-indolyl, N-CH₃) | — | 1.2 | 39.7 | 105.9 | 105.9 | — | 105.9 | — | — | — |
| VPC16b1031 (2-indolyl, NH) | — | 6.9 | 13.9 | 27.8 | 13.9 | — | 111.0 | — | 75 | — |

Carboxylic Acid Analogues of 2-amino-5-nitrothiazole

R-C(=O)-NH-[thiazole]-NO₂

| R = | MIC (μM) C. difficile | H. pylori | C. jejuni | MRSA | S. epidermidis Plank | S. epidermidis Biofilm | E. coli Plank | E. coli Biofilm | Disk Diffusion (%) C. difficile | Direct PFOR Enzyme Assay (%) |
|---|---|---|---|---|---|---|---|---|---|---|
| Nitazoxanide (2-OAc phenyl) | 52.1 | 13.0 | 39.1 | 39.1 | 52.1 | 32.5 | 104.1 | 26.0 | 100 | 100 |
| VPC161273 (HOOC-CH₂CH₂CH₂-) | — | 5.8 | 123.4 | 123.4 | 123.4 | 123.4 | 123.4 | 61.7 | — | — |

-continued
Carboxylic Acid Analogues of 2-amino-5-nitrothiazole
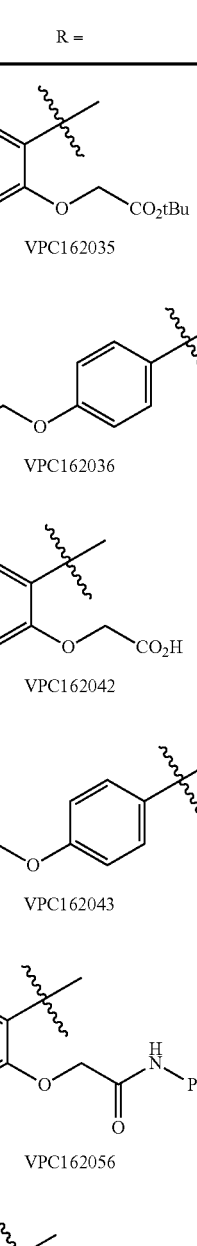
| R = | C. difficile | H. pylori | C. jejuni | MRSA | S. epidermidis Plank | S. epidermidis Biofilm | E. coli Plank | E. coli Biofilm | Disk Diffusion (%) C. difficile | Direct PFOR Enzyme Assay (%) |
|---|---|---|---|---|---|---|---|---|---|---|
| 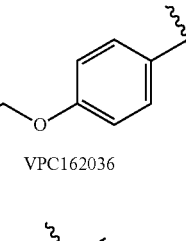 VPC162035 | — | 1.0 | 84.4 | 84.3 | 84.3 | — | 84.3 | — | 0 | — |
| 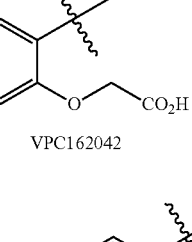 VPC162036 | — | 0.5 | 84.4 | 84.3 | 84.3 | — | 84.3 | — | — | — |
| 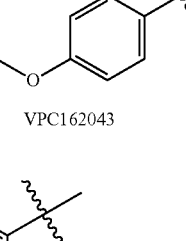 VPC162042 | — | 49.5 | 99.0 | 99.0 | 99.0 | — | 99.0 | — | — | — |
| 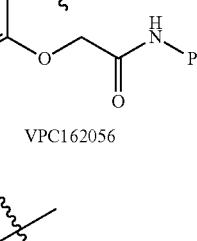 VPC162043 | — | 99.0 | 99.0 | 99.0 | 99.0 | — | 99.0 | — | — | — |
| 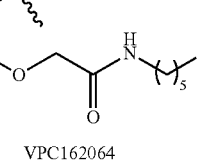 VPC162056 | — | 0.9 | 80.3 | 80.3 | 80.3 | — | 80.3 | — | — | — |
|  VPC162064 | — | 1.9 | 78.7 | 78.7 | 4.9 | — | 78.7 | — | — | — |

| Carboxylic Acid Analogues of 2-amino-5-nitrothiazole | | | | | | | | | |
|---|---|---|---|---|---|---|---|---|---|
| | | MIC (μM) | | | | | | Disk Diffusion (%) | Direct PFOR Enzyme Assay |
| | C. | H. | C. | | S. epidermidis | | E. coli | | |
| R = | difficile | pylori | jejuni | MRSA | Plank | Biofilm | Plank | Biofilm | C. difficile | (%) |
| VPC162065 | — | 2.3 | 36.7 | 73.5 | 27.6 | — | 73.5 | — | — | — |
| VPC162082 | — | 6.2 | 29.8 | 79.4 | 79.4 | — | 79.4 | — | — | — |
| VPC162083 | — | 24.1 | 77.1 | 77.1 | 77.1 | — | 77.1 | — | — | — |

| Dimer-like Analogues of 2-amino-5-nitrothiazole | | | | | | | | | |
|---|---|---|---|---|---|---|---|---|---|
| | | MIC (μM) | | | | | | Disk Diffusion (%) | Direct PFOR Enzyme Assay |
| | C. | H. | C. | | S. epidermidis | | E. coli | | C. |
| R = | difficile | pylori | jejuni | MRSA | Plank | Biofilm | Plank | Biofilm | difficile | (%) |
| Nitazoxanide | 52.1 | 13.0 | 39.1 | 39.1 | 52.1 | 32.5 | 104.1 | 26.0 | 100 | 100 |

-continued

Dimer-like Analogues of 2-amino-5-nitrothiazole

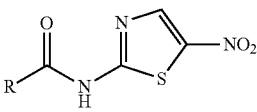

| R = | MIC (μM) | | | | | | | | Disk Diffusion (%) | Direct PFOR Enzyme Assay (%) |
|---|---|---|---|---|---|---|---|---|---|---|
| | *C. difficile* | *H. pylori* | *C. jejuni* | MRSA | *S. epidermidis* Plank | *S. epidermidis* Biofilm | *E. coli* Plank | *E. coli* Biofilm | *C. difficile* | |
| VPC16b1048 | — | 20.7 | 82.8 | 82.8 | 82.8 | 41.4 | 82.8 | 82.8 | — | — |
| VPC161276 | — | 5.2 | 31.1 | 82.8 | 82.8 | 1.3 | 82.8 | 82.8 | — | — |
| VPC161277 | — | 1.8 | 29.1 | 77.6 | 77.6 | 2.4 | 77.6 | 77.6 | — | — |

Halide Analogues of 2-amino-5-nitrothiazole

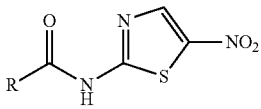

| R = | MIC (μM) | | | | | | | | Disk Diffusion (%) | Direct PFOR Enzyme Assay (%) |
|---|---|---|---|---|---|---|---|---|---|---|
| | *C. difficile* | *H. pylori* | *C. jejuni* | MRSA | *S. epidermidis* Plank | *S. epidermidis* Biofilm | *E. coli* Plank | *E. coli* Biofilm | *C. difficile* | |
| Nitazoxanide | 52.1 | 13.0 | 39.1 | 39.1 | 52.1 | 32.5 | 104.1 | 26.0 | 100 | 100 |
| $R_1$ = F; $R_{2-5}$ = H VPC161152 | — | 0.5 | 5.6 | 18.7 | 119.7 | 59.9 | 119.7 | 119.7 | — | — |
| $R_2$ = F; $R_{1,3-5}$ = H VPC161166 | — | 0.9 | 11.2 | 16.8 | 22.5 | 59.9 | 119.7 | 59.9 | — | — |

-continued

Halide Analogues of 2-amino-5-nitrothiazole

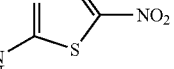

| R = | C. difficile | H. pylori | C. jejuni | MRSA | S. epidermidis Plank | S. epidermidis Biofilm | E. coli Plank | E. coli Biofilm | Disk Diffusion (%) C. difficile | Direct PFOR Enzyme Assay (%) |
|---|---|---|---|---|---|---|---|---|---|---|
| $R_3$ = F; $R_{1,2,4,5}$ = H VPC161167 | — | 0.9 | 2.8 | 8.4 | 15.0 | 29.9 | 119.7 | 119.7 | 89 | 99 |
| $R_{1,3}$ = F; $R_{2,4,5}$ = H VPC16b1009 | — | 0.4 | 7.0 | 28.0 | 42.1 | — | 112.2 | — | — | — |
| $R_{3,4}$ = F; $R_{1,2,5}$ = H VPC16b1019 | — | 1.8 | 5.3 | 10.5 | 28.0 | — | 84.1 | — | — | — |
| $R_{1,5}$ = F; $R_{2-4}$ = H VPC16b1010 | — | 0.7 | 14.0 | 28.0 | 28.0 | — | 112.2 | — | — | — |
| $R_{1,3,5}$ = F; $R_{2,4}$ = H VPC16b1011 | — | 4.9 | 9.9 | 39.6 | 52.8 | — | 105.5 | — | — | — |
| $R_{2-4}$ = F; $R_{1,5}$ = H VPC16b1014 | — | 1.2 | 4.9 | 29.7 | 66.0 | — | 105.5 | — | — | — |
| $R_{1,3,4}$ = F; $R_{2,5}$ = H VPC16b1012 | — | 0.8 | 9.9 | 33.0 | 33.0 | — | 105.5 | — | — | — |
| $R_{1-4}$ = F; $R_5$ = H VPC16b1013 | — | 1.2 | 4.7 | 6.2 | 12.5 | — | 99.6 | — | — | — |
| $R_{2-5}$ = F VPC161108 | — | 7.4 | 23.6 | 8.8 | 47.2 | 6.6 | 94.3 | 47.2 | — | — |
| $R_1$ = Cl; $R_{2-5}$ = H VPC161162 | — | 0.3 | 7.8 | 3.9 | 20.9 | 20.9 | 83.4 | 83.4 | — | — |
| $R_2$ = Cl; $R_{1,3-5}$ = H VPC161157 | — | 1.0 | 6.5 | 7.8 | 31.3 | 20.9 | 83.4 | 41.7 | — | — |
| $R_3$ = Cl; $R_{1,2,4,5}$ = H VPC161160 | — | 0.7 | 6.5 | 2.0 | 26.1 | 5.2 | 62.6 | 41.7 | — | — |

Monosubstituted Analogues of 2-amino-5-nitrothiazole

| R = | C. difficile | H. pylori | C. jejuni | MRSA | S. epidermidis Plank | S. epidermidis Biofilm | E. coli Plank | E. coli Biofilm | Disk Diff (%) C. difficile | Direct PFOR Assay (%) |
|---|---|---|---|---|---|---|---|---|---|---|
| Nitazoxanide (2-OAc phenyl) | 52.1 | 13.0 | 39.1 | 39.1 | 52.1 | 32.5 | 104.1 | 26.0 | 100 | 100 |
| $R_2$ = CN; $R_{1,3-5}$ = H VPC161173 | — | 4.1 | 36.5 | 43.8 | 29.2 | 58.3 | 116.7 | 116.7 | — | — |
| $R_3$ = CN; $R_{1,2,4,5}$ = H VPC160186 | — | 9.1 | 43.8 | 14.6 | 21.9 | 4.6 | 87.5 | 58.3 | — | 74 |
| $R_1$ = $CF_3$; $R_{2-5}$ = H VPC161182 | — | 1.6 | 18.9 | 25.2 | 25.2 | 50.4 | 100.9 | 100.9 | — | — |

| Monosubstituted Analogues of 2-amino-5-nitrothiazole | | | | | | | | | | |
|---|---|---|---|---|---|---|---|---|---|---|
| | | MIC (μM) | | | | | | | Disk Diff (%) | Direct PFOR Enzyme Assay (%) |
| R = | C. difficile | H. pylori | C. jejuni | MRSA | S. epidermidis Plank | S. epidermidis Biofilm | E. coli Plank | E. coli Biofilm | C. difficile | |
| $R_2 = CF_3$; $R_{1,3-5} = H$ VPC161183 | 12.6 | 3.5 | 4.7 | 3.2 | 12.6 | 25.2 | 37.8 | 31.5 | 95 ± 2 | 87 |
| $R_3 = CF_3$; $R_{1,2,4,5} = H$ VPC161184 | — | 1.6 | 4.7 | 100.9 | 12.6 | 12.6 | 63.0 | 12.6 | 90 | — |
| $R_1 = NO_2$; $R_{2-5} = H$ VPC161168 | — | 1.7 | 27.2 | 108.8 | 40.8 | 68.0 | 108.8 | 108.8 | — | — |
| $R_2 = NO_2$; $R_{1,3-5} = H$ VPC161169 | — | 1.3 | 27.2 | 10.2 | 10.2 | 3.4 | 81.6 | 108.8 | — | — |
| $R_3 = NO_2$; $R_{1,2,4,5} = H$ VPC161170 | — | 1.3 | 13.6 | 20.4 | 10.2 | 3.4 | 81.6 | 108.8 | — | — |
| $R_1 = OMe$; $R_{2-5} = H$ VPC161192 | — | 1.8 | 17.9 | 114.6 | 114.6 | 114.6 | 114.6 | 57.3 | — | — |
| $R_2 = OMe$; $R_{1,3-5} = H$ VPC161193 | 28.6 | 1.3 | 7.2 | 14.3 | 28.6 | 57.3 | 114.6 | 114.6 | 73 ± 1 | 82 |
| $R_3 = OMe$; $R_{1,2,4,5} = H$ VPC161194 | — | 1.8 | 4.5 | 28.6 | 28.6 | 28.6 | 114.6 | 114.6 | — | 84 |
| $R_3 = C(O)CF_3$; $R_{1,2,4,5} = H$ VPC161175 | 23.2 | 4.3 | 69.5 | 92.7 | 92.7 | 92.7 | 92.7 | 92.7 | — | — |
| $R_2 = OCF_3$; $R_{1,3-5} = H$ VPC16a1041 | — | 1.1 | 9.0 | 6.0 | 12.0 | — | 96.0 | — | 90 | — |

| Disubstituted Analogues of 2-amino-5-nitrothiazole | | | | | | | | | | |
|---|---|---|---|---|---|---|---|---|---|---|
| | | MIC (μM) | | | | | | | Disk Diff (%) | Direct PFOR Enzyme Assay (%) |
| R = | C. difficile | H. pylori | C. jejuni | MRSA | S. epidermidis Plank | S. epidermidis Biofilm | E. coli Plank | E. coli Biofilm | C. difficile | |
| Nitazoxanide (2-OAc phenyl) | 52.1 | 13.0 | 39.1 | 39.1 | 52.1 | 32.5 | 104.1 | 26.0 | 100 | 100 |
| $R_1 = OAc$; $R_3 = CN$; $R_{2,4,5} = H$ VPC161076 | — | 24.1 | 96.3 | 96.3 | 96.3 | 48.2 | 96.3 | 96.3 | — | — |
| $R_4 = CF_3$; $R_5 = Cl$; $R_{1-3} = H$ VPC16a1059 | — | 0.9 | 92.1 | 92.1 | 92.1 | 92.1 | 92.1 | 92.1 | — | — |
| $R_1 = OMe$; $R_3 = NO_2$; $R_{2,4,5} = H$ VPC161093 | 98.7 | 0.6 | 9.3 | 98.7 | 12.3 | 12.3 | 98.7 | 98.7 | — | 115 |

Disubstituted Analogues of 2-amino-5-nitrothiazole

| R = | MIC (μM) | | | | | | | | Disk Diff (%) | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| $R_1$ = OMe; $R_4$ = o,p-DifluroPh; $R_{2,3,5}$ = H VPC161171 | — | 0.8 | 40.9 | 81.8 | 81.8 | 81.8 | 81.8 | 81.8 | — | — |
| $R_1$ = OH; $R_2$ = $NO_2$; $R_{3-5}$ = H VPC161090 | — | 19.3 | 103.1 | 103.1 | 77.4 | 6.4 | 103.1 | 103.1 | — | — |
| $R_1$ = $CF_3$; $R_3$ = F; $R_{2,4,5}$ = H VPC161127 | — | 3.4 | 23.9 | 8.9 | 23.9 | 13.4 | 95.5 | 95.5 | — | — |
| $R_1$ = $NO_2$; $R_3$ = $CF_3$; $R_{2,4,5}$ = H VPC16b1016 | — | 8.3 | 88.3 | 88.3 | 88.3 | — | 88.3 | 88.3 | — | — |
| $R_2$ = $NO_2$; $R_3$ = F; $R_{1,5,6}$ = H VPC16b1017 | — | 1.6 | 51.2 | 76.9 | 51.2 | — | 102.5 | 102.5 | — | — |
| $R_{2,4}$ = $CF_3$; $R_{1,3,5}$ = H VPC16a1039 | — | 5.2 | 41.5 | 2.6 | 1.9 | — | 83.1 | — | 80 | 54* |
| $R_1$ = Cl; $R_4$ = $CF_3$; $R_{2,3,5}$ = H VPC16a1040 | — | 1.1 | 17.1 | 22.7 | 22.7 | — | 91.0 | — | 90 | 68 |
| $R_4$ = $CF_3$; $R_5$ = Cl; $R_{1-3}$ = H VPC16a1059 | — | 0.9 | 5.7 | 11.4 | 11.4 | — | 91.0 | — | 90 | — |
| $R_3$ = Cl; $R_4$ = $CF_3$; $R_{1,2,5}$ = H VPC16a1060 | — | 2.8 | 2.8 | 2.8 | 2.8 | — | 91.0 | — | 89 | 63* |

*Caused some precipitate in extract

Furan Analogues of 2-amino-5-nitrothiazole

| R = | MIC (μM) | | | | | | | | Disk Diff (%) | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| Nitazoxanide (2-OAc phenyl) | 52.1 | 13.0 | 39.1 | 39.1 | 52.1 | 32.5 | 104.1 | 26.0 | 100 | 100 |
| VPC161144 (benzofuran-2-yl) | — | 0.6 | 110.6 | 57.0 | 110.6 | 110.6 | 110.6 | 110.6 | — | 70 |
| VPC16a1019 (5-nitrobenzofuran-2-yl) | — | 4.5 | 4.5 | 47.9 | 23.9 | — | 95.7 | — | 77 | — |

Furan Analogues of 2-amino-5-nitrothiazole

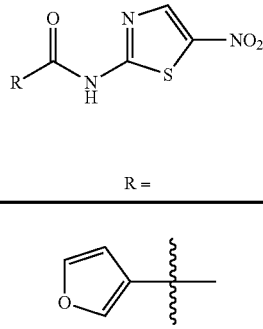

| R = | MIC (μM) | | | | | | | | Disk Diff (%) | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| 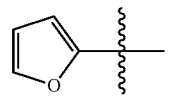 VPC16a1006 | 33.4 | 0.8 | 12.5 | 50.2 | 33.4 | — | 133.8 | 133.8 | 97 ± 3 | 98 |
| 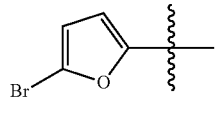 VPC161124 | — | 1.0 | 8.4 | 50.2 | 66.9 | 66.9 | 133.8 | 33.4 | 100 | 82 |
| 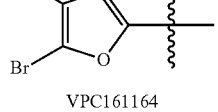 VPC161281 | — | 1.6 | 12.6 | 6.3 | 25.1 | 50.3 | 100.6 | 0.4 | 92 | — |
| 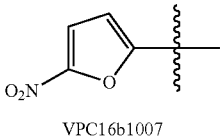 VPC161164 | — | 2.8 | 20.2 | 3.8 | 15.1 | 20.2 | 60.5 | 40.3 | — | 56 |
| 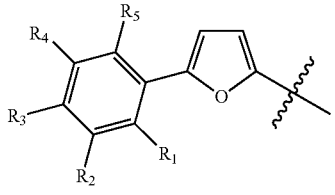 VPC16b1007 | 28.2 | 21.1 | 7.0 | 112.6 | 28.1 | 56.3 | 14.1 | 26.4 | 102 ± 8 | — |
| $R_{1-5}$ = H VPC16c1020 | — | 2.4 | 101.5 | 101.5 | 101.5 | — | 101.5 | — | — | — |
| $R_3$ = $NO_2$; $R_{1,2,4,5}$ = H VPC161189 | — | 6.9 | 16.7 | 88.8 | 11.1 | 11.1 | 88.8 | 88.8 | — | — |
| $R_2$ = $NO_2$; $R_{1,3-5}$ = H VPC161190 | — | 6.9 | 16.7 | 44.4 | 11.1 | 11.1 | 88.8 | 88.8 | — | — |
| $R_1$ = $CF_3$; $R_{2-5}$ = H VPC161196 | — | 1.1 | 8.5 | 2.8 | 5.7 | 5.7 | 90.8 | 90.8 | 70.5 ± 0.5 | — |
| $R_2$ = $CF_3$; $R_{1,3-5}$ = H VPC161197 | — | 1.1 | 8.5 | 11.4 | 5.7 | 5.7 | 90.8 | 90.8 | — | — |
| $R_1$ = $CH_3$; $R_{2-5}$ = H VPC16a1103 | — | 3.8 | 24.3 | 12.1 | 12.1 | — | 97.2 | — | — | — |
| $R_2$ = $CH_3$; $R_{1,3-5}$ = H VPC16b2014 | — | 2.3 | 97.2 | 97.2 | 97.2 | — | 97.2 | — | — | — |
| $R_3$ = $CH_3$; $R_{1,2,4,5}$ = H VPC16b2019 | — | 1.5 | 97.2 | 97.2 | 97.2 | — | 97.2 | — | — | — |
| $R_2$ = F; $R_{1,3-5}$ = H VPC16b1115 | — | 1.5 | 24.0 | 24.0 | 12.0 | — | 96.0 | — | — | — |

-continued

Furan Analogues of 2-amino-5-nitrothiazole

| R = | MIC (μM) | | | | | | | Disk Diff (%) | Direct PFOR Enzyme Assay (%) |
|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| $R_3$ = F; $R_{1,2,4,5}$ = H<br>VPC16a1104 | — | 1.0 | 96.0 | 96.0 | 96.0 | — | — | — | — | 81 |
| $R_1$ = Cl; $R_{2-5}$ = H<br>VPC16b1118 | — | 1.4 | 11.4 | 11.4 | 5.7 | — | 91.5 | — | — | — |
| $R_2$ = Cl; $R_{1,3-5}$ = H<br>VPC16b1119 | — | 1.1 | 22.9 | 91.5 | 91.5 | — | 91.5 | — | — | — |
| $R_3$ = Cl; $R_{1,2,4,5}$ = H<br>VPC16a1012 | — | 1.1 | 8.6 | 2.9 | 2.9 | — | 91.5 | — | 60.5 ± 4.5 | — |
| $R_3$ = OMe; $R_{1,2,4,5}$ = H<br>VPC16b1139 | — | 1.5 | 92.7 | 92.7 | 92.7 | — | 92.7 | — | — | — |
| $R_{3-4}$ = —OCH$_2$O—;<br>$R_{1,2,5}$ = H<br>VPC16b1132 | — | 1.4 | 89.1 | 89.1 | 89.1 | — | 89.1 | — | — | — |
| VPC16b1145 | — | 1.9 | 12.5 | 12.4 | 12.4 | 12.4 | 99.6 | — | — | — |
| VPC16b1142 | — | 1.6 | 13.1 | 26.2 | 13.1 | — | 104.8 | — | — | — |
| VPC16b2022 | — | 6.2 | 99.6 | 99.6 | 99.6 | — | 99.6 | — | — | — |

Thiophene Analogues of 2-amino-5-nitrothiazole

| R = | MIC (μM) | | | | | | | Disk Diff (%) | Direct PFOR Enzyme Assay (%) |
|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| Nitazoxanide | 52.1 | 13.0 | 39.1 | 39.1 | 52.1 | 32.5 | 104.1 | 26.0 | 100 | 100 |

-continued

Thiophene Analogues of 2-amino-5-nitrothiazole

| R = | MIC (μM) | | | | | | | | Disk Diff (%) | Direct PFOR Enzyme Assay (%) |
|---|---|---|---|---|---|---|---|---|---|---|
| | C. difficile | H. pylori | C. jejuni | MRSA | S. epidermidis | | E. coli | | C. difficile | |
| | | | | | Plank | Biofilm | Plank | Biofilm | | |
| VPC161195 (2-thienyl) | 31.3 | 2.9 | 2.9 | 15.7 | 31.3 | 62.7 | 125.4 | 125.4 | 97 | 88 |
| VPC16a1011 (5-Cl-2-thienyl) | 6.9 | 5.2 | 6.9 | 10.4 | 27.6 | — | 110.5 | 0.9 | 89 | 65 |
| VPC161282 (5-Br-2-thienyl) | — | 3.0 | 9.9 | 4.5 | 23.9 | 47.9 | 95.8 | 0.1 | 90 | — |
| VPC16a1009 (3-Cl-2-thienyl) | — | 5.2 | 20.7 | 20.7 | 55.2 | — | 110.5 | — | — | — |
| VPC16a1008 (3-thienyl) | — | 0.7 | 5.9 | 23.5 | 15.7 | — | 125.4 | — | 100 | 96 |
| VPC161199 (2,5-diCl-3-thienyl) | 12.3 | 1.5 | 2.3 | 6.2 | 12.3 | 24.7 | 98.7 | 24.7 | 89 | 48 |
| VPC161280 (5-nitrothiazol-2-yl) | — | 6.6 | 13.3 | 53.1 | 5.0 | 6.6 | 39.8 | 3.3 | — | — |
| VPC161180 (benzothiophen-2-yl) | 13.1 | 2.5 | 9.8 | 6.6 | 13.1 | 19.7 | 104.8 | 104.8 | 81 | — |

-continued

Thiophene Analogues of 2-amino-5-nitrothiazole

| R = | MIC (μM) | | | | | | | | Disk Diff (%) | Direct PFOR Enzyme Assay |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | (%) |
| 3-Cl-benzothiophen-2-yl<br>VPC161181 | 11.8 | 2.2 | 5.9 | 2.9 | 5.9 | 11.8 | 94.2 | 94.2 | 72 | — |
| 6-F-benzothiophen-2-yl<br>VPC162037 | — | 3.1 | 6.2 | 61.9 | 49.5 | — | 99.0 | — | 70 | — |
| 3-Cl-6-F-benzothiophen-2-yl<br>VPC161115 | 11.2 | 1.0 | 5.6 | 2.1 | 5.6 | 0.1 | 89.4 | 5.6 | 44 | 96 |
| 5-MeO-6-F-benzothiophen-2-yl<br>VPC161259 | — | 2.1 | 11.3 | 11.3 | 11.3 | — | 90.6 | — | — | — |
| phenyl-thiophen-2-yl (substituted)<br>$R_2 = CH_3$; $R_{1,3\text{-}5} = H$<br>VPC16b2011 | — | 2.2 | 92.6 | 92.6 | 92.6 | — | 92.6 | — | — | — |
| $R_3 = CH_3$; $R_{1,2,4,5} = H$<br>VPC16b2020 | — | 0.9 | 92.6 | 92.6 | 92.6 | — | 92.6 | — | — | — |
| $R_2 = Cl$; $R_{1,3\text{-}5} = H$<br>VPC16c1033 | — | 0.7 | 5.5 | 87.5 | 87.5 | — | — | — | — | 84 |
| bithiophen-2-yl<br>VPC16b2021 | — | 3.0 | 94.8 | 94.8 | 94.8 | — | 94.8 | — | — | — |

-continued

Thiophene Analogues of 2-amino-5-nitrothiazole

| R = | MIC (μM) | | | | | | | Disk Diff (%) | Direct PFOR Enzyme Assay (%) |
|---|---|---|---|---|---|---|---|---|---|
| | C. difficile | H. pylori | C. jejuni | MRSA | S. epidermidis | | E. coli | | C. difficile |
| | | | | | Plank | Biofilm | Plank | Biofilm | |
| VPC16b1148 | — | 7.8 | 12.4 | 24.9 | 12.4 | — | 99.6 | — | — | — |
| VPC16b1154 | — | 3.0 | 94.8 | 94.8 | 94.8 | — | 94.8 | — | — | — |
| VPC161269 (R = NO₂) | — | 1.0 | 53.8 | 86.1 | 86.1 | 86.1 | 86.1 | 21.5 | — | — |
| VPC161235 | — | 12.8 | 102.3 | 102.3 | 102.3 | — | 102.3 | — | — | — |
| VPC161237 (R = p-NO₂Ph) | — | 73.6 | 73.6 | 73.6 | 73.6 | — | 73.6 | — | — | — |

| Amide Isosteres of 2-amino-5-nitrothiazole | | | | | | | | | | |
|---|---|---|---|---|---|---|---|---|---|---|
| | | MIC (μM) | | | | | | | Disk Diff (%) | Direct PFOR Enzyme |
| | | C. difficile | H. pylori | C. jejuni | MRSA | S. epidermidis | | E. coli | | C. difficile | Assay (%) |
| R = | | | | | | Plank | Biofilm | Plank | Biofilm | | |
|  Nitazoxanide | | 52.1 | 13.0 | 39.1 | 39.1 | 52.1 | 32.5 | 104.1 | 26.0 | 100 | 100 |
| 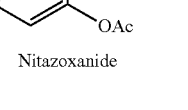 VPC161232 | | — | 6.0 | 8.0 | 32.1 | 16.0 | — | 128.4 | — | 0 | — |
| 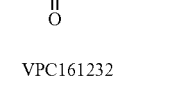 VPC161223 | | — | 1.4 | 30.3 | 30.3 | 30.3 | — | 121.1 | — | — | — |
| 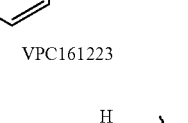 VPC161267 | | — | 0.9 | 21.3 | 56.7 | 28.3 | 28.3 | 113.4 | 56.7 | — | — |

| Analogues of 2-amino-4-chloro-5-nitrothiazole | | | | | | | | | | |
|---|---|---|---|---|---|---|---|---|---|---|
| 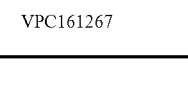 | | MIC (μM) | | | | | | | Disk Diff (%) | Direct PFOR Enzyme |
| | | C. difficile | H. pylori | C. jejuni | MRSA | S. epidermidis | | E. coli | | C. difficile | Assay (%) |
| R = | | | | | | Plank | Biofilm | Plank | Biofilm | | |
| 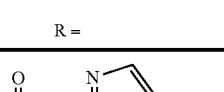 Nitazoxanide | | 52.1 | 13.0 | 39.1 | 39.1 | 52.1 | 32.5 | 104.1 | 26.0 | 100 | 100 |

-continued

Analogues of 2-amino-4-chloro-5-nitrothiazole

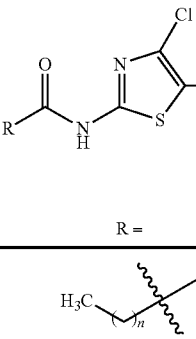

| R = | MIC (μM) | | | | | | | | Disk Diff (%) | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| $H_3C-(\ )_n$ n = 4 VPC162080 | — | 0.9 | 3.6 | 43.2 | 14.4 | — | 115.2 | — | 72 | 116* |
| Phenyl VPC162087 | — | 8.8 | 7.1 | 112.8 | 35.2 | — | 112.8 | — | 66 | 107 |
| 3-CF$_3$-phenyl VPC162088 | — | 5.7 | 34.1 | 11.4 | 8.5 | — | 91.0 | — | 76 | 49** |
| 2-thienyl VPC162089 | — | 6.9 | 13.8 | 110.5 | 82.8 | — | 110.5 | — | — | 93 |

*Biphasic initial inhibition followed by uninhibited rate
**Caused some precipitant in extract

Analogues of 2-amino-3,5-dinitrothiophene

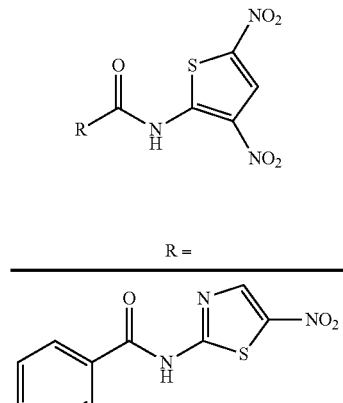

| R = | MIC (μM) | | | | | | | | Disk Diff (%) | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| Nitazoxanide | 52.1 | 13.0 | 39.1 | 39.1 | 52.1 | 32.5 | 104.1 | 26.0 | 100 | 100 |

-continued

Analogues of 2-amino-3,5-dinitrothiophene

R-C(=O)-NH-[2-amino-3,5-dinitrothiophene]

| R = | C. difficile | H. pylori | C. jejuni | MRSA | S. epidermidis Plank | S. epidermidis Biofilm | E. coli Plank | E. coli Biofilm | Disk Diff (%) C. difficile | Direct PFOR Enzyme Assay (%) |
|---|---|---|---|---|---|---|---|---|---|---|
| H₃C-(CH₂)ₙ- , n = 4 VPC16b1089 | — | 2.6 | 0.9 | 55.7 | 20.9 | — | 111.4 | — | 42 | 148* |
| phenyl VPC16b1090 | — | 1.3 | 0.9 | 109.1 | 5.1 | — | 109.1 | — | 0 | 100** |
| 3-CF₃-phenyl VPC16b1092 | — | 0.5 | 2.1 | 1.4 | 0.2 | — | 88.6 | — | 59 | 87** |
| 2-thienyl VPC16b1093 | — | 2.5 | 1.0 | 26.7 | 13.4 | — | 106.9 | — | 43 | 143 |
| 3-furyl VPC16b1094 | — | 2.7 | 0.4 | 56.5 | 28.2 | — | 113.0 | — | 53 | 126* |
| 5-bromo-2-furyl VPC16b2023 | — | 2.1 | 2.8 | 33.1 | 88.4 | — | — | — | — | 94** |
| 5-bromo-2-thienyl VPC16b2025 | — | 2.6 | 2.6 | 63.5 | 15.9 | — | — | — | — | 98** |

-continued

Analogues of 2-amino-3,5-dinitrothiophene

| R = | MIC (μM) | | | | | | | | Disk Diff (%) | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| VPC16b2026 (F₃C-phenyl-Cl) | — | 0.8 | 2.5 | 30.3 | 15.2 | — | — | — | — | 100 |
| VPC16b2028 (phenyl-Cl-CF₃) | — | 0.8 | 1.9 | 30.3 | 30.3 | — | — | — | — | 113 |
| VPC16b2031 (phenyl-O-CH₂CH₂NH₂·HCl) | — | 1.9 | 1.3 | 82.3 | 25.7 | — | — | — | — | 162 |

*Biphasic initial inhibition followed by unhibited rate
**Caused some precipitant in extract

Example 4

Figure 31:
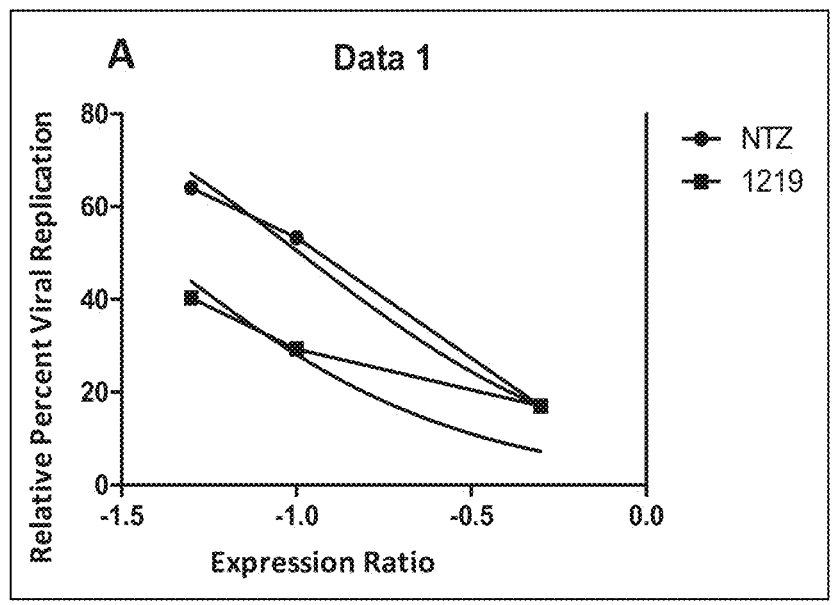
FIG. 31 (A and B). Comparison of Amixin with nitazoxanide in inhibiting the replication of hepatitis C virus in a replicon model. A. The assay is a real time quantitative PCR measure of viral RNA and the drug dose dependent inhibition of viral replication. B. The $IC_{50}$ values for the inhibition of viral replication are presented from two independent experiments showing that Amixin is superior to NTZ by the replicon model.
Figure 31:
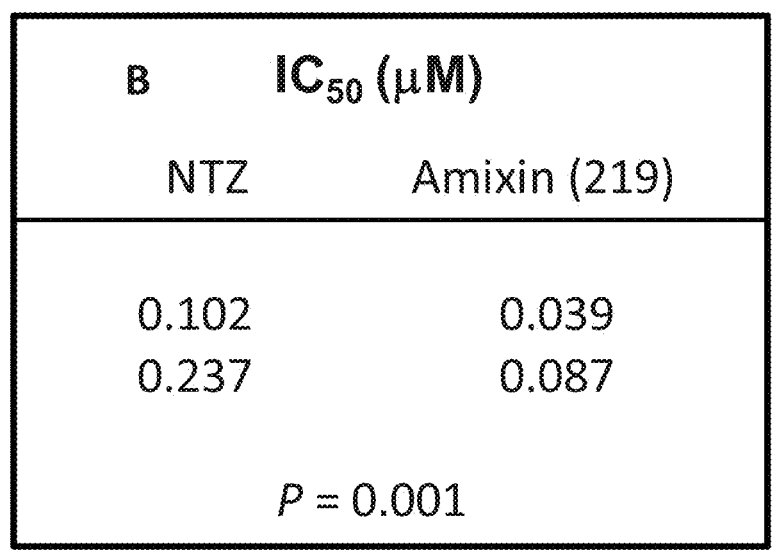

Comparison of Amixin (VPC161219) with Nitazoxanide in Inhibiting the Replication of Hepatitis C Virus in a Replicon Model and Comparison of Amixin with Other Anti-Parasitic Drugs for Efficacy in Treating Amoebic Dysentery in a Mouse Infection Model FIG. 31 provides the results of a comparison of Amixin with nitazoxanide in inhibiting the replication of hepatitis C virus in a replicon model. The data are expressed based on an assay is a real time quantitative PCR measure of viral RNA and the drug dose dependent inhibition of viral replication. The IC$_{50}$ values for the inhibition of viral replication are presented from two independent experiments showing that Amixin is superior to NTZ by the replicon model.

FIG. 32 provides the results of a comparison of Amixin with other anti-parasitic drugs for efficacy in treating amoebic dysentery in a mouse infection model. Comparison of various drugs on $E.\ histolytica$ cell counts showing that Amixin is superior to nitazoxanide based on MIC. The drugs tested include Tinidazole, Amixin219, Metronidazole, Nitazoxanide, Pyrvinium Pamoate, Iodoquinol, Emetine, and Chloroquine (FIG. 32A). The drugs were also compared by either oral or parenteral administration (FIG. 32B); * pval=0.02 (Fisher's Exact) vs PBS; ‡pval=0.02 (Fisher's Exact) vs Metronidazole.

The structure of the novel compound Amixin (VPC161219), also referred to as AMIX herein, is:

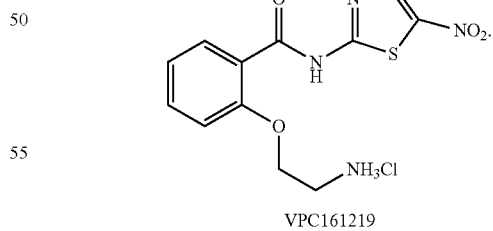

VPC161219

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

What is claimed is:

1. A method of treating or inhibiting a microbial infection or biofilm formation in a subject, said method comprising administering to said subject a pharmaceutical composition comprising a pharmaceutically acceptable carrier, optionally at least one additional therapeutic agent, and a therapeutically effective amount of a compound selected from the group consisting of:

VPC161219
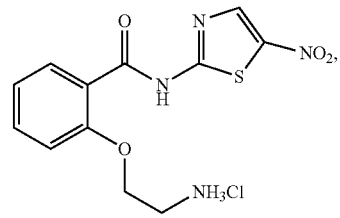

VPC162134
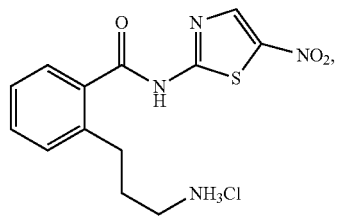

VPC162125
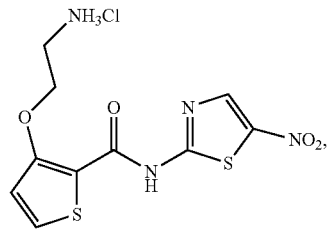

VPC16a1028
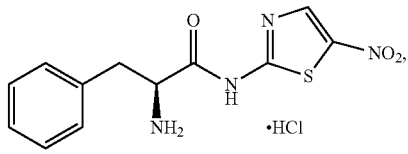

VPC162047
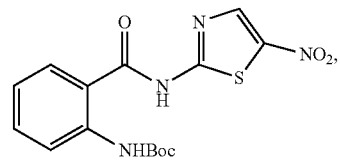

VPC16a1052
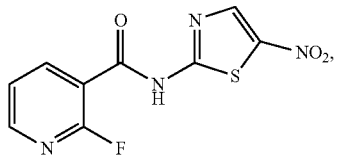

VPC16b1031
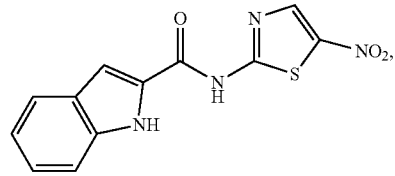

VPC162082
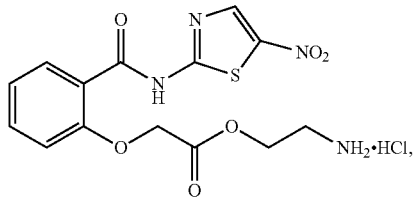

VPC161276
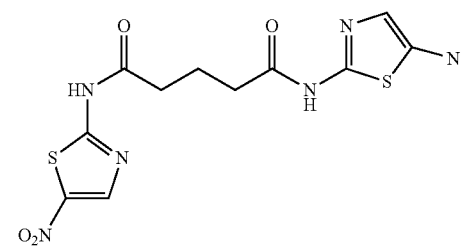

VPC16b1145
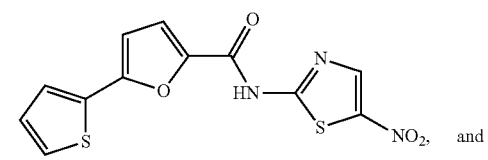
and

VPC161181
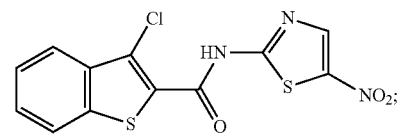

or a pharmaceutically acceptable salt or prodrug thereof.

2. The method of claim 1, wherein said compound is:

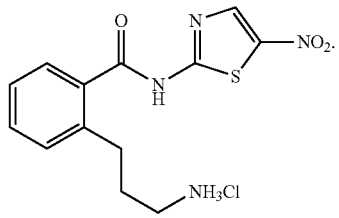
VPC162134

3. The method of claim 1, wherein said compound is:

VPC162125

4. The method of claim 1, wherein said compound is:

VPC161181

5. The method of claim 1, wherein said compound inhibits growth.
6. The method of claim 5, wherein said growth is aerobic growth.
7. The method of claim 1, wherein said compound inhibits attachment.
8. The method of claim 1, wherein said compound inhibits Aap.
9. The method of claim 1, wherein said compound inhibits assembly of AafA fimbriae.
10. The method of claim 1, wherein said compound prevents or inhibits infection.
11. The method of claim 1, wherein said additional therapeutic agent is selected agent is selected from the group consisting of NTZ, TIZ, and AMIX.
12. The method of claim 1, wherein said microbial infection is a bacterial infection or said biofilm formation is bacterial biofilm formation.
13. The method of claim 12, wherein said bacteria are selected from the group consisting of *S. epidermidis*, *E. coli*, *C. difficile*, *H. pylori*, *C. jejuni*, MRSA, and *mycobacterium*.
14. The method of claim 1, wherein said subject is a human.
15. The method of claim 1, wherein at least two compounds are administered.
16. A method of treating or inhibiting a microbial infection or biofilm formation in a subject, said method comprising administering to said subject a pharmaceutical composition comprising a pharmaceutically acceptable carrier, optionally at least one additional therapeutic agent, and a therapeutically effective amount of a compound selected from VPC16b1093

VPC16b2026 and

VPC162031

17. A method of treating or inhibiting a microbial infection or biofilm formation in a subject, said method comprising administering to said subject a pharmaceutical composition comprising a pharmaceutically acceptable carrier, optionally at least one additional therapeutic agent, and a therapeutically effective amount of a compound selected from VPC16a1060 and

VPC161196

* * * * *